(12) United States Patent
Schlessinger et al.

(10) Patent No.: US 7,056,508 B2
(45) Date of Patent: Jun. 6, 2006

(54) RECEPTOR-TYPE PHOSPHOTYROSINE PHOSPHATASE-KAPPA ANTIBODIES

(75) Inventors: Joseph Schlessinger, New York, NY (US); Jan M. Sap, New York, NY (US); Axel Ullrich, München 40 (DE); Wolfgang Vogel, Germering (DE); Miriam Fuchs, Starnberg (DE)

(73) Assignees: New York University, New York, NY (US); Max Planck Gesellschaft Forgerung der Wissenschaften, Munich (DE)

( * ) Notice: Subject to any disclaimer, the term of this patent is extended or adjusted under 35 U.S.C. 154(b) by 671 days.

(21) Appl. No.: 09/887,669

(22) Filed: Oct. 1, 2001

(65) Prior Publication Data

US 2002/0082397 A1    Jun. 27, 2002

Related U.S. Application Data

(60) Continuation of application No. 09/234,883, filed on Jan. 21, 1999, now abandoned, which is a division of application No. 08/087,244, filed on Jul. 1, 1993, now Pat. No. 5,863,755, which is a continuation-in-part of application No. 08/049,384, filed on Apr. 21, 1993, now abandoned.

(51) Int. Cl.
*A61K 39/395* (2006.01)
*C12P 21/08* (2006.01)
*C12P 21/02* (2006.01)
*G01N 33/567* (2006.01)
*C07K 1/00* (2006.01)

(52) U.S. Cl. ............................ 424/143.1; 424/130.1; 530/300; 530/350; 530/388.22; 514/2; 436/501; 435/7.21

(58) Field of Classification Search ............... 530/300, 530/350, 388.22; 536/23.8; 435/6, 7.21, 435/69.1, 252.5, 320.1; 436/501; 424/130.1, 424/143.1; 514/2
See application file for complete search history.

(56) References Cited

OTHER PUBLICATIONS

Alexander et al., Proc. Natl. Acad. Sci. 89(3352-3356)1992.*
Jiang et al., "Cloning and Characterization of R-PTP-K, a New Member of the Receptor Protein Tyrosine Phosphatase Family with a Proteolytically Cleaved Cellular Adhesion Molecule-Like Extracellular Region," *Molecular and Cellular Biology* 13(5):2942-2951 (1993).
LaForgia et al., "Receptor protein-tyrosine phosphatase gamma is a candidate tumor suppressor gene at human chromosome region 3p21". *Proc. Natl. Acad. Sci. USA* 88: 5036-5040, (1991).
Daum et al., "Characterization of a human recombinant receptor-linked protein tyrosine phosphatase", *J. Biol. Chem.*, 266: 12211-12215 (1991).
Gebbink, et al., "Cloning, Expression and Chromosomal Localization of a New Putative Receptor-like Protein Tyrosine Phosphatase", *FEBS Lett.* 290:123-130 (1991).
Kaplan et al., "Cloning of three human tyrosine phosphatases reveals a multigene family of receptor-linked protein-tyrosine-phosphatases expressed in brain," *Proc. Natl. Acad. Sci. USA* 87:7000-7004 (1990).
Sap et al., "Cloning and expression of a widely expressed receptor tyrosine phosphatase," *Proc. Natl. Acad. Sci. USA* 87:6112-6116 (1990).
George and Parker, "Preliminary characterization of phosphotyrosine phosphatase activities in human peripheral blood lymphocytes: Identification of CD45 as a phosphotyrosine phosphatase", *J. Cell Biochem.* 42: 71-81 (1990).
Nishi, et al., "Novel Putative Protein Phosphatases Identified by the Polymerase Chain Reaction". *FEBS Lett.* 271:178-180 (1990).
Jirik et al., "Cloning of a novel receptor-linked protein tyrosine phosphatase from a human hepatoblastoma cell line", *FASEB J.* 4A: 2082 (Abstr. 2253) (1990).
Jirik et al., "Cloning and chromosomal assignment of a widely expressed human receptor-like protein-tyrosine phosphatase," *FEBS Letters* 273(1,2):239-242 (1990).
Krueger et al., "Structural diversity and evolution of human receptor-like protein tyrosine phosphatases," *The EMBO Journal* 9(10):3241-3252 (1990).
Matthews et al., "Identification of an additional member of the protein-tyrosine-phosphatase family: Evidence for alternative splicing in the tyrosine phosphatase domain," *Proc. Natl. Acad. Sci. USA* 87:4444-4448 (1990).
Ohagi et al., "Sequence of a cDNA encoding human LRP (leukocyte common antigen-related peptide)", *Nucl. Acids Res.* 18: 7159 (1990).
Streull et al., "Distinct functional roles of the two intracellular phosphatase like domains of the receptor-linked protein tyrosine phosphatases LCA and LAR", *EMBO J.* 9: 2399-2407 (1990).

(Continued)

*Primary Examiner*—Elizabeth Kemmerer
*Assistant Examiner*—Michael Brannock
(74) *Attorney, Agent, or Firm*—Nicholas I. Slepchuk, Jr.; Gregg C. Benson; Beth A. Burrous

(57) ABSTRACT

A novel receptor-type protein tyrosine phosphatase-κ (RPTPκ) protein or glycoprotein and the DNA coding therefor is expressed in a wide variety of mammalian tissues. The RPTPκ protein or glycoprotein may be produced by recombinant means. Antibodies to the protein, methods for measuring the quantity of the protein, methods for screening compounds, such as drugs, which can bind to the protein and inhibit or stimulate their enzymatic activity, are provided. Further, methods for inhibiting homophilic binding of Type II RPTP, especially RPTPκ molecules are provided.

32 Claims, 37 Drawing Sheets

OTHER PUBLICATIONS

Figure 2:
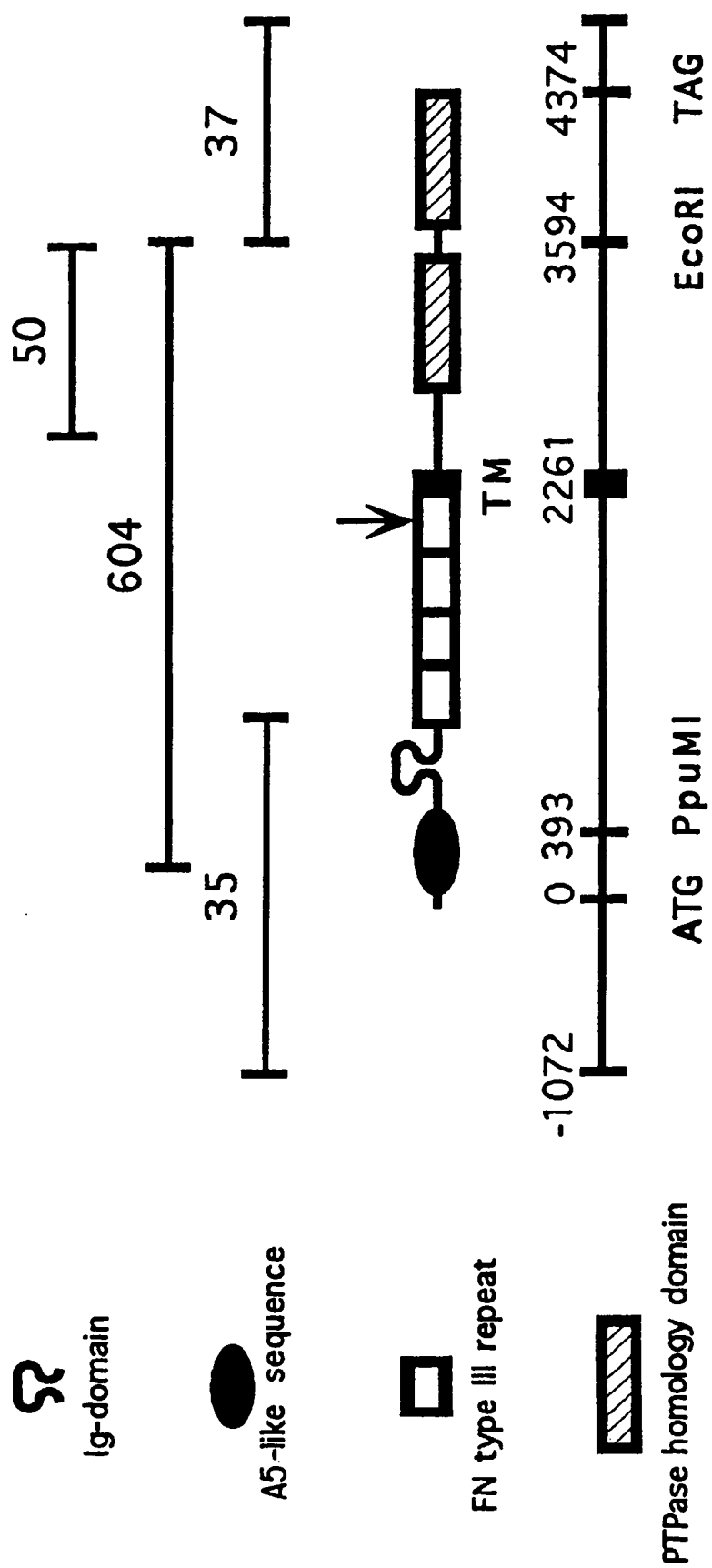

Streuli et al., "A new member of the immunoglobulin superfamily that has a cytoplasmic region homologous to the leukocyte common antigen", *J. Exp. Med.* 168: 1523-1530 (1988).

Tonks et al., "Demonstration That the Leukocyte Common Antigen CD45 is a Protein Tyrosine Phosphatase," *Biochemistry* 27(24):8695-8701 (1988).

Charbonneau et al., "The leukocyte common antigen (CD45): A putative receptor-linked protein tyrosine phosphatase," *Proc. Natl. Acad. Sci. USA* 85:7182-7186 (1988).

Ralph et al., "Structural variants of human T200 glycoprotein (leukocyte-common antigen)", *EMBO J.* 6: 1251-1257 (1987).

Tian et al., "Three receptor-linked protein-tyrosine phosphates are selectively expressed on central nervous system axons in the *Drosophila* embryo". *Cell* 67: 675-685 (1991).

Yang et al., "Tw *Drosophila* receptor-like tyrosine phosphatase genes are expressed in a subset of developing axons and pioneer neurons in the embry nic CNS". *Cell* 67: 661-673 (1991).

Hariharan et al., "Cloning and characterization of a receptor-class phosphotyrosine phosphatase gene expressed on central nervous system axons in *Drosophila melanogaster*", *Proc. Natl. Acad. Sci. USA* 88: 11266-11270 (1991).

Streuli et al., "A family of receptor-linked protein tyrosine phosphatases in humans and *Drosophila*", *Proc. Natl. Acad. Sci. USA* 86: 8698-8702 (1989).

Yi et al., "Protein tyrosine phosphatase containing SH2 domains: characterization, preferential expression in hematopoietic cells, and localization to human chromosome 12p12-p13", *Mol. and Cell. Biol.* 12: 836-846 (1992).

Gu et al., "Identification, cloning, and expression of a cytosolic megakaryocyte protein-tyrosine-phosphatase with sequence homology to cytoskeletal protein 4.1", *Proc. Natl. Acad. Sci. USA* 88: 5867-5871 (1991).

Chernoff et al., "Cloning of a cDNA for a major human protein-tyrosine phosphatase," *Proc. Natl. Acad. Sci. USA* 87:2735-2739 (1990).

Guan et al., "Cloning and expression of a protein-tyrosine-phosphatase," *Proc. Natl. Acad. Sci. USA* 87:1501-1501 (1990).

Charbonneau et al., "Human placenta protein-tyrosine-phosphatase: Amino acid sequence and relationship to a family of receptor-like proteins," *Proc. Natl. Acad. Sci. USA* 86:5252-5256 (1989).

Cool et al., "cDNA isolated from a human T-cell library encodes a member of the protein-tyrosine-phosphatase family," *Proc. Natl. Acad. Sci. USA* 86:5257-5761 (1989).

Pallen et al., Purification of a phosphotyrosine phosphatase that dephosphorylates the epidermal growth-factor receptor autophosphorylation sites, Ann. N.Y. Acad. Sci. 551: 299-308 (1988).

Zheng et al., "Cell transformation and activation of pp60 $^{c-stc}$ by overexpression of a protein tyrosine phosphatase". *Nature* 359: 336-339 (1992).

Haughn et al., "Association of tyrosine kinase p56$^{lck}$ with CD4 inhibits the induction of growth through the αβ T-cell receptor". *Nature* 358: 328-331 (1992).

Mustelin et al., "Rapid activation of the T-cell tyrosine protein kinase pp56lck by the CD45 phosphotyrosine phosphatase", *Proc. Natl. Acad. Sci. USA* 86: 6302-6306 (1989).

Ostergaard et al., "Expression of CD45 alters *phosphrylation of the lck-encoded tyrosine protein kinase in murine lymphoma T-cell lines*", Proc. Natl. Acad. Sci. USA 86: 8959-8963 (1989).

Klarlund, "Transformation of cells by an inhibitor of phosphatases acting on phosph tyrosine in proteins", *Cell* 41: 707-717 (1985).

Beckmann and Bork., "An Adhesive Domain Detected in Functionally diverse receptors," *TIBS* 18:40-41 (1993).

O'Bryan et al., "axl, a transforming gene islated from primary human myeloid leukemia cells, encodes a novel receptor tyrosine kinase". *Mol. Cell. Biol.* 11: 5016-5031 (1991).

Rescigno et al., "A putative receptor tyrosine kinase with unique structural topology". *Oncogene* 6: 1909-1913 (1991).

Burgoon et al., "Structure of chicken neuron-glia cell adhesion molecule, Ng-CAM: origin of the polypeptides and relation to the Ig superfamily". *J. Cell. Biol.* 112: 1017-1029 (1991).

Bieber et al., "*Drosophila neuroglian*: a member of the immunoglobulin superfamily with extensive homology to the vertebrate neural adhesion molecule L1", *Cell* 59: 447-460 (1989).

Takagi et al., "The A5 Antigen, a Candidate for the Neuronal Recongnition Molecule, Has Homologies to Complement Components and Coagulation Factors," *Neuron* 7:295-307 (1991).

Blaschuk et al., "Identification of a Conserved Region Common to Cadherins and Influenza Strain A Hemagglutinis," *J.Mol. Biol.* 211:679-682 (1990).

Hosaka et al., "Arg-X-Lys/Arg-Arg motif as a signal for precursor cleavage catalyzed by furin within the constitutive secretory pathway". *J. Biol. Chem.* 266: 12127-12130 (1991).

Kornblihtt et al., "Primary structure of human fibronectin: differential splicing may generate at least 10 polypeptides from a single gene". *EMBO J.* 4: 1755-1759 (1985).

Schlessinger and Ullrich, "Growth Factor Signalling by Receptor Tyrosine Kinases," *Neuron* 9:383-391 (1992).

Pot and Dixon, "A thousand and two protein tyrosine phosphatases," *Biochimica et Biophysica Acta* 1136:35-43 (1992).

Fischer et al., "Protein Tyrosine Phosphatases: A Diverse Family of Intracellular and Transmembrane Enzymes," *Science* 253:401-406 (1991).

Saito and Streuli, "Molecular Characterization of Protein Tyrosine Phosphatases," *Cell Growth & Differentation* 2(1):59-65 (1991).

Klausner and Samelson, "T cell antigen receptor activation pathways: The tyrosine kinase connection". *Cell* 64:875-878 (1991).

Kjellen and Lindahl, "Proteoglycans: structures and interactions". *Ann. Rev. Biochem.* 60: 443-475 (1991).

Ullrich and Schlessinger, "Signal Transduction by Receptors with Tyrosine Kinase Activity," *Cell* 61:203-212 (1990).

Hunter, "Protein-Tyrosine Phosphatases: The Other Side of the Coin," *Cell* 58:1013-1016 (1989).

Thomas, "The leukocyte common antigen family", *Ann. Rev. Immunol.* 7: 339-369 (1989).

Yarden and Ullrich, "Growth Factor Receptor Tyrosine Kinases, " *Ann. Rev. Biochem.* 57:443-478 (1988).

Maniatis, et al., *Molecular Cloning: A Laboratory Manual*, 2$^{nd}$ *Edition*, Cold Spring Harbor Laboratory Press (1989) (Table of Contents—All Three Volumes).

Sambrook et al., *Molecular Cloning, Second Edition*, vol. 3 pp. 16.2-16.30 and 17.2-17.28, Cold Spring Harbor Laboratory Press, New York, (1989).

Hoffman et al., "Kinetics of Homophilic Binding by Embryonic and Adult forms of the Neural Cell Adhension Molecule". *Proc. Natl. Acad. Sci.*, USA 80:5762-5766 (1983).

Colwell, et al., "Methods in Enzymology", *Academic Press, Inc.* 121, 42-51, (1986).

* cited by examiner

```
SIGNAL     1  atggatgtggcggccgctgcgttgcctgcttttgtagctctctggcttctgtacccgtgg  60
PEPTIDE    1  [M  D  V  A  A  A  A  L  P  A  F  V  A  L  W  L  L  Y  P  W   20

61  cctctcctggggtcggcccttggccagttctcagcaggtggctgtactttgatgatggg 120
          21   P  L  L  G  S] A  L  G  Q  F  S  A [G  C  T  F  D  D  G   40

A5
HOMOLOGY 121  ccaggggcttgtgactaccaccaggatttatacgatgactttgagtgggtccatgtcagt 180
REGION    41   P  G  A  C  D  Y  H  Q  D  L  Y  D  D  F  E  W  V  H  V  S   60

181  gcgcaggaacctcattacctgccccccgaaatgcctcaaggttcctatatggttgtggac 240
          61   A  Q  E  P  H  Y  L  P  P  E  M  P  Q  G  S  Y  M  V  V  D   80

241  tcctcaaatcatgatcctggagaaaaagccagacttcagctgcctaccatgaaggagaat 300
          81   S  S  N  H  D  P  G  E  K  A  R  L  Q  L  P  T  M  K  E  N  100

301  gacacccactgcattgatttcagttaccttgttatatagccagaaggggttgaaccctggc 360
         101   D  T  H  C  I  D  F  S  Y  L  L  Y  S  Q  K  G  L  N  P  G  120

361  actttgaatatcctagttagggtgaataaaggacctcttgctaatccaatttggaatgta 420
         121   T  L  N  I  L  V  R  V  N  K  G  P  L  A  N  P  I  W  N  V  140

421  actggattcactggtcgtgattggcttcgggctgaactagctgtgagcacctttggccc 480
         141   T  G  F  T  G  R  D  W  L  R  A  E  L  A  V  S  T  F  W  P  160

481  aatgaataccaggtaatatttgaagctgaagtctcaggagggagaagtggttatattgcc 540
         161   N  E  Y  Q  V  I  F  E  A  E  V  S  G  G  R  S  G  Y  I  A  180

541  attgatgacatccaagtcctgagttatccttgcgataaatctcctcattttctccgcctt 600
         181   I  D  D  I  Q  V  L  S  Y] P  C  D  K  S  P  H  F  L  R  L  200
```

FIG.1A

```
601 ggtgatgtggaggtcaatgctgggcagaatgctacatttcagtgcattgctacagggaga 660
201  G  D  V  E  V  N  A  G  Q  N  A  T  F  Q  C  I  A  T  G  R  220

661 gatgctgtgcataacaagttatggctgcagagacgcaatggagaagacatacccgtagcc 720
221  D  A  V  H  N  K  L  W  L  Q  R  R  N  G  E  D  I  P  V  A  240

721 cagactaagaacataaatcacagaagatttgctgcctctttcagattgcaagaagtgaca 780
241  Q  T  K  N  I  N  H  R  R  F  A  A  S  F  R  L  Q  E  V  T  260

781 aaaactgaccaggatttgtaccgctgcgtaactcagtcagaacgaggttctggggtttcc 840
261  K  T  D  Q  D  L  Y  R  C  V  T  Q  S  E  R  G  S  G  V  S  280

841 aatttTgctcaactcattgtgagagaaccacctagacccattgctcctcccCagctgctt 900
281  N  F  A  Q  L  I  V  R  E  P  P  R  P  I  A  P  P  Q  L  L  300

901 ggtgttgggcctacttacttgctgatccaactaaatgccaactctattattggcgatggc 960
301  G  V  G  P  T  Y  L  L  I  Q  L  N  A  N  S  I  I  G  D  G  320

961 cccatcatcctgaaagaagtagagtatcgaatgacatcaggatcttggacagaaacccat 1020
321  P  I  I  L  K  E  V  E  Y  R  M  T  S  G  S  W  T  E  T  H  340

1021 gcagtcaacgcaccaacatataagttgtggcatttagacccagatacagaatacgagatc 1080
341   A  V  N  A  P  T  Y  K  L  W  H  L  D  P  D  T  E  Y  E  I  360

1081 cgcgtcctgcttaccagacctggcgaaggggggaactgggctgccaggaccaccactgatc 1140
361   R  V  L  L  T  R  P  G  E  G  G  T  G  L  P  G  P  P  L  I  380

1141 actagaacgaagtgtgcagaacctatgcggacaccaaagactttaaagattgctgaaatc 1200
381   T  R  T  K  C  A  E  P  M  R  T  P  K  T  L  K  I  A  E  I  400
```

FIG.1B

```
1201  caggcaaggcgcattgcagtggactggggagtccttgggctacaacatcactcgttgccac  1260
 401   Q   A   R   R   I   A   V   D   W   E   S   L   G   Y   N   I   T   R   C   H    420

1261  actttcaacgtcactatctgctaccattacttccgtggccacaatgagagcagggcagac  1320
 421   T   F   N   V   T   I   C   Y   H   Y   F   R   G   H   N   E   S   R   A   D    440

1321  tgcttggacatggaccccaaagcccctcagcatgttgtgaaccatctgccaccttacaca  1380
 441   C   L   D   M   D   P   K   A   P   Q   H   V   V   N   H   L   P   P   Y   T    460

1381  aatgtcagcctcaagatgatcctaaccaacccagaggggaaggaaggagagcgaagagaca  1440
 461   N   V   S   L   K   M   I   L   T   N   P   E   G   R   K   E   S   E   E   T    480

1441  atcatccaaactgatgaagatgtgcccggggcctgtgccagtcaaatccctccaaggaaca  1500
 481   I   I   Q   T   D   E   D   V   P   G   P   V   P   V   K   S   L   Q   G   T    500

1501  tcctttgaaaacaagatcttcctgaactggaaagagccactggaaccgaatggaattatc  1560
 501   S   F   E   N   K   I   F   L   N   W   K   E   P   L   E   P   N   G   I   I    520

1561  actcagtatgaggtgagctatagcagcataagatcatttgaccctgctgttccagtggct  1620
 521   T   Q   Y   E   V   S   Y   S   S   I   R   S   F   D   P   A   V   P   V   A    540

1621  gggcccccacagactgtatcaaatttatggaatagtacacaccatgtatttatgcatctt  1680
 541   G   P   P   Q   T   V   S   N   L   W   N   S   T   H   H   V   F   M   H   L    560

1681  caccctggaaccacctaccagttttttataagagccagcactgtcaaaggctttggacca  1740
 561   H   P   G   T   T   Y   Q   F   F   I   R   A   S   T   V   K   G   F   G   P    580

1741  gcaacagccatcaatgtgaccacaaatatctcagctccaagcttacctgactatgaagga  1800
 581   A   T   A   I   N   V   T   T   N   I   S   A   P   S   L   P   D   Y   E   G    600
```

FIG.1C

```
1801 gttgatgcctctctgaatgaaactgccaccaccatcacagtactattgaggcctgcacaa 1860
601   V  D  A  S  L  N  E  T  A  T  T  I  T  V  L  L  R  P  A  Q   620

1861 gccaaaggtgctcctatcagtgcttatcaaattgttgtggagcagctacacccacatcga 1920
621   A  K  G  A  P  I  S  A  Y  Q  I  V  V  E  Q  L  H  P  H  R   640

1921 acgaagcgtgaagcaggggccatggaatgctaccaggtaccggttacataccagaacgcc 1980
641   T  K  R  E  A  G  A  M  E  C  Y  Q  V  P  V  T  Y  Q  N  A   660

1981 ctaagtgggggcgcgccctattactttgccgcagaacttccccctgggaatcttcccgag 2040
661   L  S  G  G  A  P  Y  Y  F  A  A  E  L  P  P  G  N  L  P  E   680

2041 cctgctcccttcaccgtgggtgacaaccggacctataaaggcttttggaaccctcccctg 2100
681   P  A  P  F  T  V  G  D  N  R  T  Y  K  G  F  W  N  P  P  L   700

2101 gccccccgcaaaggatacaacatctatttccaagcgatgagcagtgtggagaaggaaact 2160
701   A  P  R  K  G  Y  N  I  Y  F  Q  A  M  S  S  V  E  K  E  T   720

2161 aaaacccaatgtgtacgaattgctacaaaaagcagcagcaacagaagaaccagaagtgatc 2220
721   K  T  Q  C  V  R  I  A  T  K  A  A  A  T  E  E  P  E  V  I   740

2221 ccagacccggcaaagcagacagacagagtggtgaaaatcgcgggcatcagtgctggcatc 2280
741   P  D  P  A  K  Q  T  D  R  V  V  K [I  A  G  I  S  A  G  I   760
```
TRANS-
MEMBRANE
```
2281 ctagtgttcatccttctcctgctggttgtcatagtaattgtgaaaaagagcaagcttgct 2340
761   L  V  F  I  L  L  L  V  V  I  V  I  V] K  K  S  K  L  A   780

2341 aagaagcgcaaagatgcaatggggaacacacgtcaggagatgacccacatggtgaatgct 2400
781   K  K  R  K  D  A  M  G  N  T  R  Q  E  M  T  H  M  V  N  A   800
```

FIG.1D

```
           2401  atggaccgaagttatgctgaccagagcacccctgcatgcagaagacccccttccctcacc  2460
            801   M  D  R  S  Y  A  D  Q  S  T  L  H  A  E  D  P  L  S  L  T   820

2461  ttcatggaccaacataacttcagtccaagattgcccaatgatccacttgtgccgactgcc  2520
            821   F  M  D  Q  H  N  F  S  P  R  L  P  N  D  P  L  V  P  T  A   840

2521  gtgttagatgagaaccacagtgccacagcagagtctagtcgtctcctggatgttcctcga  2580
            841   V  L  D  E  N  H  S  A  T  A  E  S  S  R  L  L  D  V  P  R   860

2581  tacctctgcgaagggacagagtccccttatcagacaggacagctgcacccagccatcagg  2640
            861   Y  L  C  E  G  T  E  S  P  Y  Q  T  G  Q  L  H  P  A  I  R   880

2641  gtggccgacttactgcagcacattaacctcatgaagacatcagacagctatgggttcaaa  2700
            881   V  A  D  L  L  Q  H  I  N  L  M  K  T  S  D  S  Y  G  F  K   900

2701  gaggaatacgagagcttcttlgaaggccagtcagcctcttgggatgtggctaaaaaggat  2760
            901   E  E  Y  E  S  F  F  E  G  Q  S  A  S  W  D  V  A  K  K  D   920

PTPase      2761  caaaacagagcaaagaaccgatacggaaacattatcgcatatgatcactccagagtcatc  2820
DOMAIN I     921   Q  N  R  A  K [N  R  Y  G  N  I  I  A  Y  D  H  S  R  V  I   940

2821  ctgcaacctgtggaagatgaccctlcttcagattacattaatgccaactacatcgacatt  2880
            941   L  Q  P  V  E  D  D  P  S  S  D  Y  I  N  A  N  Y  I  D  I   960

2881  tggctgtacagggatggctaccagagaccaagccactacattgcaactcaaggcccagtt  2940
            961   W  L  Y  R  D  G  Y  Q  R  P  S  H  Y  I  A  T  Q  G  P  V   980

2941  catgaaaccgtatatgatttttggaggatggtgtggcaagagcagtctgcctgtattgtg  3000
            981   H  E  T  V  Y  D  F  W  R  M  V  W  Q  E  Q  S  A  C  I  V   1000
```

FIG.1E

```
3001  atggtcactaatttagtggaagttggccgggtgaaatgctataaatattggcctgatgat  3060
1001   M  V  T  N  L  V  E  V  G  R  V  K  C  Y  K  Y  W  P  D  D   1020

3061  actgaggtttatggtgacttcaaagtcacctgcgtagaaatggagccacttgctgagtat  3120
1021   T  E  V  Y  G  D  F  K  V  T  C  V  E  M  E  P  L  A  E  Y   1040

3121  gtcgttaggacattcaccttggaaaggaggggctataatgaaatccgtgaagtcaaacag  3180
1041   V  V  R  T  F  T  L  E  R  R  G  Y  N  E  I  R  E  V  K  Q   1060

3181  ttccacttcactggctggcctgaccatggtgttccataccacgcaacagggctcctgtca  3240
1061   F  H  F  T  G  W  P  D  H  G  V  P  Y  H  A  T  G  L  L  S   1080

3241  tttatccggagagtcaagctatctaaccctcccagtgctgggcccattgtcgtacactgc  3300
1081   F  I  R  R  V  K  L  S  N  P  P  S  A  G  P  I  V  V  H  C   1100

3301  agtgctggtgctgggcgcacaggctgttacattgttattgacataatgctggacatggct  3360
1101   S  A  G  A  G  R  T  G  C  Y  I  V  I  D  I  M  L  D  M  A   1120

3361  gaaagagagggtgtggttgacatctacaactgtgtgaaagccttacgatctcggcgcatt  3420
1121   E  R  E  G  V  V  D  I  Y  N  C  V  K  A  L  R  S  R  R  I   1140

3421  aatatggtacagacagaggaacagtacattttttattcatgatgccatttagaagcctgc  3480
1141   N  M  V  Q  T  E  E  Q  Y  I  F  I  H  D  A  I  L  E] A  C   1160

3481  ttatgtggagaaactgccatccctgtgtgtgaatttaaagctgcatattttgatatgatt  3540
1161   L  C  G  E  T  A  I  P  V  C  E  F  K  A  A  Y  F  D  M  I   1180

3541  cgaatagactctcagactaactcctctcatctcaaagatgaatttcagactctgaattcg  3540
1161   L  C  G  E  T  A  I  P  V  C  E  F  K  A  A  Y  F  D  M  I   1180
```

FIG.1F

```
              3541 cgaatagactctcagactaactcctctcatctcaaagatgaatttcagactctgaattcg 3600
              1181  R  I  D  S  Q  T  N  S  S  H  L  K  D  E  F  Q  T  L  N  S  1200

PTPase        3601 gtcaccccctcgactacaagctgaagactgcagcatagcctgcctgccaaggaaccatgac 3660
DOMAIN II     1201  V  T  P  R  L  Q  A  E  D  C  S  I  A  C  L  P  R [N  H  D  1220

3661 aagaaccgtttcatggatatgctcccacctgacagatgtctgccttttttaattacaatt 3720
              1221  K  N  R  F  M  D  M  L  P  P  D  R  C  L  P  F  L  I  T  I  1240

3721 gatggggagagcagtaactacatcaatgctgctcttatggatagctataggcagccagca 3780
              1241  D  G  E  S  S  N  Y  I  N  A  A  L  M  D  S  Y  R  Q  P  A  1260

3781 gctttcatcgtcacacaatacccactgccaaacactgtgaaagacttctggagattagta 3840
              1261  A  F  I  V  T  Q  Y  P  L  P  N  T  V  K  D  F  W  R  L  V  1280

3841 tatgattacggatgtacctccatcgtgatgctaaatgaagtggacctgtctcagggctgc 3900
              1281  Y  D  Y  G  C  T  S  I  V  M  L  N  E  V  D  L  S  Q  G  C  1300

3901 ccacagtactggccagaagaaggaatgctgcgatatggtcctatccaagtggaatgtatg 3960
              1301  P  Q  Y  W  P  E  E  G  M  L  R  Y  G  P  I  Q  V  E  C  M  1320

3961 tcttgttcaatggactgtgatgtgatcaatcgaattttttagaatatgcaacctaacgaga 4020
              1321  S  C  S  M  D  C  D  V  I  N  R  I  F  R  I  C  N  L  T  R  1340

4021 ccacaggagggctatctgatggtacaacagttccagtacctaggctgggcttctcatcga 4080
              1341  P  Q  E  G  Y  L  M  V  Q  Q  F  Q  Y  L  G  W  A  S  H  R  1360

4081 gaagtgcctggctccaaacgctcgttttttgaaattgatactgcaggtggaaaaatggca 4140
              1361  E  V  P  G  S  K  R  S  F  L  K  L  I  L  Q  V  E  K  W  Q  1380
```

FIG.1G

```
4141  gaggaatgtgaagaaggggaaggccggacaatcatccactgcttgaatggcggtgggcgc  4200
1381  E   E   C   E   E   G   E   G   R   T   I   I   H   C   L   N   G   G   R    1400

4201  agtggcatgttctgtgccataggcattgttgtggagatggtgaagcggcaaaatgtggtg  4260
1401  S   G   M   F   C   A   I   G   I   V   V   E   M   V   K   R   Q   N   V   V    1420

4261  gatgttttccatgcagtaaaagacgctgaggaacagcaagccaaacatggtggaagccccg  4320
1421  D   V   F   H   A   V   K   T   L   R   N   S   K   P   N   M   V   E   A   P    1440

4321  gagcagtatcgtttttgctatgatgtggcgttagagtacctggagtcctcatag  4374
1441  E   Q   Y   R   F   C   Y   D   V   A   L   E   Y   L   E]  S   S   *    1458
```

FIG.1H

FIG. 3

```
I    (296)    P PQL L GVGPTYLIQLNANS I IGDGPIILKEVE Y RMTSGSWIETHAVNAPTYKLWHLDPDTE.YEIRVLL T R PG EG G TGLPGPPLITRT
II   (392)    P .KT L KIAEIQA..RRIAVD W ESLGYNITRCHT F NVTICYHYFRGHNESRADCLDMDPKA...PQHVVNH L P PY TN V SLKMIL.TNPEG
III  (493)    P VKS L QCTSFE...NKIFLN W KEPLEPNGIITQ Y EVSYSSIRSFDPAVPVAGPPQTVSNLWMSTHHVFMH L H PG TT Y QFFIRASTVKGF
IV   (596)    P DYE G VDASLNETATTITVL L RPAQAKGAPISA Y QIVEQLHPRTKR.EAGAMECYQV....PVTYQNA L S GG AP Y YFAAELPPGNLP
FBN-III(7)   P PTN L HLEANPDT.GVLTVS W ERSTTPD..ITG Y RITTIPINGQQGNSLEEVVHADQ......SSCTFDN L S PG LE Y NVSVY..TVKDD
```

FIG.4

```
PTP-κ(34)    GGCTFDDGPGACDYHQDL YDDFEWVHVSAQE.PHYLPPEMPQGSYMVVDSSNHDPGEKARLQLPTMKEN.DTHCIDFSYLLYSQK
PTP-μ(26)    GGCLFDEPYSTCGYSQADEDDF NMEQVNTLTKPT.SDPMWPSGSFMLVNTSGKPEGQRAHLLPQLKEN.DTHCIDFHYFVSSKS
A5  (651)    CKFGWGSQKTVCNWQHDISSDLKWAVLNSKTGP..VQDHTGDGNFIYSEADERHEGRAARLMSPVVSSSRSAHCLTFWYHM...D
Consensus    ——————C——D——D——W——N—T—P——————G—F———————HC—F—Y—

PTP-κ        GLNPGTLNILVRVN.KGPLANPIWNVTGFTGRDWLRAELAVSTFWPNEYQVIFEAEVSGGRSGYIAIDDIQVLSY
PTP-μ        NAAPGLLNVYVKVN.NGPLGNPIWNISGDPTRTWHRAELAISTFWPNFYQVIFEV.VTSGHQGYLAIDEVKVLGH
A5           GSHVGTLSIKLKYEMEEDFDQTLWTVSGNQGDQMKEARVVLHKTIMKQ.YQVIVEGTVGKGSAGGIAVDDIIIANH
Consensus    G———GTL—I—I———————W—VSG—G——W——A————YQVI—E——G——G—IA—DDI————H
```

FIG.5

```
  1 ATGGATACGACTGCGGCGGCGGCGCTGCCTGCTTTTGTGGCGCTCTTGCTCCTCTCTCCTTGGCCTCTCCTGGGATCGGC  80
  1  M  D  T  T  A  A  A  A  L  P  A  F  V  A  L  L  L  L  S  P  W  P  L  L  G  S  A    27

81 CCAAGGCCAGTTCTCCGCAGGTGGCTGTACTTTTGATGATGGTCCAGGGGCCTGTGATTACCACCAGGATCTGTATGATG 160
 27  Q  G  Q  F  S  A  G  G  C  T  F  D  D  G  P  G  A  C  D  Y  H  Q  D  L  Y  D  D    53

161 ACTTTGAATGGGTGCATGTTAGTGCTCAAGAGCCTCATTATCTACCACCCGAGATGCCCCAAGGTTCCTATATGATAGTG 240
 54     F  E  W  V  H  V  S  A  Q  E  P  H  Y  L  P  P  E  M  P  Q  G  S  Y  M  I  V    80

241 GACTCTTCAGATCACGACCCTGGAGAAAAAGCCAGACTTCAGCTGCCTACAATGAAGGAGAACGACACTCACTGCATTGA 320
 81  D  S  S  D  H  D  P  G  E  K  A  R  L  Q  L  P  T  M  K  E  N  D  T  H  C  I  D   107

321 TTTCAGTTACCTATTATATAGCCAGAAAGGACTGAATCCTGGCACTTTGAACATATTAGTTAGGGTGAATAAAGGACCTC 400
107  F  S  Y  L  L  Y  S  Q  K  G  L  N  P  G  T  L  N  I  L  V  R  V  N  K  G  P  L   133

401 TTGCCAATCCAATTTGGAATGTGACTGGATTCACGGGTAGAGATTGGCTTCGGGCTGAGCTAGCAGTGAGCACCTTTTGG 480
134     A  N  P  I  W  N  V  T  G  F  T  G  R  D  W  L  R  A  E  L  A  V  S  T  F  W   160

481 CCCAATGAATATCAGGTAATATTTGAAGCTGAAGTCTCAGGAGGGAGAAGTGGTTATATTGCCATTGATGACATCCAAGT 560
161  P  N  E  Y  Q  V  I  F  E  A  E  V  S  G  G  R  S  G  Y  I  A  I  D  D  I  Q  V   187

561 ACTGAGTTATCCTTGTGATAAATCTCCTCATTTCCTCCGTCTAGGGGATGTAGAGGTGAATGCAGGGCAAAACGCTACAT 640
187  L  S  Y  P  C  D  K  S  P  H  F  L  R  L  G  D  V  E  V  N  A  G  Q  N  A  T  F   213

641 TTCAGTGCATTGCCACAGGGAGAGATGCTGTGCATAACAAGTTATGGCTCCAGAGACGAAATGGAGAAGATATACCAGTA 720
214     Q  C  I  A  T  G  R  D  A  V  H  N  K  L  W  L  Q  R  R  N  G  E  D  I  P  V   240

721 GCCCAGACTAAGAACATCAATCATAGAAGGTTTGCCGCTTCCTTCAGATTGCAAGAAGTGACAAAAACTGACCAGGATTT 800
241  A  Q  T  K  N  I  N  H  R  R  F  A  A  S  F  R  L  Q  E  V  T  K  T  D  Q  D  L   267

801 GTATCGCTGTGTAACTCAGTCAGAACGAGGTTCCGGTGTGTCCAATTTTGCTCAACTTATTGTGAGAGAACCGCCAAGAC 880
267  Y  R  C  V  T  Q  S  E  R  G  S  G  V  S  N  F  A  Q  L  I  V  R  E  P  P  R  P   293

881 CCATTGCTCCTCCTCAGCTTCTTGGTGTTGGGCCTACATATTTGCTGATCCAACTAAATGCCAACTCGATCATTGGCGAT 960
294     I  A  P  P  Q  L  L  G  V  G  P  T  Y  L  L  I  Q  L  N  A  N  S  I  I  G  D   320

961 GGTCCTATCATCCTGAAAGAAGTAGAGTACCGAATGACATCAGGATCCTGGACAGAAACCCATGCAGTCAATGCTCCAAC 1040
321  G  P  I  I  L  K  E  V  E  Y  R  M  T  S  G  S  W  T  E  T  H  A  V  N  A  P  T   347
```

FIG.15A

```
1041 TTACAAATTATGGCATTTAGATCCAGATACCGAATATGAGATCCGAGTTCTACTTACAAGACCTGGTGAAGGTGGAACGG 1120
347   Y  K  L  W  H  L  D  P  D  T  E  Y  E  I  R  V  L  L  T  R  P  G  E  G  G  T  G  373

1121 GGCTCCCAGGACCTCCACTAATCACCAGAACAAAATGTGCAGAACCTATGAGAACCCCAAAGACATTAAAGATTGCTGAA 1200
374   L  P  G  P  P  L  I  T  R  T  K  C  A  E  P  M  R  T  P  K  T  L  K  I  A  E  400

1201 ATACAGGCAAGACGGATTGCTGTGGACTGGGAATCCTTGGGTTACAACATTACGCGTTGCCACACTTTTAATGTCACTAT 1280
401   I  Q  A  R  R  I  A  V  D  W  E  S  L  G  Y  N  I  T  R  C  H  T  F  N  V  T  I  427

1281 CTGCTACCATTACTTCCGTGGTCACAACGAGAGCAAGGCAGACTGTTTGGACATGGACCCCAAAGCCCCTCAGCATGTTG 1360
427   C  Y  H  Y  F  R  G  H  N  E  S  K  A  D  C  L  D  M  D  P  K  A  P  Q  H  V  V  453

1361 TGAACCATCTGCCACCTTATACAAATGTCAGCCTCAAGATGATCCTAACCAATCCAGAGGGAAGGAAGGAGAGTGAAGAG 1440
454   N  H  L  P  P  Y  T  N  V  S  L  K  M  I  L  T  N  P  E  G  R  K  E  S  E  E  480

1441 ACAATTATTCAAACTGATGAAGATGTGCCCTGGTCCCGTACCAGTAAAATCTCTTCAAGGAACATCCTTTGAAAATAAGAT 1520
481   T  I  I  Q  T  D  E  D  V  P  G  P  V  P  V  K  S  L  Q  G  T  S  F  E  N  K  I  507

1521 CTTCTTGAACTGGAAAGAACCTTTGGATCCAAATGGAATCATCACTCAATATGAGATCAGCTATAGCAGTATAAGATCAT 1600
507   F  L  N  W  K  E  P  L  D  P  N  G  I  I  T  Q  Y  E  I  S  Y  S  S  I  R  S  F  533

1601 TTGATCCTGCAGTCCCAGTGGCTGGACCTCCCCAGACTGTATCAAATTTATGGAACAGTACACACCATGTCTTTATGCAT 1680
534   D  P  A  V  P  V  A  G  P  P  Q  T  V  S  N  L  W  N  S  T  H  H  V  F  M  H  560

1681 CTCCACCCTGGAACCACGTACCAGTTTTTCATAAGAGCCAGCACGGTCAAAGGCTTTGGTCCAGCCACAGCCATCAATGT 1760
561   L  H  P  G  T  T  Y  Q  F  F  I  R  A  S  T  V  K  G  F  G  P  A  T  A  I  N  V  587

1761 CACCACCAATATCTCAGCTCCAACTTTACCTGACTATGAAGGAGTTGATGCCTCTCTCAATGAAACTGCCACCACAATAA 1840
587   T  T  N  I  S  A  P  T  L  P  D  Y  E  G  V  D  A  S  L  N  E  T  A  T  T  I  T  613

1841 CTGTATTGTTGAGACCAGCACAAGCCAAAGGTGCTCCTATCAGTGCTTATCAGATTGTTGTGGAAGAACTGCACCCACAC 1920
614   V  L  L  R  P  A  Q  A  K  G  A  P  I  S  A  Y  Q  I  V  V  E  E  L  H  P  H  640

1921 CGAACCAAGAGAGAAGCCGGAGCCATGGAATGCTACCAGGTTCCTGTCACATACCAAAATGCCATGAGTGGGGGTGCACC 2000
641   R  T  K  R  E  A  G  A  M  E  C  Y  Q  V  P  V  T  Y  Q  N  A  M  S  G  G  A  P  667

2001 GTATTACTTTGCTGCAGAACTACCCCCGGGAAACCTACCTGAGCCTGCCCCGTTCACTGTGGGTGACAATCGGACCTACC 2080
667   Y  Y  F  A  A  E  L  P  P  G  N  L  P  E  P  A  P  F  T  V  G  D  N  R  T  Y  Q  693

2081 AAGGCTTTTGGAACCCTCCTTTGGCTCCGCGCAAAGGATACAACATCTATTTCCAGGCGATGAGCAGTGTGGAGAAGGAA 2160
694   G  F  W  N  P  P  L  A  P  R  K  G  Y  N  I  Y  F  Q  A  M  S  S  V  E  K  E  720
```

FIG.15B

```
2161 ACTAAAACCCAGTGCGTACGCATTGCTACAAAAGCAGCAACAGAAGAACCAGAAGTGATCCCAGATCCCGCCAAGCAGAC 2240
 721   T  K  T  Q  C  V  R  I  A  T  K  A  A  T  E  E  P  E  V  I  P  D  P  A  K  Q  T  747

2241 AGACAGAGTGGTGAAAATAGCAGGAATTAGTGCTGGAATTTTGGTGTTCATCCTCCTTCTCCTAGTTGTCATATTAATTG 2320
 747   D  R  V  V  K  I  A  G  I  S  A  G  I  L  V  F  I  L  L  L  V  V  I  L  I  V  773

2321 TAAAAAAGAGCAAACTTGCTAAAAAACGCAAAGATGCCATGGGGAATACCCGGCAGGAGATGACTCACATGGTGAATGCA 2400
 774    K  K  S  L  A  K  K  R  K  D  A  M  G  N  T  R  Q  E  M  T  H  M  V  N  A   800

2401 ATGGATCGAAGTTATGCTGATCAGAGCACTCTGCATGCAGAAGATCCTCTTTCCATCACCTTCATGGACCAACATAACTT 2480
 801   M  D  R  S  Y  A  D  Q  S  T  L  H  A  E  D  P  L  S  I  T  F  M  D  Q  H  N  F 827

2481 TAGTCCAAGATATGAGAACCACAGTGCTACAGCAGAGTCCAGTCGCCTTCTAGACGTACCTCGCTACCTCTGTGAGGGGA 2560
 827   S  P  R  Y  E  N  H  S  A  T  A  E  S  S  R  L  L  D  V  P  R  Y  L  C  E  G  T 853

2561 CGGAATCCCCTTACCAGACAGGACAGCTGCATCCAGCCATCAGGGTAGCTGATTTACTGCAGCACATTAATCTCATGAAG 2640
 854    E  S  P  Y  Q  T  G  Q  L  H  P  A  I  R  V  A  D  L  L  Q  H  I  N  L  M  K  880

2641 ACATCAGACAGCTATGGGTTCAAAGAGGAATATGAGAGCTTTTTTGAAGGACAGTCAGCATCTTGGGATGTAGCTAAAAA 2720
 881   T  S  D  S  Y  G  F  K  E  E  Y  E  S  F  F  E  G  Q  S  A  S  W  D  V  A  K  K 907

2721 AGATCAAAATAGAGCAAAAAACCGATATGGAAACATTATAGCATATGATCACTCCAGAGTGATTTTGCAACCCGTAGAGG 2800
 907   D  Q  N  R  A  K  N  R  Y  G  N  I  I  A  Y  D  H  S  R  V  I  L  Q  P  V  E  D 933

2801 ATGATCCTTCCTCAGATTATATTAATGCCAACTATATTGATGGCTACCAGAGACCAAGTCATTACATTGCAACCCAAGGT 2880
 934    D  P  S  S  D  Y  I  N  A  N  Y  I  D  G  Y  Q  R  P  S  H  Y  I  A  T  Q  G  960

2881 CCCGTTCATGAAACAGTGTATGATTTCTGGAGGATGATTTGGCAAGAACAATCTGCTTGCATTGTGATGGTTACAAATTT 2960
 961   P  V  H  E  T  V  Y  D  F  W  R  M  I  W  Q  E  Q  S  A  C  I  V  M  V  T  N  L 987

2961 AGTTGAGGTTGGCCGGGTTAAATGCTATAAATATTGGCCTGATGATACTGAAGTTTATGGTGACTTCAAAGTAACGTGTG 3040
 987   V  E  V  G  R  V  K  C  Y  K  Y  W  P  D  D  T  E  V  Y  G  D  F  K  V  T  C  V 1013

3041 TAGAAATGGAACCACTTGCTGAATATGTAGTTAGGACATTCACCCTGGAAAGGAGGGGGTACAATGAAATCCGTGAAGTT 3120
1014    E  M  E  P  L  A  E  Y  V  V  R  T  F  T  L  E  R  R  G  Y  N  E  I  R  E  V 1040

3121 AAACAGTTCCATTTCACCGGCTGGCCTGACCATGGAGTGCCCTACCATGCTACAGGGCTGCTTTCCTTTATCCGGCGAGT 3200
1041   K  Q  F  H  F  T  G  W  P  D  H  G  V  P  Y  H  A  T  G  L  L  S  F  I  R  R  V 1067
```

FIG.15C

```
3201  CAAGTTATCAAACCCTCCCAGTGCTGGCCCCATCGTTGTACATTGCAGTGCTGGTGCTGGACGAACTGGCTGCTACATTG  3280
1067   K  L  S  N  P  P  S  A  G  P  I  V  V  H  C  S  A  G  A  G  R  T  G  C  Y  I  V   1093

3281  TGATTGACATCATGCTAGACATGGCTGAAAGAGAGGGTGTTGTTGATATTTACAATTGTGTCAAAGCCTTAAGATCTCGG  3360
1094    I  D  I  M  L  D  M  A  E  R  E  G  V  V  D  I  Y  N  C  V  K  A  L  R  S  R    1120

3361  CGTATTAATATGGTCCAGACAGAGGAACAGTACATTTTTATTCATGATGCCATTTTAGAAGCCTGCTTATGTGGAGAAAC  3440
1121   R  I  N  M  V  Q  T  E  E  Q  Y  I  F  I  H  D  A  I  L  E  A  C  L  C  G  E  T   1147

3441  TGCCATACCTGTCTGTGAATTTAAAGCTGCCATATTTTGATATGATTAGAATAGACTCCCAGACTAACTCTTCACATCTCA  3520
1147   A  I  F  V  C  E  F  K  A  A  Y  F  D  M  I  R  I  D  S  Q  T  N  S  S  H  L  K   1173

3521  AGGATGAATTTCAGACTCTGAATTCAGTCACCCCTCGACTACAAGCTGAAGACTGCAGTATAGCGTGCCTGCCAAGGAAC  3600
1174    D  E  F  Q  T  L  N  S  V  T  P  R  L  Q  A  E  D  C  S  I  A  C  L  P  R  N    1200

3601  CATGACAAGAACCGTTTCATGGACATGCTGCCACCTGACAGATGTCTGCCTTTTTTAATTACAATTGATGGGGAGAGCAG  3680
1201   H  D  K  N  R  F  M  D  M  L  P  P  D  R  C  L  P  F  L  I  T  I  D  G  E  S  S   1227

3681  TAACTACATCAATGCTGCTCTTATGGACAGCTACAGGCAACCAGCTGCTTTCATCGTCACACAATACCCTCTGCCAAACA  3760
1227   N  Y  I  N  A  A  L  M  D  S  Y  R  Q  P  A  A  F  I  V  T  Q  Y  P  L  P  N  T   1253

3761  CTGTAAAAGACTTCTGGAGATTAGTGTATGATTATGGCTGTACCTCCATTGTGATGTTAAACGAAGTCGACTTGTCCCAG  3840
1254    V  K  D  F  W  R  L  V  Y  D  Y  G  C  T  S  I  V  M  L  N  E  V  D  L  S  Q    1280

3841  GGCTGCCCTCAGTACTGGCCAGAGGAAGGGATGCTACGATATGGCCCCATCCAAGTGGAATGTATGTCTTGTTCAATGGA  3920
1281   G  C  P  Q  Y  W  P  E  E  G  M  L  R  Y  G  P  I  Q  V  E  C  M  S  C  S  M  D   1307

3921  CTGTGATGTGATCAACCGGATTTTTAGGATATGCAATCTAACAAGACCACAGGAAGGTTATCTGATGGTGCAACAGTTTC  4000
1307   C  D  V  I  N  R  I  F  R  I  C  N  L  T  R  P  Q  E  G  Y  L  M  V  Q  Q  F  Q   1333

4001  AGTACCTAGGATGGGCTTCTCATCGAGAAGTGCCTGGATCCAAAAGGTCATTCTTGAAACTGATACTTCAGGTGGAAAAG  4080
1334    Y  L  G  W  A  S  H  R  E  V  P  G  S  K  R  S  F  L  K  L  I  L  Q  V  E  K    1360

4081  TGGCAGGAGGAATGCGAGGAAGGGAAGGCCGGACGATTATCCACTGCCTAAATGGTGGCGGCCGAAGTGGCATGTTCTG  4160
1361   W  Q  E  E  C  E  E  G  E  G  R  T  I  I  H  C  L  N  G  G  G  R  S  G  M  F  C   1387

4161  TGCTATAGGCATCGTTGTTGAAATGGTGAAACGGCAAAATGTTGTCGATGTTTTCCATGCAGTAAAGACACTGAGGAACA  4240
1387   A  I  G  I  V  V  E  M  V  K  R  Q  N  V  V  D  V  F  H  A  V  K  T  L  R  N  S   1413
```

FIG.15D

```
4241  GCAAGCCAAACATGGTGGAAGCCCCCGAGCAATACCGTTTCTGCTATGATGTAGCTTTGGAGTACCTGGAATCATCTTAG  4320
1414    K  P  N  M  V  E  A  P  E  Q  Y  R  F  C  Y  D  V  A  L  E  Y  L  E  S  S  *    1439
                                                                           SEQ. ID NO: 2
4321  TTGGGTGAGACTCTTTAAAGTGCATCCATGAAGAAACCTGTCCATCTATTGAGCCAGCAGCTGTTGTACCTGTTACACTT  4400
4401  GTGCAGAAAGATTTTAATGTGGGGGGTGGGAGACTTTTACATTTGAGAGGTAAAAGTATTTTTTTTATGAAGTTGTGTAT  4480
4481  CTTAATAAAAAGAACTGAATTAGTTTTTATTACTATATTAAAGCATCAACATTTCATGCCACATAAAATTATATTTAATA  4560
4561  AGAACCAGATTGAAATGAGAACGTATTGGTGTTTGTACAGTGAACATGCCACCTTTTTCCATGGTTTCAGGTAGTGCAGC  4640
4641  TACCACATGTT  4651
              SEQ. ID NO: 4
```

FIG.15E

| MCP7 | MDTTAAAALPAPVALLLLSPWPLLGSACCQPSAGGCCTFDDGPGACDYHQDLYDFEWVHVSAQEPHYLPPEMPQGSYMIV | 80 |
| hRPTPμ | --MRLGTC-ILG ---------TAAGET-L EPYST G S SEG N EQ NILKPTSD W S L L | 71 |
| MCP7 | DSSDHDPGEKARLQLPTMKENDTHCIDFSYLLYSQKGLNPCTLNILVRVNKGPLANPIMNVTGFTGRDWLRAELAVSTFW | 160 |
| hRPTPμ | NA GRPE QR H L QL     H FVS KSNSP L VYK N G   IS DPT T N   I | 151 |
| MCP7 | PNEYQVIFEAEVSGGRSGYIAIDDIQVLSYPCDKSPHFLRLGDVEVNAGQNATFQCIATGRDAVHNKLWLQRRNGEDIPV | 240 |
| hRPTPμ | F V-ITS HQ L EVK GH TRT   ICN   P   SI TVAGDR   GIDVR A L | 230 |
| MCP7 | AQTKNINHRRFAASFRLQEVIKTDQDLYRCVIQSERGSGVSNFAQLIVREPPRPIAPPQLGVGPTYLLIQLNANSIIGD | 320 |
| hRPTPμ | KEI VTSS I NVVNT R AGK MIRT G V I Y E V K V   AS A W   N | 310 |
| MCP7 | GPIILKEVEYRMTSGSWTETHAVNAPTYKLWHLDPDTEYEIRVLLTRPGEGGTGLPGPPLITRTKCAEPMRTPKTLKIAE | 400 |
| hRPTPμ | VAR CTA NDRQP DSTS IG     S       S A R     D   G RK EVV | 390 |
| MCP7 | IQARRIAVDMESLGYNITRCHTFNVTICYHYFRGHNE---SKADCLDMDPKAPQHVVNHLPPYINVSLKMILTNPEGRKES | 478 |
| hRPTPμ | VKS Q TIR PF V SY L VH C QV GQ QVREEVSW TENSH TITIN S   VL M | 470 |
| MCP7 | EETIIQTDEDVPCPVPVKSLQCTSFENKIFLMWKEPLDPNGIITQYEISYSSIRSFDPAVPVAGPPQTVSNLWMSTHHVF | 558 |
| hRPTPμ | QLV L A TEI ST E   QR TQTY V L   T KAVS   EIDLSNQSGR K G E FL | 550 |
| MCP7 | MHLHPGTIYQFFIRASTVKGFGPATAINVTINISAPTLPDYEGVDASLNETATITVLLRPAQAKGAPISAYQIVWEELH | 638 |
| hRPTPμ | PG Y ST A PAINQF K SM A -LETP Q DN V MK HSR VV   ER | 629 |
| MCP7 | PHRTKREAGAMECYQVPVTYQNAMSGCAPYYFAAELPPGNLPEPAPFTVGDNRTYQGFWNPPLAPRKGYNIYFQAMSSVE | 718 |
| hRPTPμ | R KTIEILK P IHF SLLNSQ     F ADS QAAQ   I KNYTLYSR   A RAN | 709 |

FIG.16A

```
                     **********
MCP7    KETKTQCVRIATKAATEEPEVIPDDPAKQTDRVVKIAGISAGILVFILLLLVVILIVKKSKLAKKRKDAMGNTRQEMTHMV    798
hRPTPμ  G   ID QV   GA-T KPVEE      HT      VI    LVIIFGVVM R            ET SS     V    788

MCP7    NAMDRSYADQSTLHAEDPLSITFMDQHNFSPRY----------ENHSATAESSRLLDVPRY-LCE                    852
hRPTPμ  S  E G -NCDEAF --   T LNG SVSSPSSFTMKTNTLSTSVPNSYYPD T TMASDT S VQSHT KKR          865

MCP7    GTESPYQTGQLHPAIRVADLLQHINLMKTSDSYGFKEEYESFFEGQSASMDVAKKDQNRAKNRYGNIIAYDHSRVILQPV      932
hRPTPμ  PADV                        TQ CAEG       P  S   E   M           R  TI            945

MCP7    EDDPSSDYINANYIDGYQRPSHYIATQGPVHETVYDFWRMIWQEQSACIVMVTNLVEVGRVKCYKYWPDDTEVYGDFKVT    1012
hRPTPμ  G TN   G    HN        MQ I    VHNTSI            C             IKI                 1025

MCP7    CVEMEPLAEYVVRTFTLERRGYNEIREVKQFHFTGWPDHGVPYHATGLLSFIRRVKLSNPPSAGPIVVHCSAGAGRTGCY    1092
hRPTPμ  LITL   I   AVK VH   IR                            GVQ SKS    L              F     1105

MCP7    IVIDIMLDWAEREGVVDIYNCVKALRSRRINMVQTEEQYIFIHDAILEACLQGETAIPVCEFKAAYFDMIRIDSQTNSSH    1172
hRPTPμ             RE   V     V            D SV ASQVRSL Y NKLP           Q               1185

MCP7    LKDEFQTLNSVTPRLQAEDCSTACLPRNHDKNRFMDMLPPDRCLPFLITIDGESSNYINAALMDSYRQPAAFIVTQYPLP    1252
hRPTPμ  I E R   M  T RV       L  E C I                    K  S       H                    1265

MCP7    NTVKDFWRLVYDYGCTSIVMLNEVDLSQCCPQYWPEEGMLRYGPIQVECMSCSMDCDVINRIFRICNLTRPQEGYLMVQQ    1332
hRPTPμ           L  H V D PAL   N VH H         FV ADLEE I S    YAA  D R                   1345

MCP7    FQYLGWASHREVPGSKRSFLKIILQVEKMQEECEGEGRTIIHCLNGGGRSGMFCAIGIVVEMVKRQNVVDVFHAVKTLR      1412
hRPTPμ  F   PMY DT V      R D    YNG P VV         T     S C  LRH RT                       1425

MCP7    NSKPNMVEAPEQYRFCYDVALEYLESS*                                                         1439
hRPTPμ  N    DLLD K    E       N G*                                                        1452
```

FIG.16B

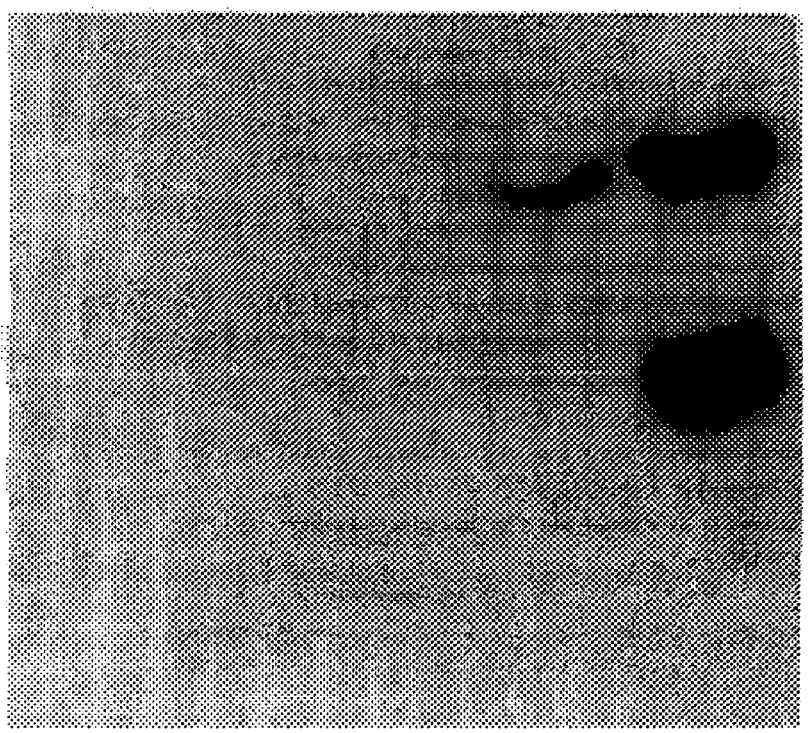
F I G. 22A

SEQUENCE LISTING

```
<160> NUMBER OF SEQ ID NOS: 13

<210> SEQ ID NO 1
<211> LENGTH: 1457
<212> TYPE: PRT
<213> ORGANISM: Mus musculus

<400> SEQUENCE: 1

Met Asp Val Ala Ala Ala Ala Leu Pro Ala Phe Val Ala Leu Trp Leu
 1               5                  10                  15

Leu Tyr Pro Trp Pro Leu Leu Gly Ser Ala Leu Gly Gln Phe Ser Ala
                20                  25                  30

Gly Gly Cys Thr Phe Asp Asp Gly Pro Gly Ala Cys Asp Tyr His Gln
            35                  40                  45

Asp Leu Tyr Asp Asp Phe Glu Trp Val His Val Ser Ala Gln Glu Pro
        50                  55                  60

His Tyr Leu Pro Pro Glu Met Pro Gln Gly Ser Tyr Met Val Val Asp
    65                  70                  75                  80

Ser Ser Asn His Asp Pro Gly Glu Lys Ala Arg Leu Gln Leu Pro Thr
                85                  90                  95
```

```
Met Lys Glu Asn Asp Thr His Cys Ile Asp Phe Ser Tyr Leu Leu Tyr
            100                 105                 110
Ser Gln Lys Gly Leu Asn Pro Gly Thr Leu Asn Ile Leu Val Arg Val
        115                 120                 125
Asn Lys Gly Pro Leu Ala Asn Pro Ile Trp Asn Val Thr Gly Phe Thr
    130                 135                 140
Gly Arg Asp Trp Leu Arg Ala Glu Leu Ala Val Ser Thr Phe Trp Pro
145                 150                 155                 160
Asn Glu Tyr Gln Val Ile Phe Glu Ala Glu Val Ser Gly Gly Arg Ser
                165                 170                 175
Gly Tyr Ile Ala Ile Asp Asp Ile Gln Val Leu Ser Tyr Pro Cys Asp
            180                 185                 190
Lys Ser Pro His Phe Leu Arg Leu Gly Asp Val Glu Val Asn Ala Gly
        195                 200                 205
Gln Asn Ala Thr Phe Gln Cys Ile Ala Thr Gly Arg Asp Ala Val His
    210                 215                 220
Asn Lys Leu Trp Leu Gln Arg Arg Asn Gly Glu Asp Ile Pro Val Ala
225                 230                 235                 240
Gln Thr Lys Asn Ile Asn His Arg Arg Phe Ala Ala Ser Phe Arg Leu
                245                 250                 255
Gln Glu Val Thr Lys Thr Asp Gln Asp Leu Tyr Arg Cys Val Thr Gln
            260                 265                 270
Ser Glu Arg Gly Ser Gly Val Ser Asn Phe Ala Gln Leu Ile Val Arg
        275                 280                 285
Glu Pro Pro Arg Pro Ile Ala Pro Pro Gln Leu Leu Gly Val Gly Pro
    290                 295                 300
Thr Tyr Leu Leu Ile Gln Leu Asn Ala Asn Ser Ile Ile Gly Asp Gly
305                 310                 315                 320
Pro Ile Ile Leu Lys Glu Val Glu Tyr Arg Met Thr Ser Gly Ser Trp
                325                 330                 335
Thr Glu Thr His Ala Val Asn Ala Pro Thr Tyr Lys Leu Trp His Leu
            340                 345                 350
Asp Pro Asp Thr Glu Tyr Glu Ile Arg Val Leu Leu Thr Arg Pro Gly
        355                 360                 365
Glu Gly Gly Thr Gly Leu Pro Gly Pro Pro Leu Ile Thr Arg Thr Lys
    370                 375                 380
Cys Ala Glu Pro Met Arg Thr Pro Lys Thr Leu Lys Ile Ala Glu Ile
385                 390                 395                 400
Gln Ala Arg Arg Ile Ala Val Asp Trp Glu Ser Leu Gly Tyr Asn Ile
                405                 410                 415
Thr Arg Cys His Thr Phe Asn Val Thr Ile Cys Tyr His Tyr Phe Arg
            420                 425                 430
Gly His Asn Glu Ser Arg Ala Asp Cys Leu Asp Met Asp Pro Lys Ala
        435                 440                 445
Pro Gln His Val Val Asn His Leu Pro Pro Tyr Thr Asn Val Ser Leu
    450                 455                 460
Lys Met Ile Leu Thr Asn Pro Glu Gly Arg Lys Glu Ser Glu Glu Thr
465                 470                 475                 480
Ile Ile Gln Thr Asp Glu Asp Val Pro Gly Pro Val Pro Val Lys Ser
                485                 490                 495
Leu Gln Gly Thr Ser Phe Glu Asn Lys Ile Phe Leu Asn Trp Lys Glu
            500                 505                 510
```

```
Pro Leu Glu Pro Asn Gly Ile Ile Thr Gln Tyr Glu Val Ser Tyr Ser
        515                 520                 525

Ser Ile Arg Ser Phe Asp Pro Ala Val Pro Val Ala Gly Pro Pro Gln
        530                 535                 540

Thr Val Ser Asn Leu Trp Asn Ser Thr His Val Phe Met His Leu
545                 550                 555                 560

His Pro Gly Thr Thr Tyr Gln Phe Phe Ile Arg Ala Ser Thr Val Lys
                565                 570                 575

Gly Phe Gly Pro Ala Thr Ala Ile Asn Val Thr Thr Asn Ile Ser Ala
                580                 585                 590

Pro Ser Leu Pro Asp Tyr Glu Gly Val Asp Ala Ser Leu Asn Glu Thr
        595                 600                 605

Ala Thr Thr Ile Thr Val Leu Leu Arg Pro Ala Gln Ala Lys Gly Ala
610                 615                 620

Pro Ile Ser Ala Tyr Gln Ile Val Glu Gln Leu His Pro His Arg
625                 630                 635                 640

Thr Lys Arg Glu Ala Gly Ala Met Glu Cys Tyr Gln Val Pro Val Thr
                645                 650                 655

Tyr Gln Asn Ala Leu Ser Gly Gly Ala Pro Tyr Tyr Phe Ala Ala Glu
                660                 665                 670

Leu Pro Pro Gly Asn Leu Pro Glu Pro Ala Pro Phe Thr Val Gly Asp
        675                 680                 685

Asn Arg Thr Tyr Lys Gly Phe Trp Asn Pro Pro Leu Ala Pro Arg Lys
        690                 695                 700

Gly Tyr Asn Ile Tyr Phe Gln Ala Met Ser Ser Val Glu Lys Glu Thr
705                 710                 715                 720

Lys Thr Gln Cys Val Arg Ile Ala Thr Lys Ala Ala Thr Glu Glu
                725                 730                 735

Pro Glu Val Ile Pro Asp Pro Ala Lys Gln Thr Asp Arg Val Val Lys
                740                 745                 750

Ile Ala Gly Ile Ser Ala Gly Ile Leu Val Phe Ile Leu Leu Leu
        755                 760                 765

Val Val Ile Val Ile Val Lys Lys Ser Lys Leu Ala Lys Lys Arg Lys
        770                 775                 780

Asp Ala Met Gly Asn Thr Arg Gln Glu Met Thr His Met Val Asn Ala
785                 790                 795                 800

Met Asp Arg Ser Tyr Ala Asp Gln Ser Thr Leu His Ala Glu Asp Pro
                805                 810                 815

Leu Ser Leu Thr Phe Met Asp Gln His Asn Phe Ser Pro Arg Leu Pro
                820                 825                 830

Asn Asp Pro Leu Val Pro Thr Ala Val Leu Asp Glu Asn His Ser Ala
        835                 840                 845

Thr Ala Glu Ser Ser Arg Leu Leu Asp Val Pro Arg Tyr Leu Cys Glu
850                 855                 860

Gly Thr Glu Ser Pro Tyr Gln Thr Gly Gln Leu His Pro Ala Ile Arg
865                 870                 875                 880

Val Ala Asp Leu Leu Gln His Ile Asn Leu Met Lys Thr Ser Asp Ser
                885                 890                 895

Tyr Gly Phe Lys Glu Glu Tyr Glu Ser Phe Phe Glu Gly Gln Ser Ala
                900                 905                 910

Ser Trp Asp Val Ala Lys Lys Asp Gln Asn Arg Ala Lys Asn Arg Tyr
        915                 920                 925

Gly Asn Ile Ile Ala Tyr Asp His Ser Arg Val Ile Leu Gln Pro Val
```

-continued

```
            930              935              940
Glu Asp Asp Pro Ser Ser Asp Tyr Ile Asn Ala Asn Tyr Ile Asp Ile
945              950              955              960

Trp Leu Tyr Arg Asp Gly Tyr Gln Arg Pro Ser His Tyr Ile Ala Thr
            965              970              975

Gln Gly Pro Val His Glu Thr Val Tyr Asp Phe Trp Arg Met Val Trp
            980              985              990

Gln Glu Gln Ser Ala Cys Ile Val Met Val Thr Asn Leu Val Glu Val
            995              1000             1005

Gly Arg Val Lys Cys Tyr Lys Tyr Trp Pro Asp Asp Thr Glu Val Tyr
    1010             1015             1020

Gly Asp Phe Lys Val Thr Cys Val Glu Met Glu Pro Leu Ala Glu Tyr
1025             1030             1035             1040

Val Val Arg Thr Phe Thr Leu Glu Arg Arg Gly Tyr Asn Glu Ile Arg
            1045             1050             1055

Glu Val Lys Gln Phe His Phe Thr Gly Trp Pro Asp His Gly Val Pro
            1060             1065             1070

Tyr His Ala Thr Gly Leu Leu Ser Phe Ile Arg Arg Val Lys Leu Ser
    1075             1080             1085

Asn Pro Pro Ser Ala Gly Pro Ile Val Val His Cys Ser Ala Gly Ala
    1090             1095             1100

Gly Arg Thr Gly Cys Tyr Ile Val Ile Asp Ile Met Leu Asp Met Ala
1105             1110             1115             1120

Glu Arg Glu Gly Val Val Asp Ile Tyr Asn Cys Val Lys Ala Leu Arg
            1125             1130             1135

Ser Arg Arg Ile Asn Met Val Gln Thr Glu Glu Gln Tyr Ile Phe Ile
        1140             1145             1150

His Asp Ala Ile Leu Glu Ala Cys Leu Cys Gly Glu Thr Ala Ile Pro
        1155             1160             1165

Val Cys Glu Phe Lys Ala Ala Tyr Phe Asp Met Ile Arg Ile Asp Ser
    1170             1175             1180

Gln Thr Asn Ser Ser His Leu Lys Asp Glu Phe Gln Thr Leu Asn Ser
1185             1190             1195             1200

Val Thr Pro Arg Leu Gln Ala Glu Asp Cys Ser Ile Ala Cys Leu Pro
            1205             1210             1215

Arg Asn His Asp Lys Asn Arg Phe Met Asp Met Leu Pro Pro Asp Arg
        1220             1225             1230

Cys Leu Pro Phe Leu Ile Thr Ile Asp Gly Glu Ser Ser Asn Tyr Ile
    1235             1240             1245

Asn Ala Ala Leu Met Asp Ser Tyr Arg Gln Pro Ala Ala Phe Ile Val
    1250             1255             1260

Thr Gln Tyr Pro Leu Pro Asn Thr Val Lys Asp Phe Trp Arg Leu Val
1265             1270             1275             1280

Tyr Asp Tyr Gly Cys Thr Ser Ile Val Met Leu Asn Glu Val Asp Leu
            1285             1290             1295

Ser Gln Gly Cys Pro Gln Tyr Trp Pro Glu Glu Gly Met Leu Arg Tyr
        1300             1305             1310

Gly Pro Ile Gln Val Glu Cys Met Ser Cys Ser Met Asp Cys Asp Val
    1315             1320             1325

Ile Asn Arg Ile Phe Arg Ile Cys Asn Leu Thr Arg Pro Gln Glu Gly
    1330             1335             1340

Tyr Leu Met Val Gln Gln Phe Gln Tyr Leu Gly Trp Ala Ser His Arg
1345             1350             1355             1360
```

```
Glu Val Pro Gly Ser Lys Arg Ser Phe Leu Lys Leu Ile Leu Gln Val
            1365                1370                1375
Glu Lys Trp Gln Glu Glu Cys Glu Glu Gly Glu Gly Arg Thr Ile Ile
            1380                1385                1390
His Cys Leu Asn Gly Gly Arg Ser Gly Met Phe Cys Ala Ile Gly
            1395                1400                1405
Ile Val Val Glu Met Val Lys Arg Gln Asn Val Asp Val Phe His
    1410                1415                1420
Ala Val Lys Thr Leu Arg Asn Ser Lys Pro Asn Met Val Glu Ala Pro
1425                1430                1435                1440
Glu Gln Tyr Arg Phe Cys Tyr Asp Val Ala Leu Glu Tyr Leu Glu Ser
            1445                1450                1455
Ser

<210> SEQ ID NO 2
<211> LENGTH: 1439
<212> TYPE: PRT
<213> ORGANISM: Homo sapiens

<400> SEQUENCE: 2

Met Asp Thr Thr Ala Ala Ala Leu Pro Ala Phe Val Ala Leu Leu
1               5                   10                  15
Leu Leu Ser Pro Trp Pro Leu Leu Gly Ser Ala Gln Gly Gln Phe Ser
            20                  25                  30
Ala Gly Gly Cys Thr Phe Asp Asp Gly Pro Gly Ala Cys Asp Tyr His
            35                  40                  45
Gln Asp Leu Tyr Asp Asp Phe Glu Trp Val His Val Ser Ala Gln Glu
        50                  55                  60
Pro His Tyr Leu Pro Pro Glu Met Pro Gln Gly Ser Tyr Met Ile Val
65                  70                  75                  80
Asp Ser Ser Asp His Asp Pro Gly Glu Lys Ala Arg Leu Gln Leu Pro
                85                  90                  95
Thr Met Lys Glu Asn Asp Thr His Cys Ile Asp Phe Ser Tyr Leu Leu
            100                 105                 110
Tyr Ser Gln Lys Gly Leu Asn Pro Gly Thr Leu Asn Ile Leu Val Arg
        115                 120                 125
Val Asn Lys Gly Pro Leu Ala Asn Pro Ile Trp Asn Val Thr Gly Phe
130                 135                 140
Thr Gly Arg Asp Trp Leu Arg Ala Glu Leu Ala Val Ser Thr Phe Trp
145                 150                 155                 160
Pro Asn Glu Tyr Gln Val Ile Phe Glu Ala Glu Val Ser Gly Gly Arg
                165                 170                 175
Ser Gly Tyr Ile Ala Ile Asp Asp Ile Gln Val Leu Ser Tyr Pro Cys
            180                 185                 190
Asp Lys Ser Pro His Phe Leu Arg Leu Gly Asp Val Glu Val Asn Ala
        195                 200                 205
Gly Gln Asn Ala Thr Phe Gln Cys Ile Ala Thr Gly Arg Asp Ala Val
    210                 215                 220
His Asn Lys Leu Trp Leu Gln Arg Arg Asn Gly Glu Asp Ile Pro Val
225                 230                 235                 240
Ala Gln Thr Lys Asn Ile Asn His Arg Arg Phe Ala Ala Ser Phe Arg
                245                 250                 255
Leu Gln Glu Val Thr Lys Thr Asp Gln Asp Leu Tyr Arg Cys Val Thr
            260                 265                 270
```

```
Gln Ser Glu Arg Gly Ser Gly Val Ser Asn Phe Ala Gln Leu Ile Val
            275                 280                 285

Arg Glu Pro Pro Arg Pro Ile Ala Pro Pro Gln Leu Leu Gly Val Gly
            290                 295                 300

Pro Thr Tyr Leu Leu Ile Gln Leu Asn Ala Asn Ser Ile Ile Gly Asp
305                 310                 315                 320

Gly Pro Ile Ile Leu Lys Glu Val Glu Tyr Arg Met Thr Ser Gly Ser
                325                 330                 335

Trp Thr Glu Thr His Ala Val Asn Ala Pro Thr Tyr Lys Leu Trp His
            340                 345                 350

Leu Asp Pro Asp Thr Glu Tyr Glu Ile Arg Val Leu Leu Thr Arg Pro
            355                 360                 365

Gly Glu Gly Gly Thr Gly Leu Pro Gly Pro Pro Leu Ile Thr Arg Thr
            370                 375                 380

Lys Cys Ala Glu Pro Met Arg Thr Pro Lys Thr Leu Lys Ile Ala Glu
385                 390                 395                 400

Ile Gln Ala Arg Arg Ile Ala Val Asp Trp Glu Ser Leu Gly Tyr Asn
                405                 410                 415

Ile Thr Arg Cys His Thr Phe Asn Val Thr Ile Cys Tyr His Tyr Phe
            420                 425                 430

Arg Gly His Asn Glu Ser Lys Ala Asp Cys Leu Asp Met Asp Pro Lys
            435                 440                 445

Ala Pro Gln His Val Val Asn His Leu Pro Pro Tyr Thr Asn Val Ser
450                 455                 460

Leu Lys Met Ile Leu Thr Asn Pro Glu Gly Arg Lys Glu Ser Glu Glu
465                 470                 475                 480

Thr Ile Ile Gln Thr Asp Glu Asp Val Pro Gly Pro Val Pro Val Lys
                485                 490                 495

Ser Leu Gln Gly Thr Ser Phe Glu Asn Lys Ile Phe Leu Asn Trp Lys
            500                 505                 510

Glu Pro Leu Asp Pro Asn Gly Ile Ile Thr Gln Tyr Glu Ile Ser Tyr
            515                 520                 525

Ser Ser Ile Arg Ser Phe Asp Pro Ala Val Pro Val Ala Gly Pro Pro
530                 535                 540

Gln Thr Val Ser Asn Leu Trp Asn Ser Thr His His Val Phe Met His
545                 550                 555                 560

Leu His Pro Gly Thr Thr Tyr Gln Phe Phe Ile Arg Ala Ser Thr Val
            565                 570                 575

Lys Gly Phe Gly Pro Ala Thr Ala Ile Asn Val Thr Thr Asn Ile Ser
            580                 585                 590

Ala Pro Thr Leu Pro Asp Tyr Glu Gly Val Asp Ala Ser Leu Asn Glu
            595                 600                 605

Thr Ala Thr Thr Ile Thr Val Leu Leu Arg Pro Ala Gln Ala Lys Gly
            610                 615                 620

Ala Pro Ile Ser Ala Tyr Gln Ile Val Val Glu Glu Leu His Pro His
625                 630                 635                 640

Arg Thr Lys Arg Glu Ala Gly Ala Met Glu Cys Tyr Gln Val Pro Val
                645                 650                 655

Thr Tyr Gln Asn Ala Met Ser Gly Gly Ala Pro Tyr Tyr Phe Ala Ala
            660                 665                 670

Glu Leu Pro Pro Gly Asn Leu Pro Glu Pro Ala Pro Phe Thr Val Gly
            675                 680                 685
```

-continued

```
Asp Asn Arg Thr Tyr Gln Gly Phe Trp Asn Pro Pro Leu Ala Pro Arg
690                 695                 700
Lys Gly Tyr Asn Ile Tyr Phe Gln Ala Met Ser Ser Val Glu Lys Glu
705                 710                 715                 720
Thr Lys Thr Gln Cys Val Arg Ile Ala Thr Lys Ala Ala Thr Glu Glu
                725                 730                 735
Pro Glu Val Ile Pro Asp Pro Ala Lys Gln Thr Asp Arg Val Lys
            740                 745                 750
Ile Ala Gly Ile Ser Ala Gly Ile Leu Val Phe Ile Leu Leu Leu
            755                 760                 765
Val Val Ile Leu Ile Val Lys Lys Ser Lys Leu Ala Lys Lys Arg Lys
770                 775                 780
Asp Ala Met Gly Asn Thr Arg Gln Glu Met Thr His Met Val Asn Ala
785                 790                 795                 800
Met Asp Arg Ser Tyr Ala Asp Gln Ser Thr Leu His Ala Glu Asp Pro
                805                 810                 815
Leu Ser Ile Thr Phe Met Asp Gln His Asn Phe Ser Pro Arg Tyr Glu
            820                 825                 830
Asn His Ser Ala Thr Ala Glu Ser Ser Arg Leu Leu Asp Val Pro Arg
835                 840                 845
Tyr Leu Cys Glu Gly Thr Glu Ser Pro Tyr Gln Thr Gly Gln Leu His
850                 855                 860
Pro Ala Ile Arg Val Ala Asp Leu Leu Gln His Ile Asn Leu Met Lys
865                 870                 875                 880
Thr Ser Asp Ser Tyr Gly Phe Lys Glu Glu Tyr Glu Ser Phe Phe Glu
                885                 890                 895
Gly Gln Ser Ala Ser Trp Asp Val Ala Lys Lys Asp Gln Asn Arg Ala
            900                 905                 910
Lys Asn Arg Tyr Gly Asn Ile Ile Ala Tyr Asp His Ser Arg Val Ile
            915                 920                 925
Leu Gln Pro Val Glu Asp Asp Pro Ser Ser Asp Tyr Ile Asn Ala Asn
930                 935                 940
Tyr Ile Asp Gly Tyr Gln Arg Pro Ser His Tyr Ile Ala Thr Gln Gly
945                 950                 955                 960
Pro Val His Glu Thr Val Tyr Asp Phe Trp Arg Met Ile Trp Gln Glu
                965                 970                 975
Gln Ser Ala Cys Ile Val Met Val Thr Asn Leu Val Glu Val Gly Arg
            980                 985                 990
Val Lys Cys Tyr Lys Tyr Trp Pro Asp Asp Thr Glu Val Tyr Gly Asp
            995                 1000                1005
Phe Lys Val Thr Cys Val Glu Met Glu Pro Leu Ala Glu Tyr Val Val
    1010                1015                1020
Arg Thr Phe Thr Leu Glu Arg Arg Gly Tyr Asn Glu Ile Arg Glu Val
1025                1030                1035                1040
Lys Gln Phe His Phe Thr Gly Trp Pro Asp His Gly Val Pro Tyr His
                1045                1050                1055
Ala Thr Gly Leu Leu Ser Phe Ile Arg Arg Val Lys Leu Ser Asn Pro
            1060                1065                1070
Pro Ser Ala Gly Pro Ile Val Val His Cys Ser Ala Gly Ala Gly Arg
            1075                1080                1085
Thr Gly Cys Tyr Ile Val Ile Asp Ile Met Leu Asp Met Ala Glu Arg
    1090                1095                1100
Glu Gly Val Val Asp Ile Tyr Asn Cys Val Lys Ala Leu Arg Ser Arg
```

-continued

```
                1105                1110                1115                1120
         Arg Ile Asn Met Val Gln Thr Glu Glu Gln Tyr Ile Phe Ile His Asp
                     1125                1130                1135
         Ala Ile Leu Glu Ala Cys Leu Cys Gly Glu Thr Ala Ile Pro Val Cys
                     1140                1145                1150
         Glu Phe Lys Ala Ala Tyr Phe Asp Met Ile Arg Ile Asp Ser Gln Thr
                     1155                1160                1165
         Asn Ser Ser His Leu Lys Asp Glu Phe Gln Thr Leu Asn Ser Val Thr
                     1170                1175                1180
         Pro Arg Leu Gln Ala Glu Asp Cys Ser Ile Ala Cys Leu Pro Arg Asn
         1185                1190                1195                1200
         His Asp Lys Asn Arg Phe Met Asp Met Leu Pro Pro Asp Arg Cys Leu
                     1205                1210                1215
         Pro Phe Leu Ile Thr Ile Asp Gly Glu Ser Ser Asn Tyr Ile Asn Ala
                     1220                1225                1230
         Ala Leu Met Asp Ser Tyr Arg Gln Pro Ala Ala Phe Ile Val Thr Gln
                     1235                1240                1245
         Tyr Pro Leu Pro Asn Thr Val Lys Asp Phe Trp Arg Leu Val Tyr Asp
                     1250                1255                1260
         Tyr Gly Cys Thr Ser Ile Val Met Leu Asn Glu Val Asp Leu Ser Gln
         1265                1270                1275                1280
         Gly Cys Pro Gln Tyr Trp Pro Glu Glu Gly Met Leu Arg Tyr Gly Pro
                     1285                1290                1295
         Ile Gln Val Glu Cys Met Ser Cys Ser Met Asp Cys Asp Val Ile Asn
                     1300                1305                1310
         Arg Ile Phe Arg Ile Cys Asn Leu Thr Arg Pro Gln Glu Gly Tyr Leu
                     1315                1320                1325
         Met Val Gln Gln Phe Gln Tyr Leu Gly Trp Ala Ser His Arg Glu Val
                     1330                1335                1340
         Pro Gly Ser Lys Arg Ser Phe Leu Lys Leu Ile Leu Gln Val Glu Lys
         1345                1350                1355                1360
         Trp Gln Glu Glu Trp Lys Glu Gly Glu Gly Arg Thr Ile Ile His Cys
                     1365                1370                1375
         Leu Asn Gly Gly Gly Arg Ser Gly Met Phe Cys Ala Ile Gly Ile Val
                     1380                1385                1390
         Val Glu Met Val Lys Arg Gln Asn Val Val Asp Val Phe His Ala Val
                     1395                1400                1405
         Lys Thr Leu Arg Asn Ser Lys Pro Asn Met Val Glu Ala Pro Glu Gln
             1410                1415                1420
         Tyr Arg Phe Cys Tyr Asp Val Ala Leu Glu Tyr Leu Glu Ser Ser
         1425                1430                1435

<210> SEQ ID NO 3
<211> LENGTH: 4374
<212> TYPE: DNA
<213> ORGANISM: Mus musculus
<220> FEATURE:
<221> NAME/KEY: CDS
<222> LOCATION: (1)..(4371)

<400> SEQUENCE: 3 atg gat gtg gcg gcc gct gcg ttg cct gct ttt gta gct ctc tgg ctt        48
Met Asp Val Ala Ala Ala Ala Leu Pro Ala Phe Val Ala Leu Trp Leu
1               5                   10                  15 ctg tac ccg tgg cct ctc ctg ggg tcg gcc ctt ggc cag ttc tca gca        96
Leu Tyr Pro Trp Pro Leu Leu Gly Ser Ala Leu Gly Gln Phe Ser Ala
```

```
                    20                  25                  30
ggt ggc tgt act ttt gat gat ggg cca ggg gct tgt gac tac cac cag    144
Gly Gly Cys Thr Phe Asp Asp Gly Pro Gly Ala Cys Asp Tyr His Gln
            35                  40                  45 gat tta tac gat gac ttt gag tgg gtc cat gtc agt gcg cag gaa cct    192
Asp Leu Tyr Asp Asp Phe Glu Trp Val His Val Ser Ala Gln Glu Pro
 50                  55                  60 cat tac ctg ccc ccc gaa atg cct caa ggt tcc tat atg gtt gtg gac    240
His Tyr Leu Pro Pro Glu Met Pro Gln Gly Ser Tyr Met Val Val Asp
 65                  70                  75                  80 tcc tca aat cat gat cct gga gaa aaa gcc aga ctt cag ctg cct acc    288
Ser Ser Asn His Asp Pro Gly Glu Lys Ala Arg Leu Gln Leu Pro Thr
                85                  90                  95 atg aag gag aat gac acc cac tgc att gat ttc agt tac ctg tta tat    336
Met Lys Glu Asn Asp Thr His Cys Ile Asp Phe Ser Tyr Leu Leu Tyr
            100                 105                 110 agc cag aag ggg ttg aac cct ggc act ttg aat atc cta gtt agg gtg    384
Ser Gln Lys Gly Leu Asn Pro Gly Thr Leu Asn Ile Leu Val Arg Val
        115                 120                 125 aat aaa gga cct ctt gct aat cca att tgg aat gta act gga ttc act    432
Asn Lys Gly Pro Leu Ala Asn Pro Ile Trp Asn Val Thr Gly Phe Thr
    130                 135                 140 ggt cgt gat tgg ctt cgg gct gaa cta gct gtg agc acc ttt tgg ccc    480
Gly Arg Asp Trp Leu Arg Ala Glu Leu Ala Val Ser Thr Phe Trp Pro
145                 150                 155                 160 aat gaa tac cag gta ata ttt gaa gct gaa gtc tca gga ggg aga agt    528
Asn Glu Tyr Gln Val Ile Phe Glu Ala Glu Val Ser Gly Gly Arg Ser
                165                 170                 175 ggt tat att gcc att gat gac atc caa gtc ctg agt tat cct tgc gat    576
Gly Tyr Ile Ala Ile Asp Asp Ile Gln Val Leu Ser Tyr Pro Cys Asp
            180                 185                 190 aaa tct cct cat ttt ctc cgc ctt ggt gat gtg gag gtc aat gct ggg    624
Lys Ser Pro His Phe Leu Arg Leu Gly Asp Val Glu Val Asn Ala Gly
        195                 200                 205 cag aat gct aca ttt cag tgc att gct aca ggg aga gat gct gtg cat    672
Gln Asn Ala Thr Phe Gln Cys Ile Ala Thr Gly Arg Asp Ala Val His
    210                 215                 220 aac aag tta tgg ctg cag aga cgc aat gga gaa gac ata ccc gta gcc    720
Asn Lys Leu Trp Leu Gln Arg Arg Asn Gly Glu Asp Ile Pro Val Ala
225                 230                 235                 240 cag act aag aac ata aat cac aga aga ttt gct gcc tct ttc aga ttg    768
Gln Thr Lys Asn Ile Asn His Arg Arg Phe Ala Ala Ser Phe Arg Leu
                245                 250                 255 caa gaa gtg aca aaa act gac cag gat ttg tac cgc tgc gta act cag    816
Gln Glu Val Thr Lys Thr Asp Gln Asp Leu Tyr Arg Cys Val Thr Gln
            260                 265                 270 tca gaa cga ggt tct ggg gtt tcc aat ttt gct caa ctc att gtg aga    864
Ser Glu Arg Gly Ser Gly Val Ser Asn Phe Ala Gln Leu Ile Val Arg
        275                 280                 285 gaa cca cct aga ccc att gct cct ccc cag ctg ctt ggt gtt ggg cct    912
Glu Pro Pro Arg Pro Ile Ala Pro Pro Gln Leu Leu Gly Val Gly Pro
    290                 295                 300 act tac ttg ctg atc caa cta aat gcc aac tct att att ggc gat ggc    960
Thr Tyr Leu Leu Ile Gln Leu Asn Ala Asn Ser Ile Ile Gly Asp Gly
305                 310                 315                 320 ccc atc atc ctg aaa gaa gta gag tat cga atg aca tca gga tct tgg   1008
Pro Ile Ile Leu Lys Glu Val Glu Tyr Arg Met Thr Ser Gly Ser Trp
                325                 330                 335 aca gaa acc cat gca gtc aac gca cca aca tat aag ttg tgg cat tta   1056
```

```
                Thr Glu Thr His Ala Val Asn Ala Pro Thr Tyr Lys Leu Trp His Leu
                            340                 345                 350 gac cca gat aca gaa tac gag atc cgc gtc ctg ctt acc aga cct ggc        1104
Asp Pro Asp Thr Glu Tyr Glu Ile Arg Val Leu Leu Thr Arg Pro Gly
            355                 360                 365 gaa ggg gga act ggg ctg cca gga cca cca ctg atc act aga acg aag        1152
Glu Gly Gly Thr Gly Leu Pro Gly Pro Pro Leu Ile Thr Arg Thr Lys
370                 375                 380 tgt gca gaa cct atg cgg aca cca aag act tta aag att gct gaa atc        1200
Cys Ala Glu Pro Met Arg Thr Pro Lys Thr Leu Lys Ile Ala Glu Ile
385                 390                 395                 400 cag gca agg cgc att gca gtg gac tgg gag tcc ttg ggc tac aac atc        1248
Gln Ala Arg Arg Ile Ala Val Asp Trp Glu Ser Leu Gly Tyr Asn Ile
                405                 410                 415 act cgt tgc cac act ttc aac gtc act atc tgc tac cat tac ttc cgt        1296
Thr Arg Cys His Thr Phe Asn Val Thr Ile Cys Tyr His Tyr Phe Arg
                420                 425                 430 ggc cac aat gag agc agg gca gac tgc ttg gac atg gac ccc aaa gcc        1344
Gly His Asn Glu Ser Arg Ala Asp Cys Leu Asp Met Asp Pro Lys Ala
            435                 440                 445 cct cag cat gtt gtg aac cat ctg cca cct tac aca aat gtc agc ctc        1392
Pro Gln His Val Val Asn His Leu Pro Pro Tyr Thr Asn Val Ser Leu
        450                 455                 460 aag atg atc cta acc aac cca gag gga agg aag gag agc gaa gag aca        1440
Lys Met Ile Leu Thr Asn Pro Glu Gly Arg Lys Glu Ser Glu Glu Thr
465                 470                 475                 480 atc atc caa act gat gaa gat gtg ccc ggg cct gtg cca gtc aaa tcc        1488
Ile Ile Gln Thr Asp Glu Asp Val Pro Gly Pro Val Pro Val Lys Ser
                485                 490                 495 ctc caa gga aca tcc ttt gaa aac aag atc ttc ctg aac tgg aaa gag        1536
Leu Gln Gly Thr Ser Phe Glu Asn Lys Ile Phe Leu Asn Trp Lys Glu
            500                 505                 510 cca ctg gaa ccg aat gga att atc act cag tat gag gtg agc tat agc        1584
Pro Leu Glu Pro Asn Gly Ile Ile Thr Gln Tyr Glu Val Ser Tyr Ser
        515                 520                 525 agc ata aga tca ttt gac cct gct gtt cca gtg gct ggg ccc cca cag        1632
Ser Ile Arg Ser Phe Asp Pro Ala Val Pro Val Ala Gly Pro Pro Gln
530                 535                 540 act gta tca aat tta tgg aat agt aca cac cat gta ttt atg cat ctt        1680
Thr Val Ser Asn Leu Trp Asn Ser Thr His His Val Phe Met His Leu
545                 550                 555                 560 cac cct gga acc acc tac cag ttt ttt ata aga gcc agc act gtc aaa        1728
His Pro Gly Thr Thr Tyr Gln Phe Phe Ile Arg Ala Ser Thr Val Lys
                565                 570                 575 ggc ttt gga cca gca aca gcc atc aat gtg acc aca aat atc tca gct        1776
Gly Phe Gly Pro Ala Thr Ala Ile Asn Val Thr Thr Asn Ile Ser Ala
            580                 585                 590 cca agc tta cct gac tat gaa gga gtt gat gcc tct ctg aat gaa act        1824
Pro Ser Leu Pro Asp Tyr Glu Gly Val Asp Ala Ser Leu Asn Glu Thr
        595                 600                 605 gcc acc acc atc aca gta cta ttg agg cct gca caa gcc aaa ggt gct        1872
Ala Thr Thr Ile Thr Val Leu Leu Arg Pro Ala Gln Ala Lys Gly Ala
610                 615                 620 cct atc agt gct tat caa att gtt gtg gag cag cta cac cca cat cga        1920
Pro Ile Ser Ala Tyr Gln Ile Val Val Glu Gln Leu His Pro His Arg
625                 630                 635                 640 acg aag cgt gaa gca ggg gcc atg gaa tgc tac cag gta ccg gtt aca        1968
Thr Lys Arg Glu Ala Gly Ala Met Glu Cys Tyr Gln Val Pro Val Thr
                645                 650                 655
```

```
                                                            -continued tac cag aac gcc cta agt ggg ggc gcg ccc tat tac ttt gcc gca gaa    2016
Tyr Gln Asn Ala Leu Ser Gly Gly Ala Pro Tyr Tyr Phe Ala Ala Glu
            660                 665                 670 ctt ccc cct ggg aat ctt ccc gag cct gct ccc ttc acc gtg ggt gac    2064
Leu Pro Pro Gly Asn Leu Pro Glu Pro Ala Pro Phe Thr Val Gly Asp
675                 680                 685 aac cgg acc tat aaa ggc ttt tgg aac cct ccc ctg gcc ccc cgc aaa    2112
Asn Arg Thr Tyr Lys Gly Phe Trp Asn Pro Pro Leu Ala Pro Arg Lys
690                 695                 700 gga tac aac atc tat ttc caa gcg atg agc agt gtg gag aag gaa act    2160
Gly Tyr Asn Ile Tyr Phe Gln Ala Met Ser Ser Val Glu Lys Glu Thr
705                 710                 715                 720 aaa acc caa tgt gta cga att gct aca aaa gca gca gca aca gaa gaa    2208
Lys Thr Gln Cys Val Arg Ile Ala Thr Lys Ala Ala Ala Thr Glu Glu
                725                 730                 735 cca gaa gtg atc cca gac ccg gca aag cag aca gac aga gtg gtg aaa    2256
Pro Glu Val Ile Pro Asp Pro Ala Lys Gln Thr Asp Arg Val Val Lys
            740                 745                 750 atc gcg ggc atc agt gct ggc atc cta gtg ttc atc ctt ctc ctg ctg    2304
Ile Ala Gly Ile Ser Ala Gly Ile Leu Val Phe Ile Leu Leu Leu Leu
        755                 760                 765 gtt gtc ata gta att gtg aaa aag agc aag ctt gct aag aag cgc aaa    2352
Val Val Ile Val Ile Val Lys Lys Ser Lys Leu Ala Lys Lys Arg Lys
    770                 775                 780 gat gca atg ggg aac aca cgt cag gag atg acc cac atg gtg aat gct    2400
Asp Ala Met Gly Asn Thr Arg Gln Glu Met Thr His Met Val Asn Ala
785                 790                 795                 800 atg gac cga agt tat gct gac cag agc acc ctg cat gca gaa gac ccc    2448
Met Asp Arg Ser Tyr Ala Asp Gln Ser Thr Leu His Ala Glu Asp Pro
                805                 810                 815 ctt tcc ctc acc ttc atg gac caa cat aac ttc agt cca aga ttg ccc    2496
Leu Ser Leu Thr Phe Met Asp Gln His Asn Phe Ser Pro Arg Leu Pro
            820                 825                 830 aat gat cca ctt gtg ccg act gcc gtg tta gat gag aac cac agt gcc    2544
Asn Asp Pro Leu Val Pro Thr Ala Val Leu Asp Glu Asn His Ser Ala
        835                 840                 845 aca gca gag tct agt cgt ctc ctg gat gtt cct cga tac ctc tgc gaa    2592
Thr Ala Glu Ser Ser Arg Leu Leu Asp Val Pro Arg Tyr Leu Cys Glu
    850                 855                 860 ggg aca gag tcc cct tat cag aca gga cag ctg cac cca gcc atc agg    2640
Gly Thr Glu Ser Pro Tyr Gln Thr Gly Gln Leu His Pro Ala Ile Arg
865                 870                 875                 880 gtg gcc gac tta ctg cag cac att aac ctc atg aag aca tca gac agc    2688
Val Ala Asp Leu Leu Gln His Ile Asn Leu Met Lys Thr Ser Asp Ser
                885                 890                 895 tat ggg ttc aaa gag gaa tac gag agc ttc ttt gaa ggc cag tca gcc    2736
Tyr Gly Phe Lys Glu Glu Tyr Glu Ser Phe Phe Glu Gly Gln Ser Ala
            900                 905                 910 tct tgg gat gtg gct aaa aag gat caa aac aga gca aag aac cga tac    2784
Ser Trp Asp Val Ala Lys Lys Asp Gln Asn Arg Ala Lys Asn Arg Tyr
        915                 920                 925 gga aac att atc gca tat gat cac tcc aga gtc atc ctg caa cct gtg    2832
Gly Asn Ile Ile Ala Tyr Asp His Ser Arg Val Ile Leu Gln Pro Val
    930                 935                 940 gaa gat gac cct tct tca gat tac att aat gcc aac tac atc gac att    2880
Glu Asp Asp Pro Ser Ser Asp Tyr Ile Asn Ala Asn Tyr Ile Asp Ile
945                 950                 955                 960 tgg ctg tac agg gat ggc tac cag aga cca agc cac tac att gca act    2928
Trp Leu Tyr Arg Asp Gly Tyr Gln Arg Pro Ser His Tyr Ile Ala Thr
                965                 970                 975
```

-continued

| | |
|---|---|
| caa ggc cca gtt cat gaa acc gta tat gat ttt tgg agg atg gtg tgg<br>Gln Gly Pro Val His Glu Thr Val Tyr Asp Phe Trp Arg Met Val Trp<br>        980                  985                  990 | 2976 |
| caa gag cag tct gcc tgt att gtg atg gtc act aat tta gtg gaa gtt<br>Gln Glu Gln Ser Ala Cys Ile Val Met Val Thr Asn Leu Val Glu Val<br>    995                  1000                1005 | 3024 |
| ggc cgg gtg aaa tgc tat aaa tat tgg cct gat gat act gag gtt tat<br>Gly Arg Val Lys Cys Tyr Lys Tyr Trp Pro Asp Asp Thr Glu Val Tyr<br>1010                1015                1020 | 3072 |
| ggt gac ttc aaa gtc acc tgc gta gaa atg gag cca ctt gct gag tat<br>Gly Asp Phe Lys Val Thr Cys Val Glu Met Glu Pro Leu Ala Glu Tyr<br>1025                1030                1035                1040 | 3120 |
| gtc gtt agg aca ttc acc ttg gaa agg agg ggc tat aat gaa atc cgt<br>Val Val Arg Thr Phe Thr Leu Glu Arg Arg Gly Tyr Asn Glu Ile Arg<br>                1045                1050                1055 | 3168 |
| gaa gtc aaa cag ttc cac ttc act ggc tgg cct gac cat ggt gtt cca<br>Glu Val Lys Gln Phe His Phe Thr Gly Trp Pro Asp His Gly Val Pro<br>            1060                1065                1070 | 3216 |
| tac cac gca aca ggg ctc ctg tca ttt atc cgg aga gtc aag cta tct<br>Tyr His Ala Thr Gly Leu Leu Ser Phe Ile Arg Arg Val Lys Leu Ser<br>1075                1080                1085 | 3264 |
| aac cct ccc agt gct ggg ccc att gtc gta cac tgc agt gct ggt gct<br>Asn Pro Pro Ser Ala Gly Pro Ile Val Val His Cys Ser Ala Gly Ala<br>    1090                  1095                1100 | 3312 |
| ggg cgc aca ggc tgt tac att gtt att gac ata atg ctg gac atg gct<br>Gly Arg Thr Gly Cys Tyr Ile Val Ile Asp Ile Met Leu Asp Met Ala<br>1105                1110                1115                1120 | 3360 |
| gaa aga gag ggt gtg gtt gac atc tac aac tgt gtg aaa gcc tta cga<br>Glu Arg Glu Gly Val Val Asp Ile Tyr Asn Cys Val Lys Ala Leu Arg<br>                1125                1130                1135 | 3408 |
| tct cgg cgc att aat atg gta cag aca gag gaa cag tac att ttt att<br>Ser Arg Arg Ile Asn Met Val Gln Thr Glu Glu Gln Tyr Ile Phe Ile<br>            1140                1145                1150 | 3456 |
| cat gat gcc att tta gaa gcc tgc tta tgt gga gaa act gcc atc cct<br>His Asp Ala Ile Leu Glu Ala Cys Leu Cys Gly Glu Thr Ala Ile Pro<br>1155                1160                1165 | 3504 |
| gtg tgt gaa ttt aaa gct gca tat ttt gat atg att cga ata gac tct<br>Val Cys Glu Phe Lys Ala Ala Tyr Phe Asp Met Ile Arg Ile Asp Ser<br>    1170                  1175                1180 | 3552 |
| cag act aac tcc tct cat ctc aaa gat gaa ttt cag act ctg aat tcg<br>Gln Thr Asn Ser Ser His Leu Lys Asp Glu Phe Gln Thr Leu Asn Ser<br>1185                1190                1195                1200 | 3600 |
| gtc acc cct cga cta caa gct gaa gac tgc agc ata gcc tgc ctg cca<br>Val Thr Pro Arg Leu Gln Ala Glu Asp Cys Ser Ile Ala Cys Leu Pro<br>                1205                1210                1215 | 3648 |
| agg aac cat gac aag aac cgt ttc atg gat atg ctc cca cct gac aga<br>Arg Asn His Asp Lys Asn Arg Phe Met Asp Met Leu Pro Pro Asp Arg<br>            1220                1225                1230 | 3696 |
| tgt ctg cct ttt tta att aca att gat ggg gag agc agt aac tac atc<br>Cys Leu Pro Phe Leu Ile Thr Ile Asp Gly Glu Ser Ser Asn Tyr Ile<br>1235                1240                1245 | 3744 |
| aat gct gct ctt atg gat agc tat agg cag cca gca gct ttc atc gtc<br>Asn Ala Ala Leu Met Asp Ser Tyr Arg Gln Pro Ala Ala Phe Ile Val<br>    1250                  1255                1260 | 3792 |
| aca caa tac cca ctg cca aac act gtg aaa gac ttc tgg aga tta gta<br>Thr Gln Tyr Pro Leu Pro Asn Thr Val Lys Asp Phe Trp Arg Leu Val<br>1265                1270                1275                1280 | 3840 |
| tat gat tac gga tgt acc tcc atc gtg atg cta aat gaa gtg gac ctg<br>Tyr Asp Tyr Gly Cys Thr Ser Ile Val Met Leu Asn Glu Val Asp Leu | 3888 |

```
                  1285                1290                1295
tct cag ggc tgc cca cag tac tgg cca gaa gaa gga atg ctg cga tat    3936
Ser Gln Gly Cys Pro Gln Tyr Trp Pro Glu Glu Gly Met Leu Arg Tyr
            1300                1305                1310 ggt cct atc caa gtg gaa tgt atg tct tgt tca atg gac tgt gat gtg    3984
Gly Pro Ile Gln Val Glu Cys Met Ser Cys Ser Met Asp Cys Asp Val
        1315                1320                1325 atc aat cga att ttt aga ata tgc aac cta acg aga cca cag gag ggc    4032
Ile Asn Arg Ile Phe Arg Ile Cys Asn Leu Thr Arg Pro Gln Glu Gly
    1330                1335                1340 tat ctg atg gta caa cag ttc cag tac cta ggc tgg gct tct cat cga    4080
Tyr Leu Met Val Gln Gln Phe Gln Tyr Leu Gly Trp Ala Ser His Arg
1345                1350                1355                1360 gaa gtg cct ggc tcc aaa cgc tcg ttt ttg aaa ttg ata ctg cag gtg    4128
Glu Val Pro Gly Ser Lys Arg Ser Phe Leu Lys Leu Ile Leu Gln Val
                1365                1370                1375 gaa aaa tgg caa gag gaa tgt gaa gaa ggg gaa ggc cgg aca atc atc    4176
Glu Lys Trp Gln Glu Glu Cys Glu Glu Gly Glu Gly Arg Thr Ile Ile
            1380                1385                1390 cac tgc ttg aat ggc ggt ggg cgc agt ggc atg ttc tgt gcc ata ggc    4224
His Cys Leu Asn Gly Gly Gly Arg Ser Gly Met Phe Cys Ala Ile Gly
        1395                1400                1405 att gtt gtg gag atg gtg aag cgg caa aat gtg gtg gat gtt ttc cat    4272
Ile Val Val Glu Met Val Lys Arg Gln Asn Val Val Asp Val Phe His
    1410                1415                1420 gca gta aag acg ctg agg aac agc aag cca aac atg gtg gaa gcc ccg    4320
Ala Val Lys Thr Leu Arg Asn Ser Lys Pro Asn Met Val Glu Ala Pro
1425                1430                1435                1440 gag cag tat cgt ttt tgc tat gat gtg gcg tta gag tac ctg gag tcc    4368
Glu Gln Tyr Arg Phe Cys Tyr Asp Val Ala Leu Glu Tyr Leu Glu Ser
                1445                1450                1455 tca tag                                                            4374
Ser

<210> SEQ ID NO 4
<211> LENGTH: 4651
<212> TYPE: DNA
<213> ORGANISM: Homo sapiens
<220> FEATURE:
<221> NAME/KEY: CDS
<222> LOCATION: (1)..(4317)

<400> SEQUENCE: 4 atg gat acg act gcg gcg gcg gcg ctg cct gct ttt gtg gcg ctc ttg    48
Met Asp Thr Thr Ala Ala Ala Ala Leu Pro Ala Phe Val Ala Leu Leu
1               5                   10                  15 ctc ctc tct cct tgg cct ctc ctg gga tcg gcc caa ggc cag ttc tcc    96
Leu Leu Ser Pro Trp Pro Leu Leu Gly Ser Ala Gln Gly Gln Phe Ser
            20                  25                  30 gca ggt ggc tgt act ttt gat gat ggt cca ggg gcc tgt gat tac cac    144
Ala Gly Gly Cys Thr Phe Asp Asp Gly Pro Gly Ala Cys Asp Tyr His
        35                  40                  45 cag gat ctg tat gat gac ttt gaa tgg gtg cat gtt agt gct caa gag    192
Gln Asp Leu Tyr Asp Asp Phe Glu Trp Val His Val Ser Ala Gln Glu
    50                  55                  60 cct cat tat cta cca ccc gag atg ccc caa ggt tcc tat atg ata gtg    240
Pro His Tyr Leu Pro Pro Glu Met Pro Gln Gly Ser Tyr Met Ile Val
65                  70                  75                  80 gac tct tca gat cac gac cct gga gaa aaa gcc aga ctt cag ctg cct    288
Asp Ser Ser Asp His Asp Pro Gly Glu Lys Ala Arg Leu Gln Leu Pro
                85                  90                  95
```

```
aca atg aag gag aac gac act cac tgc att gat ttc agt tac cta tta      336
Thr Met Lys Glu Asn Asp Thr His Cys Ile Asp Phe Ser Tyr Leu Leu
        100                 105                 110 tat agc cag aaa gga ctg aat cct ggc act ttg aac ata tta gtt agg      384
Tyr Ser Gln Lys Gly Leu Asn Pro Gly Thr Leu Asn Ile Leu Val Arg
    115                 120                 125 gtg aat aaa gga cct ctt gcc aat cca att tgg aat gtg act gga ttc      432
Val Asn Lys Gly Pro Leu Ala Asn Pro Ile Trp Asn Val Thr Gly Phe
130                 135                 140 acg ggt aga gat tgg ctt cgg gct gag cta gca gtg agc acc ttt tgg      480
Thr Gly Arg Asp Trp Leu Arg Ala Glu Leu Ala Val Ser Thr Phe Trp
145                 150                 155                 160 ccc aat gaa tat cag gta ata ttt gaa gct gaa gtc tca gga ggg aga      528
Pro Asn Glu Tyr Gln Val Ile Phe Glu Ala Glu Val Ser Gly Gly Arg
                165                 170                 175 agt ggt tat att gcc att gat gac atc caa gta ctg agt tat cct tgt      576
Ser Gly Tyr Ile Ala Ile Asp Asp Ile Gln Val Leu Ser Tyr Pro Cys
            180                 185                 190 gat aaa tct cct cat ttc ctc cgt cta ggg gat gta gag gtg aat gca      624
Asp Lys Ser Pro His Phe Leu Arg Leu Gly Asp Val Glu Val Asn Ala
        195                 200                 205 ggg caa aac gct aca ttt cag tgc att gcc aca ggg aga gat gct gtg      672
Gly Gln Asn Ala Thr Phe Gln Cys Ile Ala Thr Gly Arg Asp Ala Val
    210                 215                 220 cat aac aag tta tgg ctc cag aga cga aat gga gaa gat ata cca gta      720
His Asn Lys Leu Trp Leu Gln Arg Arg Asn Gly Glu Asp Ile Pro Val
225                 230                 235                 240 gcc cag act aag aac atc aat cat aga agg ttt gcc gct tcc ttc aga      768
Ala Gln Thr Lys Asn Ile Asn His Arg Arg Phe Ala Ala Ser Phe Arg
                245                 250                 255 ttg caa gaa gtg aca aaa act gac cag gat ttg tat cgc tgt gta act      816
Leu Gln Glu Val Thr Lys Thr Asp Gln Asp Leu Tyr Arg Cys Val Thr
            260                 265                 270 cag tca gaa cga ggt tcc ggt gtg tcc aat ttt gct caa ctt att gtg      864
Gln Ser Glu Arg Gly Ser Gly Val Ser Asn Phe Ala Gln Leu Ile Val
        275                 280                 285 aga gaa ccg cca aga ccc att gct cct cct cag ctt ctt ggt gtt ggg      912
Arg Glu Pro Pro Arg Pro Ile Ala Pro Pro Gln Leu Leu Gly Val Gly
    290                 295                 300 cct aca tat ttg ctg atc caa cta aat gcc aac tcg atc att ggc gat      960
Pro Thr Tyr Leu Leu Ile Gln Leu Asn Ala Asn Ser Ile Ile Gly Asp
305                 310                 315                 320 ggt cct atc atc ctg aaa gaa gta gag tac cga atg aca tca gga tcc     1008
Gly Pro Ile Ile Leu Lys Glu Val Glu Tyr Arg Met Thr Ser Gly Ser
                325                 330                 335 tgg aca gaa acc cat gca gtc aat gct cca act tac aaa tta tgg cat     1056
Trp Thr Glu Thr His Ala Val Asn Ala Pro Thr Tyr Lys Leu Trp His
            340                 345                 350 tta gat cca gat acc gaa tat gag atc cga gtt cta ctt aca aga cct     1104
Leu Asp Pro Asp Thr Glu Tyr Glu Ile Arg Val Leu Leu Thr Arg Pro
        355                 360                 365 ggt gaa ggt gga acg ggg ctc cca gga cct cca cta atc acc aga aca     1152
Gly Glu Gly Gly Thr Gly Leu Pro Gly Pro Pro Leu Ile Thr Arg Thr
    370                 375                 380 aaa tgt gca gaa cct atg aga acc cca aag aca tta aag att gct gaa     1200
Lys Cys Ala Glu Pro Met Arg Thr Pro Lys Thr Leu Lys Ile Ala Glu
385                 390                 395                 400 ata cag gca aga cgg att gct gtg gac tgg gaa tcc ttg ggt tac aac     1248
Ile Gln Ala Arg Arg Ile Ala Val Asp Trp Glu Ser Leu Gly Tyr Asn
```

|  |  |  |  |  |  |  |  |  |  |  |  |  |  |  |  |
|---|---|---|---|---|---|---|---|---|---|---|---|---|---|---|---|
|  |  | 405 |  |  |  |  | 410 |  |  |  |  | 415 |  |  |  |
| att | acg | cgt | tgc | cac | act | ttt | aat | gtc | act | atc | tgc | tac | cat | tac | ttc | 1296
| Ile | Thr | Arg | Cys | His | Thr | Phe | Asn | Val | Thr | Ile | Cys | Tyr | His | Tyr | Phe |
|  |  |  | 420 |  |  |  |  | 425 |  |  |  |  | 430 |  |  |
| cgt | ggt | cac | aac | gag | agc | aag | gca | gac | tgt | ttg | gac | atg | gac | ccc | aaa | 1344
| Arg | Gly | His | Asn | Glu | Ser | Lys | Ala | Asp | Cys | Leu | Asp | Met | Asp | Pro | Lys |
|  |  |  | 435 |  |  |  |  | 440 |  |  |  |  | 445 |  |  |
| gcc | cct | cag | cat | gtt | gtg | aac | cat | ctg | cca | cct | tat | aca | aat | gtc | agc | 1392
| Ala | Pro | Gln | His | Val | Val | Asn | His | Leu | Pro | Pro | Tyr | Thr | Asn | Val | Ser |
|  | 450 |  |  |  |  | 455 |  |  |  |  | 460 |  |  |  |  |
| ctc | aag | atg | atc | cta | acc | aat | cca | gag | gga | agg | aag | gag | agt | gaa | gag | 1440
| Leu | Lys | Met | Ile | Leu | Thr | Asn | Pro | Glu | Gly | Arg | Lys | Glu | Ser | Glu | Glu |
| 465 |  |  |  |  | 470 |  |  |  |  | 475 |  |  |  |  | 480 |
| aca | att | att | caa | act | gat | gaa | gat | gtg | cct | ggt | ccc | gta | cca | gta | aaa | 1488
| Thr | Ile | Ile | Gln | Thr | Asp | Glu | Asp | Val | Pro | Gly | Pro | Val | Pro | Val | Lys |
|  |  |  |  | 485 |  |  |  |  | 490 |  |  |  |  | 495 |  |
| tct | ctt | caa | gga | aca | tcc | ttt | gaa | aat | aag | atc | ttc | ttg | aac | tgg | aaa | 1536
| Ser | Leu | Gln | Gly | Thr | Ser | Phe | Glu | Asn | Lys | Ile | Phe | Leu | Asn | Trp | Lys |
|  |  |  | 500 |  |  |  |  | 505 |  |  |  |  | 510 |  |  |
| gaa | cct | ttg | gat | cca | aat | gga | atc | atc | act | caa | tat | gag | atc | agc | tat | 1584
| Glu | Pro | Leu | Asp | Pro | Asn | Gly | Ile | Ile | Thr | Gln | Tyr | Glu | Ile | Ser | Tyr |
|  |  |  | 515 |  |  |  |  | 520 |  |  |  |  | 525 |  |  |
| agc | agt | ata | aga | tca | ttt | gat | cct | gca | gtc | cca | gtg | gct | gga | cct | ccc | 1632
| Ser | Ser | Ile | Arg | Ser | Phe | Asp | Pro | Ala | Val | Pro | Val | Ala | Gly | Pro | Pro |
|  | 530 |  |  |  |  | 535 |  |  |  |  | 540 |  |  |  |  |
| cag | act | gta | tca | aat | tta | tgg | aac | agt | aca | cat | gtc | ttt | atg | cat | 1680
| Gln | Thr | Val | Ser | Asn | Leu | Trp | Asn | Ser | Thr | His | His | Val | Phe | Met | His |
| 545 |  |  |  |  | 550 |  |  |  |  | 555 |  |  |  |  | 560 |
| ctc | cac | cct | gga | acc | acg | tac | cag | ttt | ttc | ata | aga | gcc | agc | acg | gtc | 1728
| Leu | His | Pro | Gly | Thr | Thr | Tyr | Gln | Phe | Phe | Ile | Arg | Ala | Ser | Thr | Val |
|  |  |  |  | 565 |  |  |  |  | 570 |  |  |  |  | 575 |  |
| aaa | ggc | ttt | ggt | cca | gcc | aca | gcc | atc | aat | gtc | acc | acc | aat | atc | tca | 1776
| Lys | Gly | Phe | Gly | Pro | Ala | Thr | Ala | Ile | Asn | Val | Thr | Thr | Asn | Ile | Ser |
|  |  |  | 580 |  |  |  |  | 585 |  |  |  |  | 590 |  |  |
| gct | cca | act | tta | cct | gac | tat | gaa | gga | gtt | gat | gcc | tct | ctc | aat | gaa | 1824
| Ala | Pro | Thr | Leu | Pro | Asp | Tyr | Glu | Gly | Val | Asp | Ala | Ser | Leu | Asn | Glu |
|  |  |  | 595 |  |  |  |  | 600 |  |  |  |  | 605 |  |  |
| act | gcc | acc | aca | ata | act | gta | ttg | ttg | aga | cca | gca | caa | gcc | aaa | ggt | 1872
| Thr | Ala | Thr | Thr | Ile | Thr | Val | Leu | Leu | Arg | Pro | Ala | Gln | Ala | Lys | Gly |
|  | 610 |  |  |  |  | 615 |  |  |  |  | 620 |  |  |  |  |
| gct | cct | atc | agt | gct | tat | cag | att | gtt | gtg | gaa | gaa | ctg | cac | cca | cac | 1920
| Ala | Pro | Ile | Ser | Ala | Tyr | Gln | Ile | Val | Val | Glu | Glu | Leu | His | Pro | His |
| 625 |  |  |  |  | 630 |  |  |  |  | 635 |  |  |  |  | 640 |
| cga | acc | aag | aga | gaa | gcc | gga | gcc | atg | gaa | tgc | tac | cag | gtt | cct | gtc | 1968
| Arg | Thr | Lys | Arg | Glu | Ala | Gly | Ala | Met | Glu | Cys | Tyr | Gln | Val | Pro | Val |
|  |  |  |  | 645 |  |  |  |  | 650 |  |  |  |  | 655 |  |
| aca | tac | caa | aat | gcc | atg | agt | ggg | ggt | gca | ccg | tat | tac | ttt | gct | gca | 2016
| Thr | Tyr | Gln | Asn | Ala | Met | Ser | Gly | Gly | Ala | Pro | Tyr | Tyr | Phe | Ala | Ala |
|  |  |  | 660 |  |  |  |  | 665 |  |  |  |  | 670 |  |  |
| gaa | cta | ccc | ccg | gga | aac | cta | cct | gag | cct | gcc | ccg | ttc | act | gtg | ggt | 2064
| Glu | Leu | Pro | Pro | Gly | Asn | Leu | Pro | Glu | Pro | Ala | Pro | Phe | Thr | Val | Gly |
|  |  |  | 675 |  |  |  |  | 680 |  |  |  |  | 685 |  |  |
| gac | aat | cgg | acc | tac | caa | ggc | ttt | tgg | aac | cct | cct | ttg | gct | ccg | cgc | 2112
| Asp | Asn | Arg | Thr | Tyr | Gln | Gly | Phe | Trp | Asn | Pro | Pro | Leu | Ala | Pro | Arg |
|  | 690 |  |  |  |  | 695 |  |  |  |  | 700 |  |  |  |  |
| aaa | gga | tac | aac | atc | tat | ttc | cag | gcg | atg | agc | agt | gtg | gag | aag | gaa | 2160
| Lys | Gly | Tyr | Asn | Ile | Tyr | Phe | Gln | Ala | Met | Ser | Ser | Val | Glu | Lys | Glu |
| 705 |  |  |  |  | 710 |  |  |  |  | 715 |  |  |  |  | 720 |
| act | aaa | acc | cag | tgc | gta | cgc | att | gct | aca | aaa | gca | gca | aca | gaa | gaa | 2208

```
Thr Lys Thr Gln Cys Val Arg Ile Ala Thr Lys Ala Ala Thr Glu Glu
                725                 730                 735 cca gaa gtg atc cca gat ccc gcc aag cag aca gac aga gtg gtg aaa      2256
Pro Glu Val Ile Pro Asp Pro Ala Lys Gln Thr Asp Arg Val Val Lys
            740                 745                 750 ata gca gga att agt gct gga att ttg gtc ttc atc ctc ctt ctc cta      2304
Ile Ala Gly Ile Ser Ala Gly Ile Leu Val Phe Ile Leu Leu Leu Leu
        755                 760                 765 gtt gtc ata tta att gta aaa aag agc aaa ctt gct aaa aaa cgc aaa      2352
Val Val Ile Leu Ile Val Lys Lys Ser Lys Leu Ala Lys Lys Arg Lys
    770                 775                 780 gat gcc atg ggg aat acc cgg cag gag atg act cac atg gtg aat gca      2400
Asp Ala Met Gly Asn Thr Arg Gln Glu Met Thr His Met Val Asn Ala
785                 790                 795                 800 atg gat cga agt tat gct gat cag agc act ctg cat gca gaa gat cct      2448
Met Asp Arg Ser Tyr Ala Asp Gln Ser Thr Leu His Ala Glu Asp Pro
                805                 810                 815 ctt tcc atc acc ttc atg gac caa cat aac ttt agt cca aga tat gag      2496
Leu Ser Ile Thr Phe Met Asp Gln His Asn Phe Ser Pro Arg Tyr Glu
            820                 825                 830 aac cac agt gct aca gca gag tcc agt cgc ctt cta gac gta cct cgc      2544
Asn His Ser Ala Thr Ala Glu Ser Ser Arg Leu Leu Asp Val Pro Arg
        835                 840                 845 tac ctc tgt gag ggg acg gaa tcc cct tac cag aca gga cag ctg cat      2592
Tyr Leu Cys Glu Gly Thr Glu Ser Pro Tyr Gln Thr Gly Gln Leu His
    850                 855                 860 cca gcc atc agg gta gct gat tta ctg cag cac att aat ctc atg aag      2640
Pro Ala Ile Arg Val Ala Asp Leu Leu Gln His Ile Asn Leu Met Lys
865                 870                 875                 880 aca tca gac agc tat ggg ttc aaa gag gaa tat gag agc ttt ttt gaa      2688
Thr Ser Asp Ser Tyr Gly Phe Lys Glu Glu Tyr Glu Ser Phe Phe Glu
                885                 890                 895 gga cag tca gca tct tgg gat gta gct aaa aaa gat caa aat aga gca      2736
Gly Gln Ser Ala Ser Trp Asp Val Ala Lys Lys Asp Gln Asn Arg Ala
            900                 905                 910 aaa aac cga tat gga aac att ata gca tat gat cac tcc aga gtg att      2784
Lys Asn Arg Tyr Gly Asn Ile Ile Ala Tyr Asp His Ser Arg Val Ile
        915                 920                 925 ttg caa ccc gta gag gat gat cct tcc tca gat tat att aat gcc aac      2832
Leu Gln Pro Val Glu Asp Asp Pro Ser Ser Asp Tyr Ile Asn Ala Asn
    930                 935                 940 tat att gat ggc tac cag aga cca agt cat tac att gca acc caa ggt      2880
Tyr Ile Asp Gly Tyr Gln Arg Pro Ser His Tyr Ile Ala Thr Gln Gly
945                 950                 955                 960 ccc gtt cat gaa aca gtg tat gat ttc tgg agg atg att tgg caa gaa      2928
Pro Val His Glu Thr Val Tyr Asp Phe Trp Arg Met Ile Trp Gln Glu
                965                 970                 975 caa tct gct tgc att gtg atg gtt aca aat tta gtt gag gtt ggc cgg      2976
Gln Ser Ala Cys Ile Val Met Val Thr Asn Leu Val Glu Val Gly Arg
            980                 985                 990 gtt aaa tgc tat aaa tat tgg cct gat gat act gaa gtt tat ggt gac      3024
Val Lys Cys Tyr Lys Tyr Trp Pro Asp Asp Thr Glu Val Tyr Gly Asp
        995                 1000                1005 ttc aaa gta acg tgt gta gaa atg gaa cca ctt gct gaa tat gta gtt      3072
Phe Lys Val Thr Cys Val Glu Met Glu Pro Leu Ala Glu Tyr Val Val
    1010                1015                1020 agg aca ttc acc ctg gaa agg agg ggg tac aat gaa atc cgt gaa gtt      3120
Arg Thr Phe Thr Leu Glu Arg Arg Gly Tyr Asn Glu Ile Arg Glu Val
1025                1030                1035                1040
```

-continued

| | |
|---|---|
| aaa cag ttc cat ttc acg ggc tgg cct gac cat gga gtg ccc tac cat<br>Lys Gln Phe His Phe Thr Gly Trp Pro Asp His Gly Val Pro Tyr His<br>                      1045                      1050                    1055 | 3168 |
| gct aca ggg ctg ctt tcc ttt atc cgg cga gtc aag tta tca aac cct<br>Ala Thr Gly Leu Leu Ser Phe Ile Arg Arg Val Lys Leu Ser Asn Pro<br>                      1060                      1065                    1070 | 3216 |
| ccc agt gct ggc ccc atc gtt gta cat tgc agt gct ggt gct gga cga<br>Pro Ser Ala Gly Pro Ile Val Val His Cys Ser Ala Gly Ala Gly Arg<br>            1075                      1080                    1085 | 3264 |
| act ggc tgc tac att gtg att gac atc atg cta gac atg gct gaa aga<br>Thr Gly Cys Tyr Ile Val Ile Asp Ile Met Leu Asp Met Ala Glu Arg<br>            1090                      1095                    1100 | 3312 |
| gag ggt gtt gtt gat att tac aat tgt gtc aaa gcc tta aga tct cgg<br>Glu Gly Val Val Asp Ile Tyr Asn Cys Val Lys Ala Leu Arg Ser Arg<br>1105                      1110                    1115                    1120 | 3360 |
| cgt att aat atg gtc cag aca gag gaa cag tac att ttt att cat gat<br>Arg Ile Asn Met Val Gln Thr Glu Glu Gln Tyr Ile Phe Ile His Asp<br>                      1125                      1130                    1135 | 3408 |
| gcc att tta gaa gcc tgc tta tgt gga gaa act gcc ata cct gtc tgt<br>Ala Ile Leu Glu Ala Cys Leu Cys Gly Glu Thr Ala Ile Pro Val Cys<br>            1140                      1145                    1150 | 3456 |
| gaa ttt aaa gct gca tat ttt gat atg att aga ata gac tcc cag act<br>Glu Phe Lys Ala Ala Tyr Phe Asp Met Ile Arg Ile Asp Ser Gln Thr<br>                      1155                      1160                    1165 | 3504 |
| aac tct tca cat ctc aag gat gaa ttt cag act ctg aat tca gtc acc<br>Asn Ser Ser His Leu Lys Asp Glu Phe Gln Thr Leu Asn Ser Val Thr<br>        1170                      1175                    1180 | 3552 |
| cct cga cta caa gct gaa gac tgc agt ata gcg tgc ctg cca agg aac<br>Pro Arg Leu Gln Ala Glu Asp Cys Ser Ile Ala Cys Leu Pro Arg Asn<br>1185                      1190                    1195                    1200 | 3600 |
| cat gac aag aac cgt ttc atg gac atg ctg cca cct gac aga tgt ctg<br>His Asp Lys Asn Arg Phe Met Asp Met Leu Pro Pro Asp Arg Cys Leu<br>                      1205                      1210                    1215 | 3648 |
| cct ttt tta att aca att gat ggg gag agc agt aac tac atc aat gct<br>Pro Phe Leu Ile Thr Ile Asp Gly Glu Ser Ser Asn Tyr Ile Asn Ala<br>        1220                      1225                    1230 | 3696 |
| gct ctt atg gac agc tac agg caa cca gct gct ttc atc gtc aca caa<br>Ala Leu Met Asp Ser Tyr Arg Gln Pro Ala Ala Phe Ile Val Thr Gln<br>            1235                      1240                    1245 | 3744 |
| tac cct ctg cca aac act gta aaa gac ttc tgg aga tta gtg tat gat<br>Tyr Pro Leu Pro Asn Thr Val Lys Asp Phe Trp Arg Leu Val Tyr Asp<br>                1250                      1255                    1260 | 3792 |
| tat ggc tgt acc tcc att gtg atg tta aac gaa gtc gac ttg tcc cag<br>Tyr Gly Cys Thr Ser Ile Val Met Leu Asn Glu Val Asp Leu Ser Gln<br>1265                      1270                    1275                    1280 | 3840 |
| ggc tgc cct cag tac tgg cca gag gaa ggg atg cta cga tat ggc ccc<br>Gly Cys Pro Gln Tyr Trp Pro Glu Glu Gly Met Leu Arg Tyr Gly Pro<br>                      1285                      1290                    1295 | 3888 |
| atc caa gtg gaa tgt atg tct tgt tca atg gac tgt gat gtg atc aac<br>Ile Gln Val Glu Cys Met Ser Cys Ser Met Asp Cys Asp Val Ile Asn<br>            1300                      1305                    1310 | 3936 |
| cgg att ttt agg ata tgc aat cta aca aga cca cag gaa ggt tat ctg<br>Arg Ile Phe Arg Ile Cys Asn Leu Thr Arg Pro Gln Glu Gly Tyr Leu<br>                1315                      1320                    1325 | 3984 |
| atg gtg caa cag ttt cag tac cta gga tgg gct tct cat cga gaa gtg<br>Met Val Gln Gln Phe Gln Tyr Leu Gly Trp Ala Ser His Arg Glu Val<br>                      1330                      1335                    1340 | 4032 |
| cct gga tcc aaa agg tca ttc ttg aaa ctg ata ctt cag gtg gaa aag<br>Pro Gly Ser Lys Arg Ser Phe Leu Lys Leu Ile Leu Gln Val Glu Lys<br>1345                      1350                    1355                    1360 | 4080 |

-continued

```
tgg cag gag gaa tgg aag gaa ggg gaa ggc cgg acg att atc cac tgc      4128
Trp Gln Glu Glu Trp Lys Glu Gly Glu Gly Arg Thr Ile Ile His Cys
            1365                1370                1375 cta aat ggt ggc ggg cga agt ggc atg ttc tgt gct ata ggc atc gtt      4176
Leu Asn Gly Gly Gly Arg Ser Gly Met Phe Cys Ala Ile Gly Ile Val
        1380                1385                1390 gtt gaa atg gtg aaa cgg caa aat gtt gtc gat gtt ttc cat gca gta      4224
Val Glu Met Val Lys Arg Gln Asn Val Val Asp Val Phe His Ala Val
    1395                1400                1405 aag aca ctg agg aac agc aag cca aac atg gtg gaa gcc ccg gag caa      4272
Lys Thr Leu Arg Asn Ser Lys Pro Asn Met Val Glu Ala Pro Glu Gln
    1410                1415                1420 tac cgt ttc tgc tat gat gta gct ttg gag tac ctg gaa tca tct           4317
Tyr Arg Phe Cys Tyr Asp Val Ala Leu Glu Tyr Leu Glu Ser Ser
1425                1430                1435 tagttgggtg agactcttta aagtgcatcc atgaagaaac ctgtccatct attgagccag     4377
cagctgttgt acctgttaca cttgtgcaga aagattttaa tgtgggggt gggagacttt      4437 tacatttgag aggtaaaagt attttttta tgaagttgtg tatcttaata aaaagaactg      4497
aattagtttt tattactatt ataaagcatc aacatttcat gccacataaa attatattta    4557
ataagaacca gattgaaatg agaacgtatt ggtgtttgta cagtgaacat gccacctttt    4617
tccatggttt caggtagtgc agctaccaca tgtt                                 4651
```

<210> SEQ ID NO 5
<211> LENGTH: 78
<212> TYPE: PRT
<213> ORGANISM: Homo sapiens

<400> SEQUENCE: 5

Pro Pro Thr Asn Leu His Leu Glu Ala Asn Pro Asp Thr Gly Val Leu
 1               5                  10                  15

Thr Val Ser Trp Glu Arg Ser Thr Thr Pro Asp Ile Thr Gly Tyr Arg
            20                  25                  30

Ile Thr Thr Thr Pro Thr Asn Gly Gln Gln Gly Asn Ser Leu Glu Glu
        35                  40                  45

Val Val His Ala Asp Gln Ser Ser Cys Thr Phe Asp Asn Leu Ser Pro
    50                  55                  60

Gly Leu Glu Tyr Asn Val Ser Val Tyr Thr Val Lys Asp Asp
65                  70                  75

<210> SEQ ID NO 6
<211> LENGTH: 155
<212> TYPE: PRT
<213> ORGANISM: Mus musculus

<400> SEQUENCE: 6

Gly Gly Cys Leu Phe Asp Glu Pro Tyr Ser Thr Cys Gly Tyr Ser Gln
 1               5                  10                  15

Ala Asp Glu Asp Phe Asn Trp Glu Gln Val Asn Thr Leu Thr Lys Pro
            20                  25                  30

Thr Ser Asp Pro Trp Met Pro Ser Gly Ser Phe Met Leu Val Asn Thr
        35                  40                  45

Ser Gly Lys Pro Glu Gly Gln Arg Ala His Leu Leu Pro Gln Leu
    50                  55                  60

Lys Glu Asn Asp Thr His Cys Ile Asp Phe His Tyr Phe Val Ser Ser
65                  70                  75                  80

```
Lys Ser Asn Ala Ala Pro Gly Leu Leu Asn Val Tyr Val Lys Val Asn
                85                  90                  95

Asn Gly Pro Leu Gly Asn Pro Ile Trp Asn Ile Ser Gly Asp Pro Thr
            100                 105                 110

Arg Thr Trp His Arg Ala Glu Leu Ala Ile Ser Thr Phe Trp Pro Asn
        115                 120                 125

Phe Tyr Gln Val Ile Phe Glu Val Val Thr Ser Gly His Gln Gly Tyr
    130                 135                 140

Leu Ala Ile Asp Glu Val Lys Val Leu Gly His
145                 150                 155

<210> SEQ ID NO 7
<211> LENGTH: 154
<212> TYPE: PRT
<213> ORGANISM: Mus musculus

<400> SEQUENCE: 7

Cys Lys Phe Gly Trp Gly Ser Gln Lys Thr Val Cys Asn Trp Gln His
1               5                   10                  15

Asp Ile Ser Ser Asp Leu Lys Trp Ala Val Leu Asn Ser Lys Thr Gly
            20                  25                  30

Pro Val Gln Asp His Thr Gly Asp Gly Asn Phe Ile Tyr Ser Glu Ala
        35                  40                  45

Asp Glu Arg His Glu Gly Arg Ala Ala Arg Leu Met Ser Pro Val Val
    50                  55                  60

Ser Ser Ser Arg Ser Ala His Cys Leu Thr Phe Trp Tyr His Met Asp
65                  70                  75                  80

Gly Ser His Val Gly Thr Leu Ser Ile Lys Leu Lys Tyr Glu Met Glu
                85                  90                  95

Glu Asp Phe Asp Gln Thr Leu Trp Thr Val Ser Gly Asn Gln Gly Asp
            100                 105                 110

Gln Trp Lys Glu Ala Arg Val Val Leu His Lys Thr Met Lys Gln Tyr
        115                 120                 125

Gln Val Ile Val Glu Gly Thr Val Gly Lys Gly Ser Ala Gly Gly Ile
    130                 135                 140

Ala Val Asp Asp Ile Ile Ile Ala Asn His
145                 150

<210> SEQ ID NO 8
<211> LENGTH: 1452
<212> TYPE: PRT
<213> ORGANISM: Homo sapiens

<400> SEQUENCE: 8

Met Arg Thr Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
            20                  25                  30

Tyr Ser Thr Cys Gly Tyr Ser Gln Ser Glu Gly Asp Asp Phe Asn Trp
        35                  40                  45

Glu Gln Val Asn Thr Leu Thr Lys Pro Thr Ser Asp Pro Trp Met Pro
    50                  55                  60

Ser Gly Ser Leu Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95
```

```
Ile Asp Phe His Tyr Phe Val Ser Ser Lys Ser Asn Ser Pro Pro Gly
                100                 105                 110

Leu Leu Asn Val Tyr Val Lys Val Asn Asn Gly Pro Leu Gly Asn Pro
            115                 120                 125

Ile Trp Asn Ile Ser Gly Asp Pro Thr Arg Thr Trp Asn Arg Ala Glu
        130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
            180                 185                 190

Asn Val Glu Val Asn Ala Gly Gln Phe Ala Thr Phe Gln Cys Ser Ala
        195                 200                 205

Ile Gly Arg Thr Val Ala Gly Asp Arg Leu Trp Leu Gln Gly Ile Asp
    210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Arg Thr Glu Gly Gly Val Gly Ile Ser Asn
            260                 265                 270

Tyr Ala Glu Leu Val Val Lys Glu Pro Pro Val Pro Ile Ala Pro Pro
        275                 280                 285

Gln Leu Ala Ser Val Gly Ala Thr Tyr Leu Trp Ile Gln Leu Asn Ala
    290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
            340                 345                 350

Val Leu Leu Thr Arg Pro Gly Glu Gly Gly Thr Gly Ser Pro Gly Pro
        355                 360                 365

Ala Leu Arg Thr Arg Thr Lys Cys Ala Asp Pro Met Arg Gly Pro Arg
    370                 375                 380

Lys Leu Glu Val Val Glu Val Lys Ser Arg Gln Ile Thr Ile Arg Trp
385                 390                 395                 400

Glu Pro Phe Gly Tyr Asn Val Thr Arg Cys His Ser Tyr Asn Leu Thr
                405                 410                 415

Val His Tyr Cys Tyr Gln Val Gly Gly Gln Glu Gln Val Arg Glu Glu
            420                 425                 430

Val Ser Trp Asp Thr Glu Asn Ser His Pro Gln His Thr Ile Thr Asn
        435                 440                 445

Leu Ser Pro Tyr Thr Asn Val Ser Val Lys Leu Ile Leu Met Asn Pro
    450                 455                 460

Glu Gly Arg Lys Glu Ser Gln Glu Leu Thr Val Gln Thr Asp Glu Asp
465                 470                 475                 480

Leu Pro Gly Ala Val Pro Thr Glu Ser Ile Gln Gly Ser Thr Phe Glu
                485                 490                 495

Glu Lys Ile Phe Leu Gln Trp Arg Glu Pro Thr Gln Thr Tyr Gly Val
            500                 505                 510

Ile Thr Leu Tyr Glu Ile Thr Tyr Lys Ala Val Ser Ser Phe Asp Pro
```

-continued

```
            515                 520                 525
Glu Ile Asp Leu Ser Asn Gln Ser Gly Arg Val Ser Lys Leu Gly Asn
    530                 535                 540
Glu Thr His Phe Leu Phe Phe Gly Leu Tyr Pro Gly Thr Thr Tyr Ser
545                 550                 555                 560
Phe Thr Ile Arg Ala Ser Thr Ala Lys Gly Phe Gly Pro Pro Ala Thr
                565                 570                 575
Asn Gln Phe Thr Thr Lys Ile Ser Ala Pro Ser Met Pro Ala Tyr Glu
            580                 585                 590
Leu Glu Thr Pro Leu Asn Gln Thr Asp Asn Thr Val Thr Val Met Leu
        595                 600                 605
Lys Pro Ala Gln Ser Arg Gly Ala Pro Val Ser Val Tyr Gln Ile Val
    610                 615                 620
Val Glu Glu Arg Pro Arg Arg Thr Lys Lys Thr Thr Glu Ile Leu
625                 630                 635                 640
Lys Cys Tyr Pro Val Pro Ile His Phe Gln Asn Ala Ser Leu Leu Asn
                645                 650                 655
Ser Gln Tyr Tyr Phe Ala Ala Glu Phe Pro Ala Asp Ser Leu Gln Ala
            660                 665                 670
Ala Gln Pro Phe Thr Ile Gly Asp Asn Lys Thr Tyr Asn Gly Tyr Trp
        675                 680                 685
Asn Thr Pro Leu Leu Pro Tyr Lys Ser Tyr Arg Ile Tyr Phe Gln Ala
    690                 695                 700
Ala Ser Arg Ala Asn Gly Glu Thr Lys Ile Asp Cys Val Gln Val Ala
705                 710                 715                 720
Thr Lys Gly Ala Ala Thr Pro Lys Pro Val Pro Glu Pro Glu Lys Gln
                725                 730                 735
Thr Asp His Thr Val Lys Ile Ala Gly Val Ile Ala Gly Ile Leu Leu
            740                 745                 750
Phe Val Ile Ile Phe Leu Gly Val Leu Val Met Lys Lys Arg Lys
        755                 760                 765
Leu Ala Lys Lys Arg Lys Glu Thr Met Ser Ser Thr Arg Gln Glu Met
    770                 775                 780
Thr Val Met Val Asn Ser Met Asp Lys Ser Tyr Ala Glu Gln Gly Thr
785                 790                 795                 800
Asn Cys Asp Glu Ala Phe Ser Phe Met Asp Thr His Asn Leu Asn Gly
                805                 810                 815
Arg Ser Val Ser Ser Pro Ser Ser Phe Thr Met Lys Thr Asn Thr Leu
            820                 825                 830
Ser Thr Ser Val Pro Asn Ser Tyr Tyr Pro Asp Glu Thr His Thr Met
        835                 840                 845
Ala Ser Asp Thr Ser Ser Leu Val Gln Ser His Thr Tyr Lys Lys Arg
    850                 855                 860
Glu Pro Ala Asp Val Pro Tyr Gln Thr Gly Gln Leu His Pro Ala Ile
865                 870                 875                 880
Arg Val Ala Asp Leu Leu Gln His Ile Thr Gln Met Lys Cys Ala Glu
                885                 890                 895
Gly Tyr Gly Phe Lys Glu Glu Tyr Glu Ser Phe Phe Glu Gly Gln Ser
            900                 905                 910
Ala Ser Trp Asp Val Ala Lys Lys Asp Gln Asn Arg Ala Lys Asn Arg
        915                 920                 925
Tyr Gly Asn Ile Ile Ala Tyr Asp His Ser Arg Val Ile Leu Gln Pro
    930                 935                 940
```

```
Val Glu Gly Asp Thr Asn Ser Asp Tyr Ile Asn Gly Asn Tyr Ile Asp
945                 950                 955                 960

Gly Tyr His Arg Pro Asn His Tyr Ile Ala Thr Gln Gly Pro Met Gln
                965                 970                 975

Glu Thr Ile Tyr Asp Phe Trp Arg Met Val Trp His Glu Asn Thr Ala
            980                 985                 990

Ser Ile Ile Met Val Thr Asn Leu Val Glu Val Gly Arg Val Lys Cys
        995                 1000                1005

Cys Lys Tyr Trp Pro Asp Asp Thr Glu Ile Tyr Lys Asp Ile Lys Val
    1010                1015                1020

Thr Leu Ile Glu Thr Glu Leu Leu Ala Glu Tyr Val Ile Arg Thr Phe
1025                1030                1035                1040

Ala Val Glu Lys Arg Gly Ile Ile Glu Ile Arg Glu Ile Arg Gln Phe
                1045                1050                1055

His Phe Thr Gly Trp Pro Asp His Gly Val Pro Tyr His Ala Thr Gly
            1060                1065                1070

Leu Leu Gly Phe Val Arg Gln Val Lys Ser Lys Ser Pro Pro Ser Ala
        1075                1080                1085

Gly Pro Leu Val Val His Cys Ser Ala Gly Ala Gly Arg Thr Gly Cys
    1090                1095                1100

Phe Ile Val Ile Asp Ile Met Leu Asp Met Ala Glu Arg Glu Gly Val
1105                1110                1115                1120

Val Asp Ile Tyr Asn Cys Val Arg Glu Leu Arg Ser Arg Arg Val Asn
                1125                1130                1135

Met Val Gln Thr Glu Glu Gln Tyr Val Phe Ile His Asp Ala Ile Leu
            1140                1145                1150

Glu Ala Cys Leu Cys Gly Asp Thr Ser Val Pro Ala Ser Gln Val Arg
        1155                1160                1165

Ser Leu Tyr Tyr Asp Met Asn Lys Leu Asp Pro Gln Thr Asn Ser Ser
    1170                1175                1180

Gln Ile Lys Glu Glu Phe Arg Thr Leu Asn Met Val Thr Pro Thr Leu
1185                1190                1195                1200

Arg Val Glu Asp Cys Ser Ile Ala Leu Leu Pro Arg Asn His Glu Lys
                1205                1210                1215

Asn Arg Cys Met Asp Ile Leu Pro Pro Asp Arg Cys Leu Pro Phe Leu
            1220                1225                1230

Ile Thr Ile Asp Gly Glu Ser Ser Asn Tyr Ile Asn Ala Ala Leu Met
        1235                1240                1245

Asp Ser Tyr Lys Gln Pro Ser Ala Phe Ile Val Thr Gln His Pro Leu
    1250                1255                1260

Pro Asn Thr Val Lys Asp Phe Trp Arg Leu Val Leu Asp Tyr His Cys
1265                1270                1275                1280

Thr Ser Val Val Met Leu Asn Asp Val Asp Pro Ala Gln Leu Cys Pro
                1285                1290                1295

Gln Tyr Trp Pro Glu Asn Gly Val His Arg His Gly Pro Ile Gln Val
            1300                1305                1310

Glu Phe Val Ser Ala Asp Leu Glu Glu Asp Ile Ile Ser Arg Ile Phe
        1315                1320                1325

Arg Ile Tyr Asn Ala Ala Arg Pro Gln Asp Gly Tyr Arg Met Val Gln
    1330                1335                1340

Gln Phe Gln Phe Leu Gly Trp Pro Met Tyr Arg Asp Thr Pro Val Ser
1345                1350                1355                1360
```

-continued

```
Lys Arg Ser Phe Leu Lys Leu Ile Arg Gln Val Asp Lys Trp Gln Glu
            1365                1370                1375

Glu Tyr Asn Gly Gly Glu Gly Pro Thr Val Val His Cys Leu Asn Gly
        1380                1385                1390

Gly Gly Arg Ser Gly Thr Phe Cys Ala Ile Ser Ile Val Cys Glu Met
    1395                1400                1405

Leu Arg His Gln Arg Thr Val Asp Val Phe His Ala Val Lys Thr Leu
1410                1415                1420

Arg Asn Asn Lys Pro Asn Met Val Asp Leu Leu Asp Gln Tyr Lys Phe
1425                1430                1435                1440

Cys Tyr Glu Val Ala Leu Glu Tyr Leu Asn Ser Gly
            1445                1450

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 9
gagccgcggc tcgagttaac cgccatggat gtggcggccg                          40

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
gctcacagct agttcagccc                                               20

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctacacccac atctaacgaa ccgtgaagca ggg                                 33

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence:
      Illustrative cleavage motif

<400> SEQUENCE: 12

Arg Thr Lys Arg
  1

<210> SEQ ID NO 13
<211> LENGTH: 4
<212> TYPE: PRT
<213> ORGANISM: Artificial Sequence
<220> FEATURE:
```

-continued

```
<223> OTHER INFORMATION: Description of Artificial Sequence:
      Illustrative modified cleavage motif

<400> SEQUENCE: 13

Leu Thr Asn Arg
 1
```

RECEPTOR-TYPE PHOSPHOTYROSINE PHOSPHATASE-KAPPA ANTIBODIES

This is a Continuation Application of application Ser. No. 09/234,883 filed Jan. 21, 1999 now abandoned, which is, a Divisional Application of Ser. No. 08/087,244 filed Jul. 1, 1993, now U.S. Pat. No. 5,863,755, which is a continuation-in-part of application Ser. No. 08/049,384, filed Apr. 21, 1993, now abandoned.

1. INTRODUCTION

The invention in the field of biochemistry and cell and molecular biology relates to novel receptor-type protein tyrosine phosphatase protein or glycoprotein, termed RPTPκ (also known as RPTPase-κ), DNA coding therefore, methods for production and identification of the protein, methods for screening compounds capable of binding to and inhibiting or stimulating PTPase enzymatic activity, methods for inhibiting homophilic binding of RPTPκ, and methods for identifying compounds which are capable of inhibiting homophilic RPTPκ binding.

The invention in the field of biochemistry and cell and molecular biology relates to novel receptor-type protein tyrosine phosphatase protein or glycoprotein, termed RPTPκ (also known as RPTPase-κ), DNA coding therefor, methods for production and identification of the protein, methods for screening compounds capable of binding to and inhibiting or stimulating PTPase enzymatic activity, methods for inhibiting homophilic binding of RPTPκ, and methods for identifying compounds which are capable of inhibiting homophilic RPTPκ binding.

2. BACKGROUND OF THE INVENTION

Tyrosine phosphorylation of proteins is involved in an increasing number of cellular signalling events. It was originally implicated in signalling by paracrine- or autocrine-acting growth factors, and endocrine hormones such as insulin (see Yarden, Y. et al., Annu. Rev. Biochem. 57:443–478 (1988) for review). It is now clear that this posttranslational modification is also involved in diverse processes such as the activation of cells of the immune system by antigens (Klausner, R. D. et al., Cell 64:875–878), signalling by lymphokines (Hatakeyama, M. et al., 1991 Science 252:1523–1528 (1991); Mills, G. B. et al., J. Biol. Chem. 265:3561–3567 (1990)), and cellular differentiation and survival (Fu, X.-Y. 1992 Cell 70:323–335; Schlessinger, J. et al. 1992 Neuron 9:1–20; Velazquez, L. et al., 1992 Cell 70:313–322). In view of the diversity of processes in which tyrosine phosphorylation is involved, it is not surprising that links are also emerging with the process of cell adhesion and cell-cell contact.

The identification of several growth factor receptors and retroviral oncogenes as tyrosine-specific protein kinases indicated that protein phosphorylation on tyrosine residues plays a key role in cellular growth control. This notion has recently received support by the observation that the level of tyrosine phosphorylation of enzymes thought to play an important role in signal transduction (such as phospholipase C) correlates with their increased activity upon growth factor stimulation, thus establishing a functional role for tyrosine phosphorylation (Ullrich, A., et al., Cell 61:203–212 (1990)).

Most of the processes in which tyrosine phosphorylation is implicated involve the transduction of a signal through the cell membrane. In its best understood fashion, this can occur through dimerization-mediated activation of members of the receptor tyrosine kinase family by soluble ligands (reviewed in Ullrich, A. et al. 1990 Cell 61:203–212). However, modulation of receptor tyrosine kinase activity can also occur by membrane-bound ligands on neighboring cells, as in the case of the interaction between the sevenless kinase and the bride of sevenless protein (Rubin, G. M. 1991, Trends in Genetics 7:372–376). Recently, receptor-like tyrosine kinases were described with an extracellular domain similar to that of cell adhesion molecules of the CAM-family (e.g. Axl and Ark (O'Bryan, J. P. et al., 1991 Mol. Cell. Biol. 11:5016–5031; Rescigno, J. et al., 1991 Oncogene 6:1909–1913)). Such observations may implicate tyrosine phosphorylation as a more broadly used direct downstream effector mechanism for precise cell-cell recognition and signalling events. Members of the non-receptor family of tyrosine kinases have also in several instances been shown to be associated with other proteins with a trans-membrane topology, examples being the association of the Lck and Fyn kinases with the CD4 protein and T-cell receptor complex components respectively (Haughn, L. et al., 1992 Nature 358:328–331; Samelson, L. E. et al., 1992 Proc. Natl. Acad. Sci. USA 87:4358–4362; Veillette, A. et al., 1988 Cell 55:301–308). However, the mechanism by which kinase activity is modulated in these instances is not understood.

The degree and pattern of phosphorylation of tyrosine residues on cellular proteins are regulated by the opposing activities of protein-tyrosine kinases (PTKases; ATP:protein-tyrosine O-phosphotransferase, EC 2.7.1.112) and protein-tyrosine-phosphatases (PTPases; protein-tyrosine-phosphate phosphohydrolase, EC 3.1.3.48). The structural characteristics and evolution of PTKases as well as their role in the regulation of cell growth have been reviewed (Hunter, T., et al., Annu. Rev. Biochem. 54:897–930 (1985); Ullrich, A., et al., supra).

2.1. PTKases

Tyrosine kinases comprise a discrete family of enzymes having common ancestry with, but major differences from, serine/threonine-specific protein kinases (Hanks, S. K. et al., (1988) Science 241:42–52). The mechanisms leading to changes in activity of tyrosine kinases are best understood for receptor-type tyrosine kinases which have a transmembrane topology (Ullrich, A. et al., supra). With such kinases, the binding of specific ligands to the extracellular domain of these enzymes is thought to induce their oligomerization leading to an increase in tyrosine kinase activity and activation of the signal transduction pathways (Ullrich, A. et al., supra). The importance of this activity is supported by the knowledge that dysregulation of kinase activity through mutation or over-expression is a mechanism for oncogenic transformation (Hunter, T. et al., supra; Ullrich, A. et al., 1990, supra).

2.2. PTPases

The protein phosphatases are composed of at least two separate and distinct families (Hunter, T. Cell, 58:1013–1016 (1989)), the protein serine/threonine phosphatases and the protein tyrosine phosphatases. This is in contrast to protein kinases, which show clear sequence similarity between serine/threonine-specific and tyrosine-specific enzymes.

There appear to be two basic types of PTPase molecules. The first group is comprised of small, soluble enzymes that contain a single conserved phosphatase catalytic domain, and include (1) placental PTPase 1B (Charbonneau, H. et al., Proc. Natl. Acad. Sci. 86:5252–5256 (1989); Chernoff, J. et al., Proc. Natl. Acad. Sci. USA 87:2735–2789 (1990)), (2)

T-cell PTPase (Cool, D. E. et al., *Proc. Natl. Acad. Sci. USA* 86:5257–5261 (1989)), and (3) rat brain PTPase (Guan, K., et al., *Proc. Natl. Acad. Sci. USA*, 87:1501–1505 (1990).

The identification of a tyrosine phosphatase homology domain has raised new interest in the potential of PTPases to act as modulators of tyrosine phosphorylation (Kaplan, R. et al. 1990 Proc. Natl. Acad. Sci. USA 87:7000–7004; Krueger, N. X. et al., 1990 EMBO J. 9:3241–3252; see, for review, Fischer, E. H. et al., 1991 Science 253:401–406).

The second group of PTPases is made up of the more complex, receptor-linked PTPases, termed R-PTPases or RPTPs, which are of high molecular weight and contain two tandemly repeated conserved domains separated by 56–57 amino acids. RPTPs may be further subdivided into four types based on structural motifs within their extracellular segments.

One example of RPTPs are the leukocyte common antigens (LCA) (Ralph, S. J., *EMBO J.*, 6:1251–1257 (1987); Charbonneau, H., et al., *Proc. Natl. Acad. Sci. USA*, 85:7182–7186 (1988)). LCA, also known as CD45, T200 and Ly-5 (reviewed in Thomas, M. L., *Ann. Rev. Immunol.* 7:339–369 (1989)) comprises a group of membrane glycoproteins expressed exclusively in hemopoietic (except late erythroid) cells, derived from a common gene by alternative splicing events involving the amino terminus of the proteins.

Other examples of RPTPs are the LCA-related protein, LAR (Streuli, M. et al., *J. Exp. Med.*, 168:1523–1530 (1988)), and the LAR-related *Drosophila* proteins DLAR and DPTP (Streuli, M., et al., *Proc. Natl. Acad. Sci. USA*, 86:8698–8702 (1989)). Jirik et al. screened a cDNA library derived from the human hepatoblastoma cell line, HepG2, with a probe encoding the two PTPase domains of LCA (*FASEB J.* 4:A2082 (1990), abstr. 2253) and discovered a cDNA clone encoding a new RPTP, named He-PTP. The HePTP gene appeared to be expressed in a variety of human and murine cell lines and tissues.

A large number of members of the RPTP family, called type II RPTPs, display an extracellular domain containing a combination of Ig-domains and fibronectin type III repeats (Fn-III), features typically encountered in cell adhesion molecules (CAMs) (Gebbink, M. F. B. G. et al., 1991 FEBS Lett; 290:123–130; Streuli, M. et al., 1988 J. Exp. Med. 168: 1523–1530). An analysis of the expression patten of several R-PTPases in the developing *Drosophila* CNS suggests some function of these molecules in aspects of axon guidance and outgrowth (Tian, S. S. et al., 1991 Cell 67:675–685; Yang, X. et al., 1991. Cell 67:661–673), an observation winch might be related to the ability of R-PTPases to control the activity of src-family tyrosine kinases (Mustelin, T. et al., 1989 Proc. Natl. Acad. Sci. USA 86:6302–6306; Ostergaard, H. L. et al., 1989 Proc. Natl. Acad. Sci. USA 86:8959–8963; Zheng, X. M. et al., 1992 Nature 359:336–339). Other studies have raised the possibility that certain R-PTPases may function as tumor suppressor genes, e.g. by controlling contact inhibition (LaForgia, S. et al., 1991 *Proc. Natl. Acad. Sci. USA* 88:5036–5040). Elevation of cellular phosphotyrosine may occur through mechanisms other than the activation of a tyrosine kinase itself. For instance, expression of the v-crk oncogene, though not a tyrosine kinase, induces the phosphorylation of tyrosine residues through a poorly understood mechanism (Mayer, B. J. et al. (1988) *Nature* 332, 272–275). Potentially, such an outcome could result from either mutation of the substrate or through a general decrease in cellular phosphatase activity, especially in view of the normally high turnover rate of cellular tyrosine-phosphate (Sefton, B. M. et al. (1980) *Cell* 20:807–816). The latter possibility is suggested by the demonstration that tyrosine phosphatase inhibitors can "reversibly transform" cells (Klarlund, J. K. Cell 41: 707–717 (1985)). PTPases could therefor act as recessive oncogenes.

While we are beginning to understand more about the structure and diversity of the PTPases, much remains to be learned about their cellular functions. Thus, a better understanding of, and an ability to control, phosphotyrosine metabolism, requires knowledge not only the role of PTKase activity, but the action of PTPase enzymes as well. It is clear in the art that further delineation of structure-function relationships among these PTPases and RPTP membrane receptors are needed to gain important understanding of the mechanisms of cell growth, differentiation, and oncogenesis.

3. SUMMARY OF THE INVENTION

The present inventors have conceived of a role for RPTPs in cellular control mechanisms, both as potential anti-oncogenes, and as effectors in a newly discovered mechanism of transmembrane signalling. They therefore undertook a search for individual RPTP genes and proteins in mammals, including humans, which are potentially involved in such processes, and describe herein the identification of a novel, widely expressed member of the RPTP family, RPTPκ, in both mice and in humans which has a transmembrane topology. The novel human RPTPκ disclosed herein consists of two associated subunits whose expression is modulated by cell-to-cell contact, and, in a manner analogous to receptor tyrosine kinases, is subject to direct regulation by extracellular ligands which bind to the extracellular portion. Further, as is demonstrated in the Working Example presented in Section 15, infra, RPTPκ is shown to homophilically bind other RPTPκ molecules.

The present invention thus provides a mammalian, preferably a human, receptor-type protein tyrosine phosphatase-κ (RPTPκ) protein or glycoprotein molecule, a functional derivative of the RPTPκ, or a homolog of the RPTPκ in another mammalian species. When the RPTPκ molecule is of natural origin, it is substantially free of other proteins or glycoproteins with which it is natively associated. RPTPκ is naturally expressed in mammalian brain and is developmentally and anatomically regulated. It is also expressed in other mammalian tissues. The RPTPκ molecule of the present invention may also be prepared by chemical synthesis or by or recombinant means. Thus, the substantially pure RPTPκ protein or glycoprotein of the present invention may be produced by biochemical purification of the protein or glycoprotein of natural origin or by production using chemical synthesis or by recombinant expression in prokaryotic or eukaryotic hosts.

Figure 3:
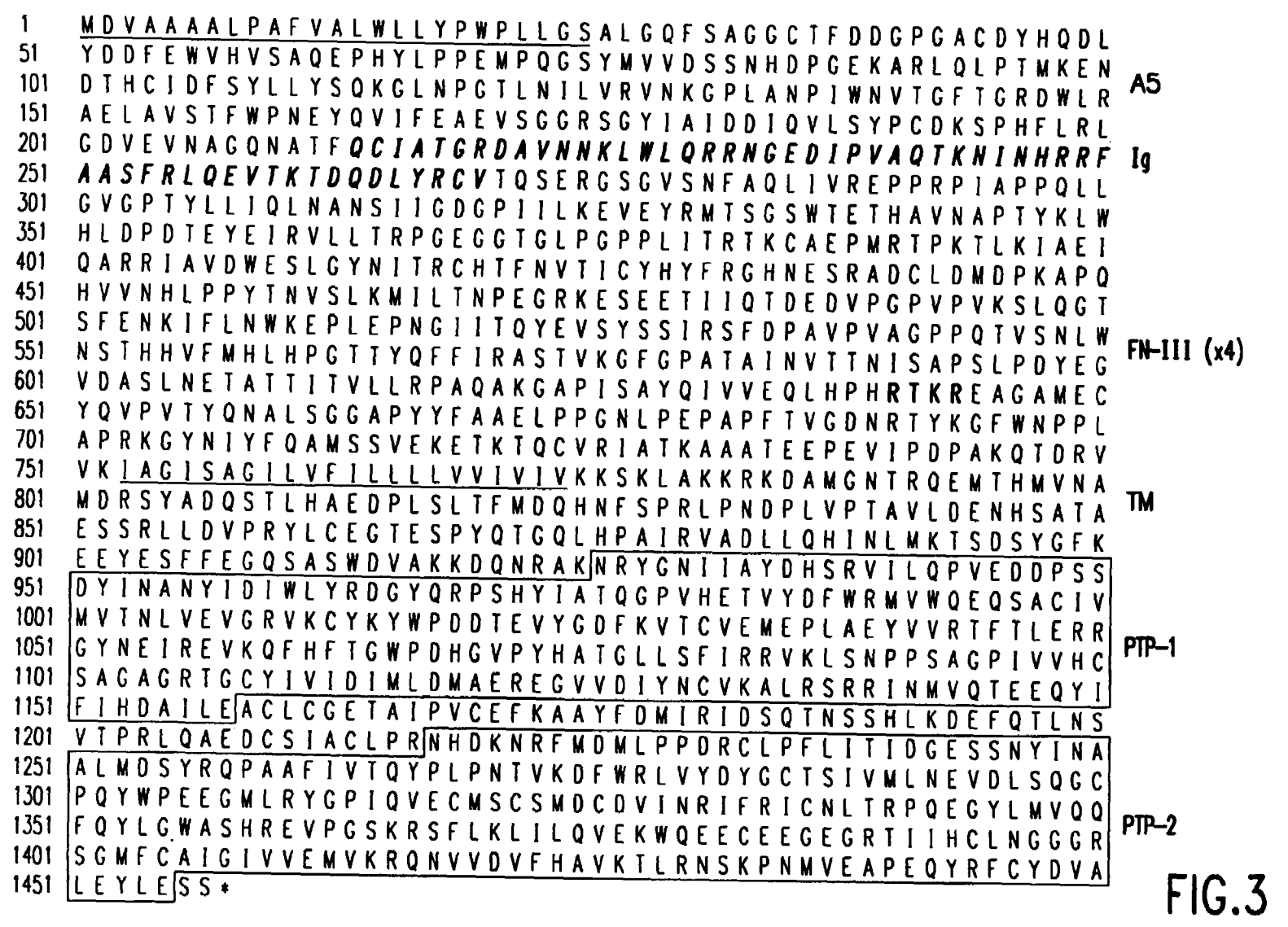

In particular, the invention is directed to a mammalian RPTPκ protein or glycoprotein having the amino acid sequence of RPTPκ shown in FIG. 3 (SEQ ID NO:1). In another embodiment is provided a functional derivative thereof. Preferably, the RPTPκ is of human origin, and has the amino acid sequence SEQ ID NO:2, as shown in FIGS. 15A–15E.

The invention is further directed to a nucleic acid molecule, preferably DNA, which may consist essentially of a nucleotide sequence encoding a mammalian RPTPκ having the nucleotide sequence (SEQ ID NO:3) (FIG. 1A–1H). Preferably, the nucleic acid molecule consists essentially of a nucleotide sequence encoding human RPTPκ and having the nucleotide sequence (SEQ ID NO:4) or encodes a functional derivative thereof. The DNA molecule is preferably cDNA or genomic DNA. The invention is further directed to the DNA molecule in the form of an expression vehicle, as well as prokaryotic and eukaryotic hosts transformed or transfected with the DNA molecule.

Also included in the present invention is a process for preparing a RPTPκ protein or glycoprotein, or a functional derivative thereof, comprising:
(a) culturing a host capable of expressing the protein, glycoprotein or functional derivative under culturing conditions,
(b) expressing the protein, glycoprotein or functional derivative; and
(c) recovering the protein, glycoprotein or functional derivative from the culture.

This invention is also directed to an antibody, either polyclonal, monoclonal, or chimeric, which is specific for the RPTPκ protein or glycoprotein.

This invention is also directed to a method for detecting the presence of nucleic acid encoding a normal or mutant RPTPκ in a cell or in a subject, comprising:
(a) contacting a cell or an extract thereof from the subject with an oligonucleotide probe encoding at least a portion of a normal or mutant RPTPκ under hybridizing conditions; and
(b) measuring the hybridization of the probe to the nucleic acid of the cell, thereby detecting the presence of the nucleic acid, preferably DNA.

The DNA can be selectively amplified, using the polymerase chain reaction, prior to assay.

The invention is further directed to a method for detecting the presence, or measuring the quantity of RPTPκ in a cell or cells, comprising:
(a) contacting said cell or an extract thereof with an antibody specific for an epitope of RPTPκ; and
(b) detecting the binding of the antibody to the cell or extract thereof, or measuring the quantity of antibody bound, thereby detecting the presence or measuring the quantity of the RPTPκ.

The present invention is also directed to methods for identifying and isolating a compound capable of binding to RPTPκ from a chemical or biological preparation comprising:
(a) attaching RPTPκ, or the ligand-binding portion thereof, to a solid phase matrix;
(b) contacting the chemical or biological preparation with the solid phase matrix allowing the compound to bind, and washing away any unbound material;
(c) detecting the presence of the compound bound to the solid phase matrix; and, for purposes of isolation,
(d) eluting the bound compound, thereby isolating the compound.

Further, the present invention includes a method for identifying an agent capable of stimulating or inhibiting the phosphatase enzymatic activity of RPTPκ, comprising:
(a) contacting the agent with the RPTPκ in pure form, in a membrane preparation, or in a whole live or fixed cell;
(b) incubating the mixture in step (a) for a sufficient interval;
(c) measuring the enzymatic activity of the RPTPκ;
(d) comparing the enzymatic activity to that of the RPTPκ incubated without the agent, thereby determining whether the agent stimulates or inhibits the enzymatic activity.

Still further, the invention provides methods for inhibiting the homophilic binding of Type II RPTP, preferably the homophilic binding of RPTPκ, provides methods for identifying agents capable of inhibiting such Type II RPTP homophilic binding, and methods for inhibiting endogenous Type II RPTP homophilic binding in mammalian subjects.

4. DESCRIPTION OF THE FIGURES

FIG. 1A–1H shows the complete nucleotide sequence SEQ ID NO: 3 and amino acid sequence SEQ ID NO: 1 of murine RPTPκ. The signal peptide, A5 homology region, transmembrane domain, and PTPase domains are designated by brackets.

FIG. 2 is a schematic representation of the various RPTPκ cDNA clones isolated, and the proposed domain structure of the RPTPκ protein. Translational start and stop codons as well as restriction sites mentioned in the text are indicated. The vertical arrow indicates the position of the furin cleavage site. TM: transmembrane segment.

FIG. 3 shows the predicted amino acid sequence (SEQ ID NO: 1) of the RPTPκ precursor protein. The putative signal peptide and transmembrane (TM) segment are underlined. The two tandem phosphatase domains are boxed (PTP-1, PTP-2). The proteolytic cleavage site (RTKR, residues 640–643 of SEQ ID NO: 1) is printed in bold, and the Ig-like domain (Ig, 214–270) shown in bold italic characters. A5: homology to A5 surface protein (Takagi, S. et al., 1991 Neuron 7:295–307); FN-III: fibronectin type III repeats. The Genbank accession number for the cDNA sequence is L10106.

FIG. 4 shows a proposed alignment of the four FN-III repeats of RPTPκ (residues 296–383 of SEQ ID NO: 1, residues 392–473 of SEQ ID NO: 1, residues 493–578 of SEQ ID NO: 1, and residues 596–679 of SEQ ID NO: 1, respectively, in order of appearance) and domain 7 of human fibronectin (SEQ ID NO: 5) (Kornblihtt, A. R. et al., 1985 EMBO J. 4:17551759). Residues most typically conserved in FN-III repeats are highlighted in bold. Residues identical in three or more out of the five aligned sequences are indicated with an asterisk. This region of the protein also contains clearly detectable homology to LAR, *Drosophila* PTPase 10D, and *Drosophila* neuroglian, all of which have been reported to contain FN-III repeats.

FIG. 5 shows an alignment of the N-terminal domains of RPTPκ (residues 33–189 of SEQ ID NO: 1) and mRPTPμ (SEQ ID NO: 6) with the cell surface protein A5 (SEQ ID NO: 7) (Takagi et al., supra). Numbers indicate the first residue of the respective proteins shown in the alignment. Residues marked as consensus are identical between A5 and RPTPκ, or between A5 and mRPTPμ. Conservative substitutions are present but not shown. Residues in bold (C,W) define a possible Ig-like domain structure.

Figure 6:
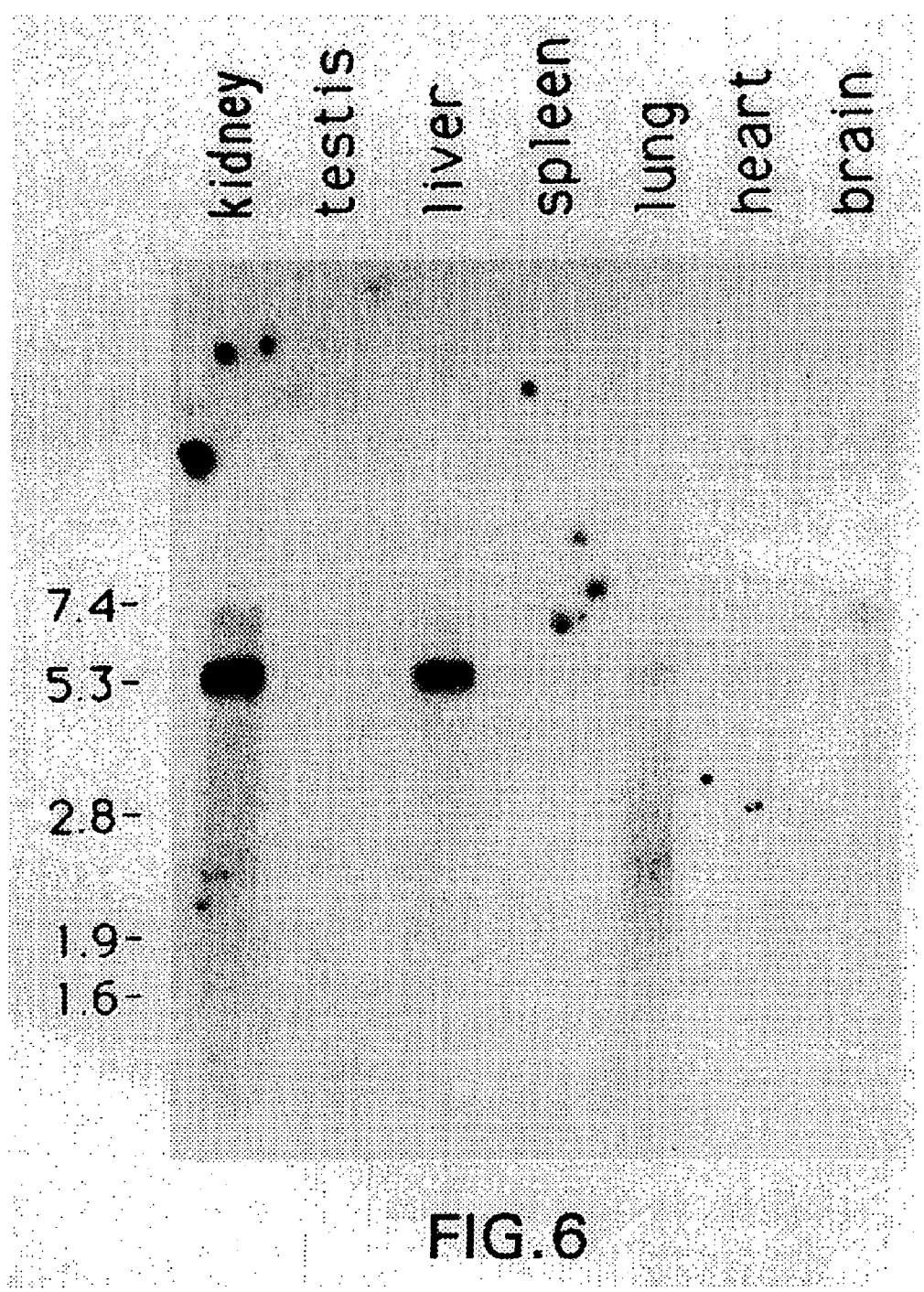

FIG. 6 shows the expression of RPTPκ mRNA in adult tissues using Northern blot analysis of poly(A)+RNA from various mouse tissues. The entire cDNA fragment from clone λ604 was used as a probe. A similar pattern of hybridization was seen using as a probe the λ50 cDNA clone and the N-terminal half of the λ35 cDNA clone. Positions of RNA molecular weight markers, in kb, are indicated on the left side.

Figure 7:
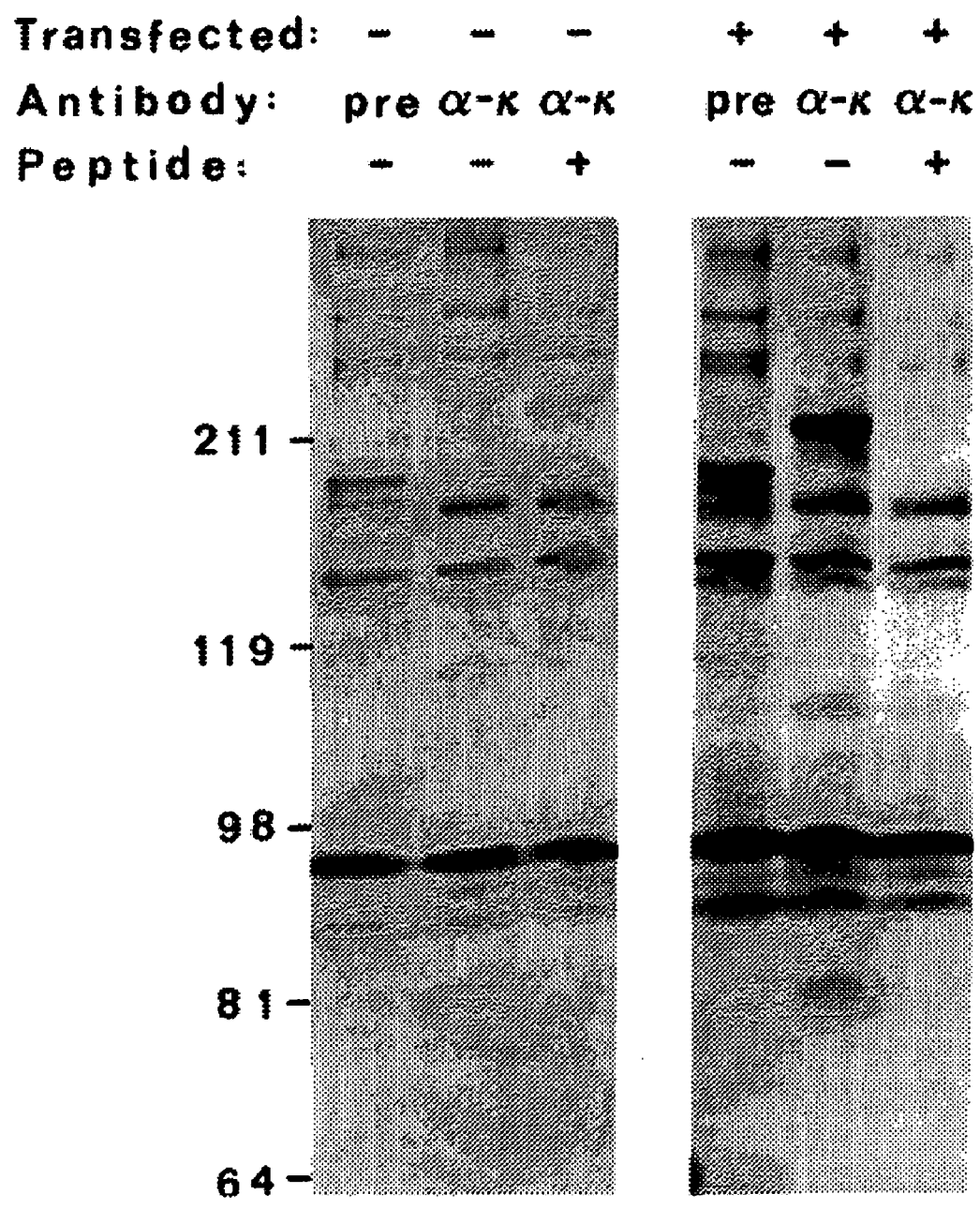

FIG. 7 is a gel pattern showing the immunoprecipitation of the RPTPκ protein. HeLa cells transiently transfected by the calcium phosphate technique with an RPTP-ic expression vector (+) or an empty expression vector (−) were analyzed by radio-immunoprecipitation using antiserum 116 directed against a synthetic peptide corresponding to residues 60 to 76 in the extracellular domain. The immunoprecipitation was performed in the absence (−) or presence (+) of 20 µg of the immunogenic peptide (a-κ: anti RPTPκ antiserum 116; pre: corresponding preimmune serum). Positions of protein molecular weight standards (expressed in kDa) are indicated on the left side of the autoradiogram.

Figure 8:
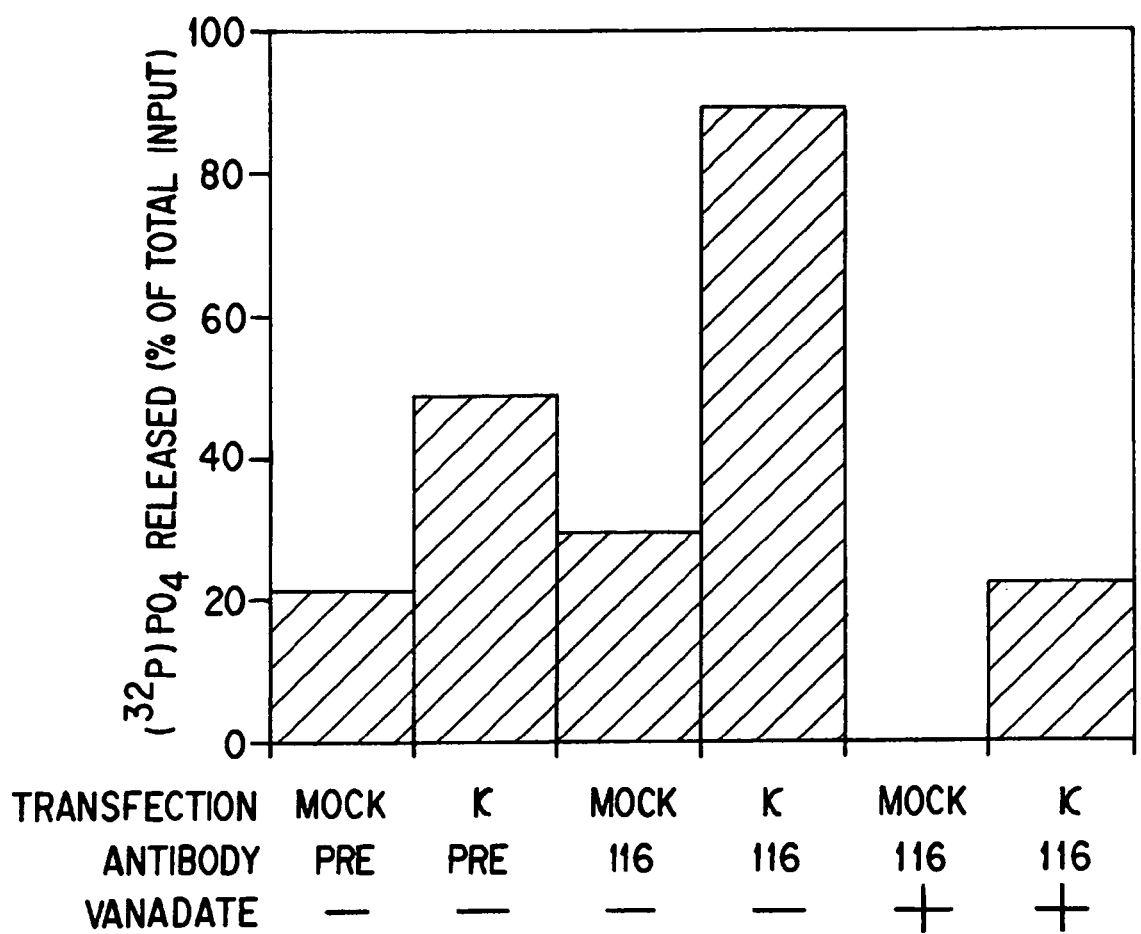

FIG. 8 shows the protein tyrosine phosphatase activity of anti-RPTPκ immunoprecipitates. The RPTPκ protein was immunoprecipitated from transiently transfected COS cells using anti-N-terminal antibody 116 or corresponding preimmune serum. The PTPase activity in the immune complexes was analyzed in the absence (−) or presence (+) of vanadate. The amount of radioactivity released as inorganic phosphate is expressed as the percentage of the total input radioactivity. A representative of several experiments is shown.

Figure 9:
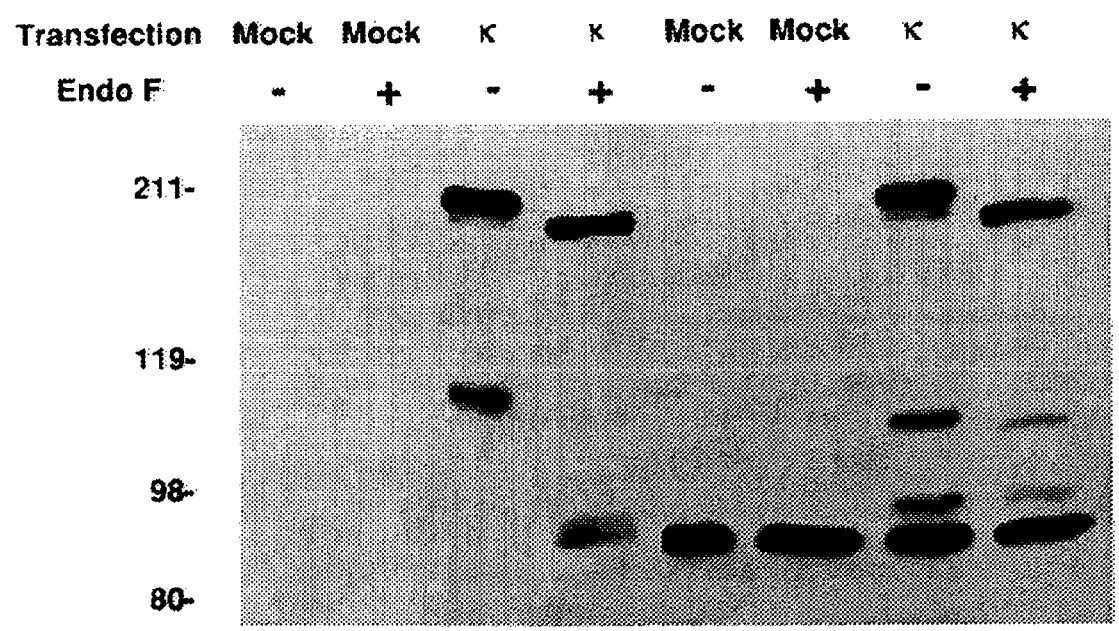

FIG. 9 shows RPTPκ immunoreactive species in COS cells, and effect of Endo F treatment on SDS-PAGE mobility. Total lysates from mock or RPTPκ transfected COS cells were treated or not with Endo F. The lysates were resolved by SDS-PAGE and immunoblotted with anti-N-terminal antibody 116 (left panel) or anti-cytoplasmic antibody 122 (right panel). The 95 kDa band in panel B also seen in mock-transfected cells is presumably due to fortunitous reactivity of antiserum 122 and not relevant to the analysis. No such protein species was detectable using an antiserum raised against the same antigen in a different rabbit.

Figure 10:
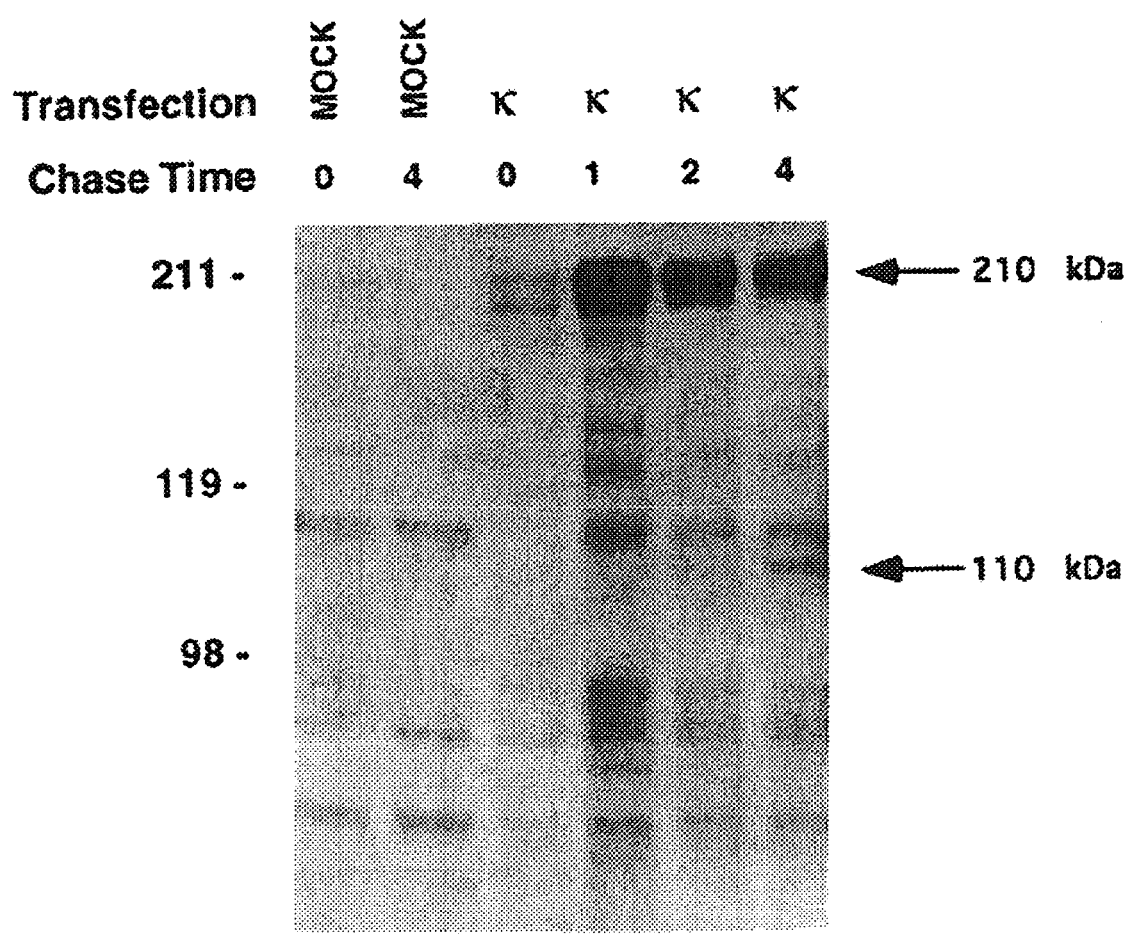

FIG 10 shows results of a pulse-chase analysis of RPTPκ processing. Mock-transfected with a wild type RPTPκ expression vector (lanes 3 to 6) were metabolically labeled with [$^{35}$S]-methionine (200 [μCi/ml] for 15 minutes ("pulse") and chased for the time-periods indicated. Immunoprecipitatin was performed using antiserum 116. Arrows indicate the positions of the 210 kDa RPTPκ precursor and the 110 kDa N-terminal cleavage product.

Figure 11:
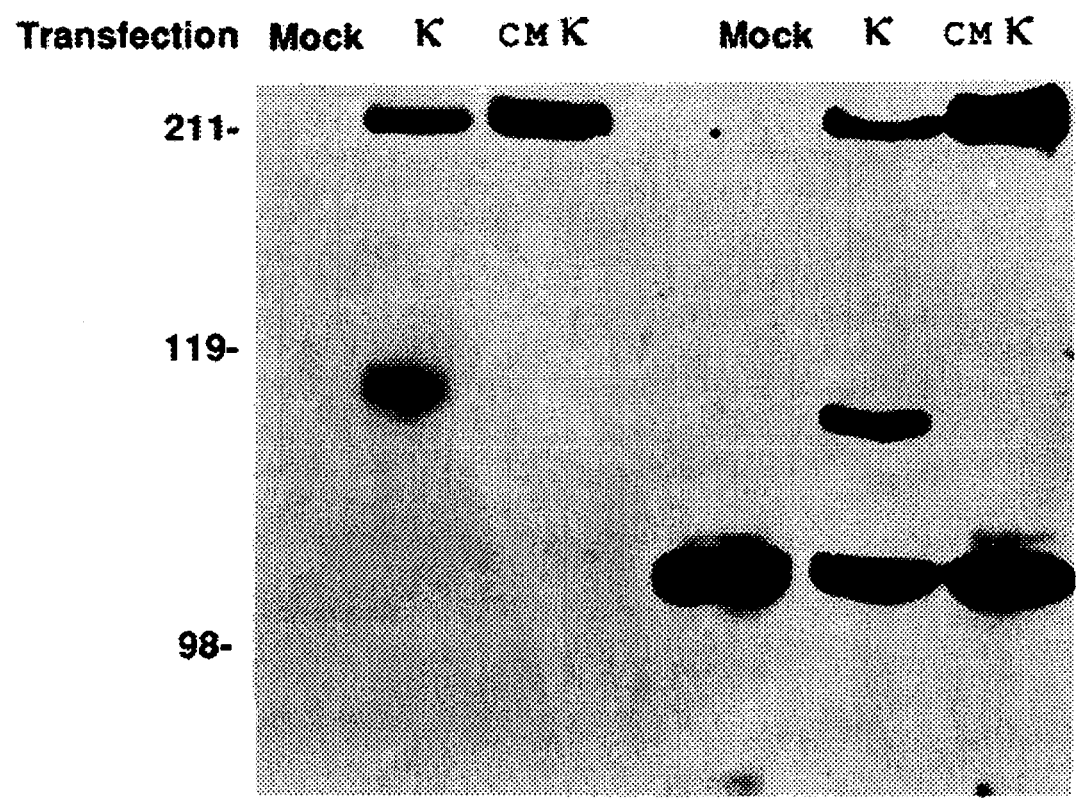

FIG. 11 shows the effect of mutagenesis of the furin cleavage motif RTKR (SEQ ID NO: 12) on RPTPκ processing. Total lysates from mock-transfected COS cells, cells expressing wt RPTPκ, or RTKR (CM κ) (SEQ ID NO: 12) were resolved by SDS-PAGE. Immunoblotting was performed using anti-N-terminal antiserum 116 (left panel), or anti-cytoplasmic antiserum 122 (right panel).

Figure 12:
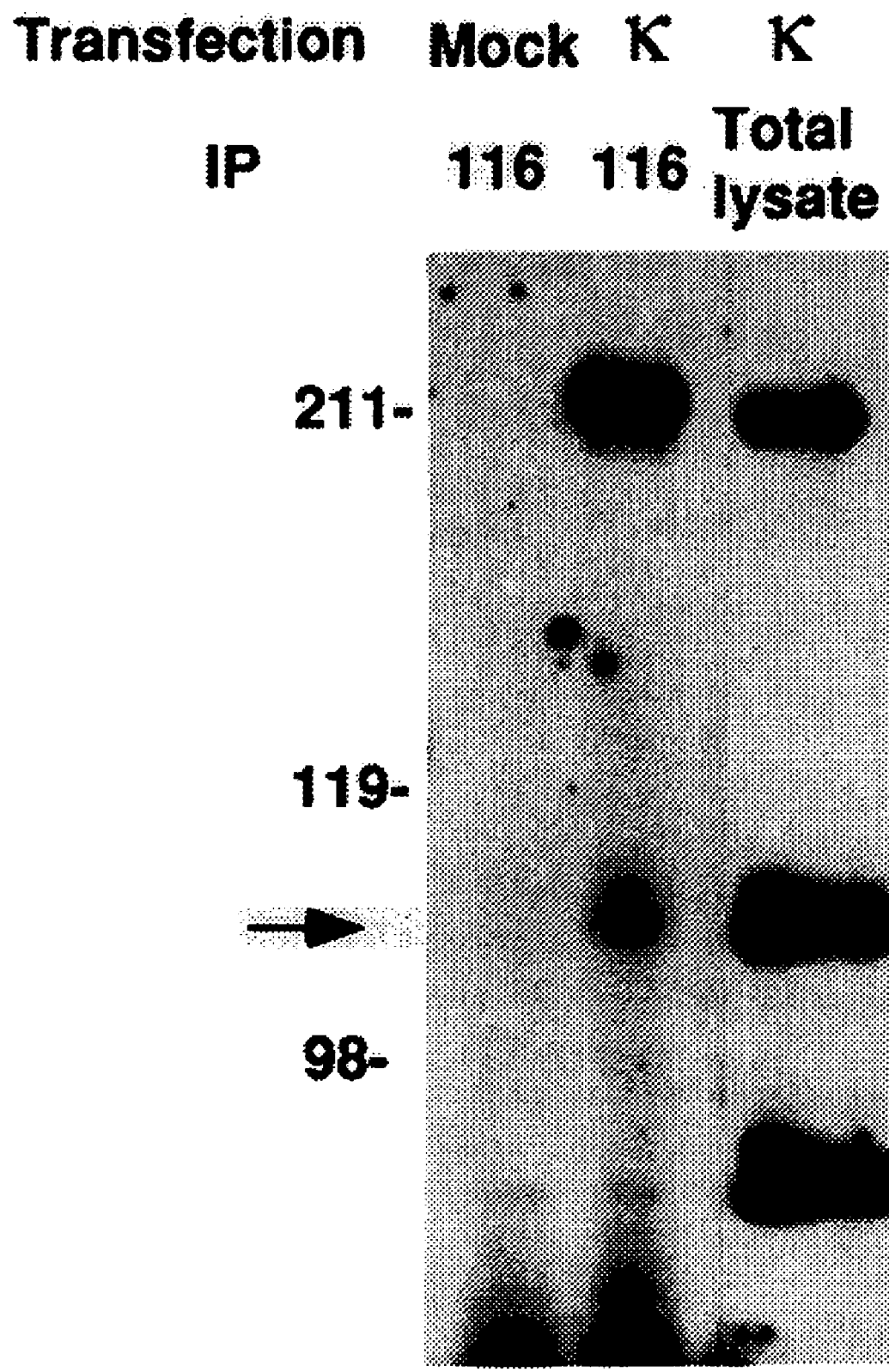

FIG. 12 shows the co-immunoprecipitation of the RPTPκ processing products. Total lysate from mock or wild type RPTPκ transfected COS cells was subjected to immunoprecipitation using anti-N-terminal antiserum 116, and the precipitate inununoblotted with anti-cytoplasmic antiserum 122. As a control, total lysate from RPTPκ transfected cells was loaded in the right lane on the immunoblot.

Figure 13A:
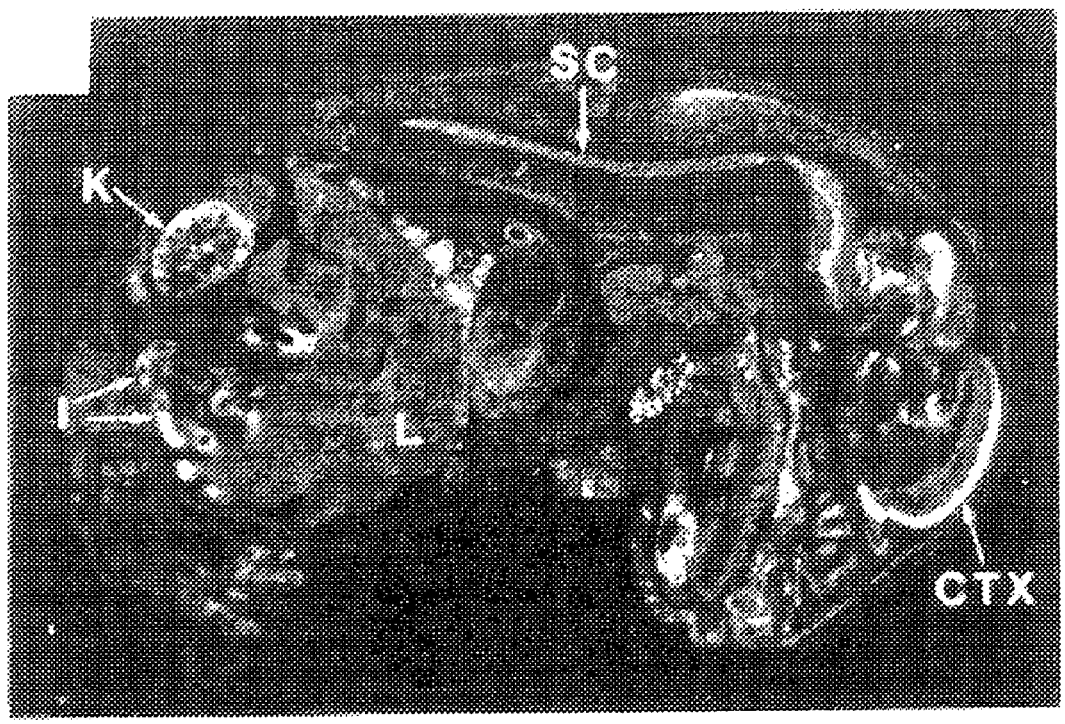
Figure 13B:
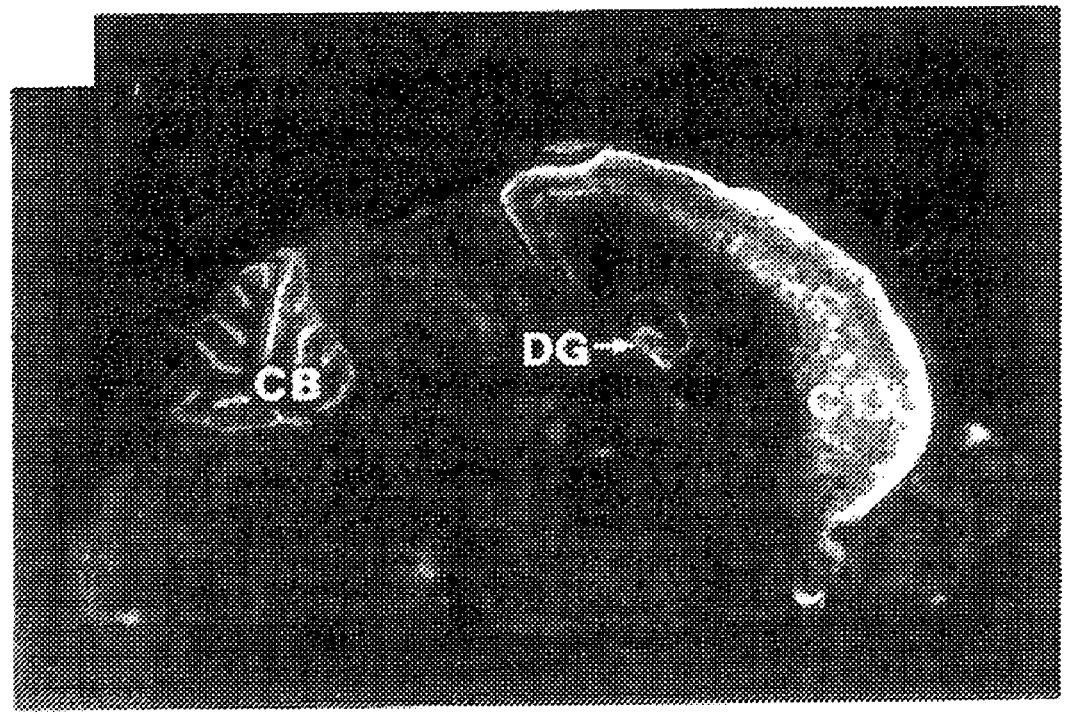

FIGS. 13A–13B is a series of micrographs showing the in situ hybridization analysis of RPTPκ expression during development and in the adult CNS. 13A panel shows localization of RPTPκ mRNA in the rat at embryonic day 18. CTX, cerebral cortex; MB, midbrain; SC, spinal cord; L, liver; K, kidney; I, intestine. 13B panel shows localization of RPTPκ mRNA in a sagittal section of rat brain at postnatal day 6. CTX, cerebral cortex; CB, cerebellum; DG, dentate gyms. In the cerebral cortex, particularly in the occipital region, the labeling is not uniform in all the cortical cell layers. In the hippocampal formation labeling is more intense in the dentate gyms and in CA3. In the cerebellum, the most intense labeling is seen in the external granular cell layer.

Figure 14:
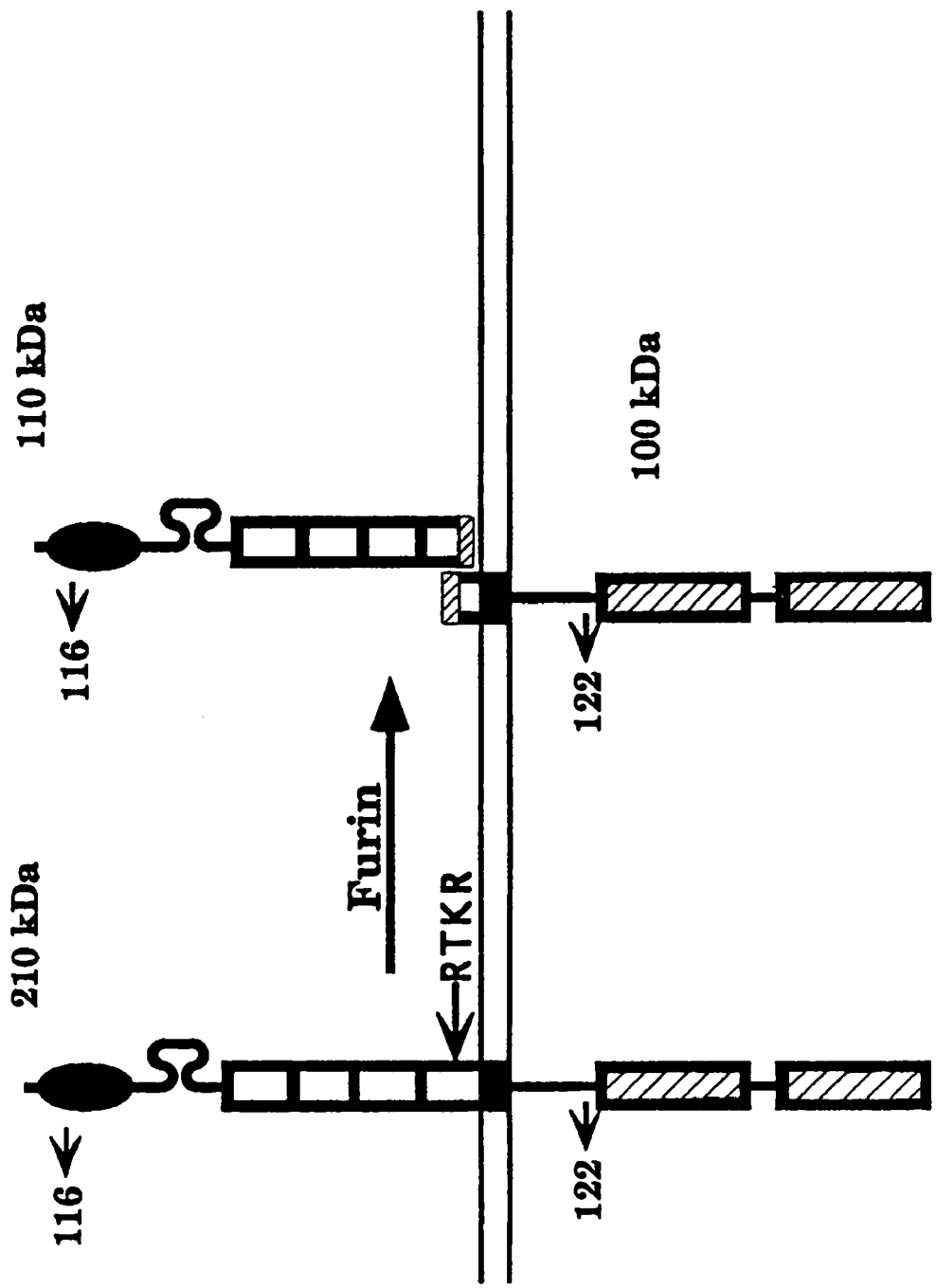

FIG. 14 is a molecular model describing the processing of the R-PTP-κ precursor protein. A furin-like endoprotease cleaves the 210 kDa precursor protein, after which both cleavage products (110 and 100 kDa) remain associated. No suggestions as to the mechanism of association are intended. The numerals 116 and 122 designate the sites of epitopes recognized by antisera described in the text. The RTKR peptide is shown in SEQ ID NO: 12.

FIGS. 15A–15E shows the nucleotide sequence of the human RPTPκ (SEQ ID NO:4), designated MCP7, and its derived amino acid sequence (SEQ ID NO:2).

FIGS. 16A–16B. A comparison of the amino acid sequence or RPTPκ (SEQ ID NO:2) to the amino acid sequence of hRPTPμ (SEQ ID NO:8). Lack of designation of an amino acid in hRPTPμ indicates identity to the MCP7 sequence. The putative signal peptide is overlined and dotted; th e MAM domeain is boxed with white background; the Ig-like domain is overlined with a shaded bar; the FN-III repeats are indicated with brakets above them; the RTKR eleavage site is underlined; the transmembrane domain is indicated with asterisks; and the PTPase domains are boxed. Both PTPase domains are shown with a shaded background.

Figure 17:
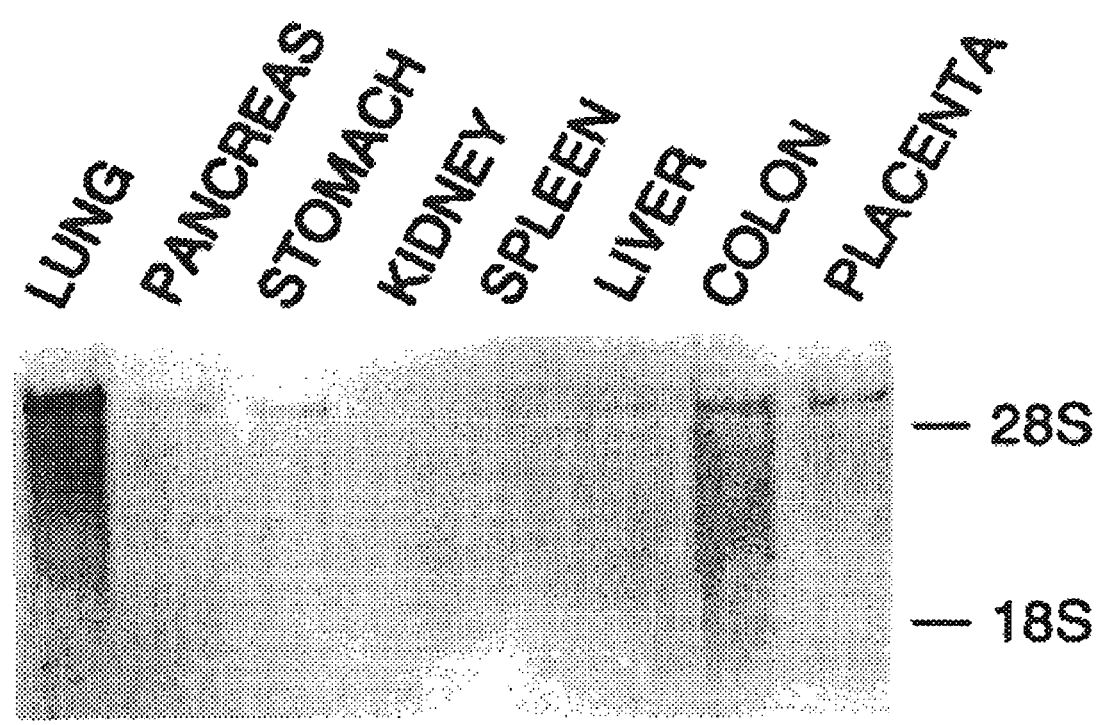

FIG. 17 shows a Northern blot analysis of MCP7 mRNA from human tissues. Poly(A)+RNA (4 μg per lane) prepared from the indicated tissues was probed with a $^{32}$p-labeled fragment corresponding to the extracellular domain of MCP7. The blots were applied for a 5 day exposure using an intensifying screen.

Figure 18:
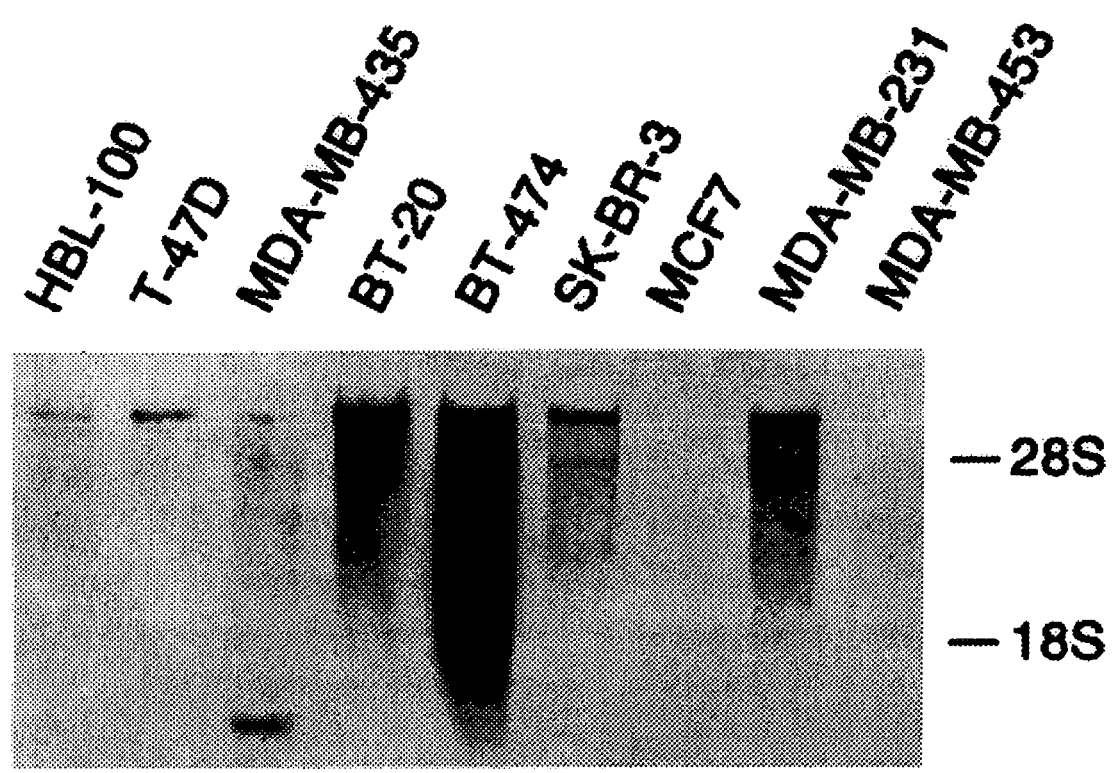

FIG. 18 shows a Northern blot analysis of MCP7 mRNA from several different human breast cancer cell lines. Poly (A)+RNA (4 μg per lane) prepared from the indicated cell line was probed as in FIG. 15 and the blots similarly exposed.

Figure 19A:
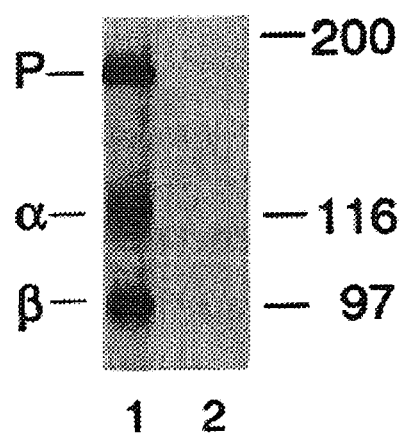
Figure 19B:
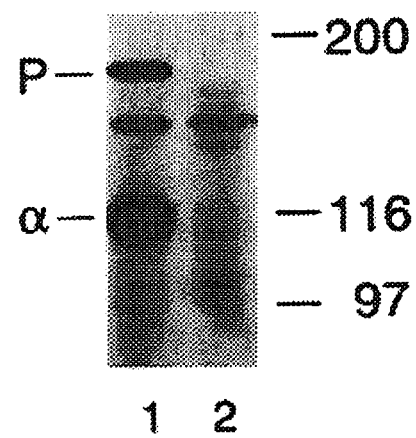

FIGS. 19A–19B shows gel patterns indicating the transient expression of MCP7 mRNA in transfected cells. Cells of the 293 line were transfected with a MCP7 expression vector (or an empty vector as a control), metabolically labeled for 24 hours with [$^{35}$S] methionine and incubated with an anti-N-terminal antiserum 116. Cells were washed, lysed and protein-antibody complexes were removed by protein-A sepharose. Left panel shows a SDS-PAGE gel of immunoprecipitates. 19B panel shows Western blots of SDS-PAGE gels of lysates of cells transfected by MCP7-CMV (lane 1) or "empty" CMV (lane 2) and immunoblotted with the anti-N-terminal antiserum 116.

Figure 20A:
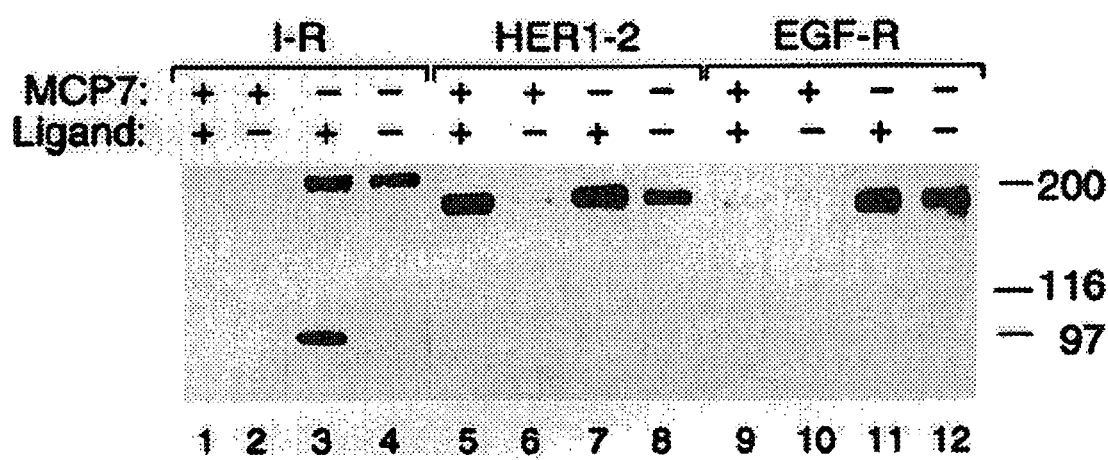
Figure 20B:
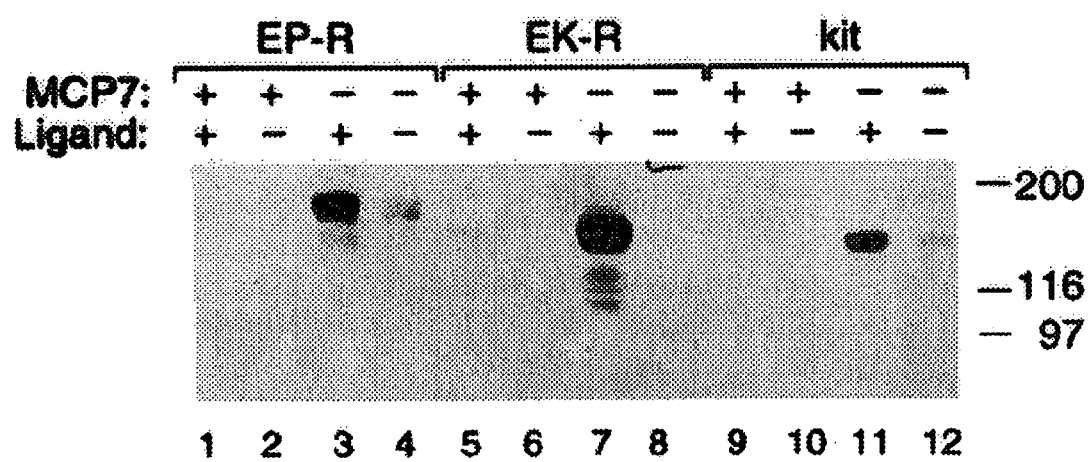

FIGS. 20A–20B shows Western blot patterns indicating co-expression of MCP7 with different RTKs. Semiconfluent 293 cells were transfected with expression plasmids encoding the indicated RTK together with either an equal amount of MCP7 expression vector or a control plasmid. After stimulation with the appropriate ligand: stem cell factor (SCF) for the p145.sup.c-kit RTK; epidermal growth factor for all other RTKs; insulin for I-R, cells were lysed, aliquots run on SDS-PAGE and transferred to nitrocellulose. Proteins were immunoblotted with anti-phosphotyrosine antibody 5E.2. Molecular mass markers are indicated.

Figure 21A:
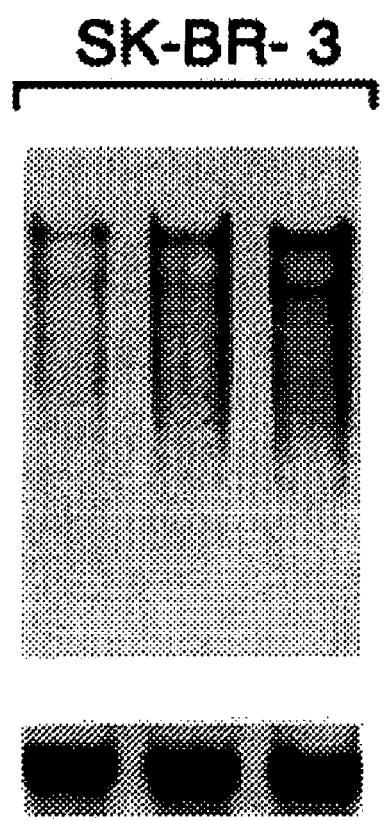
Figure 21B:
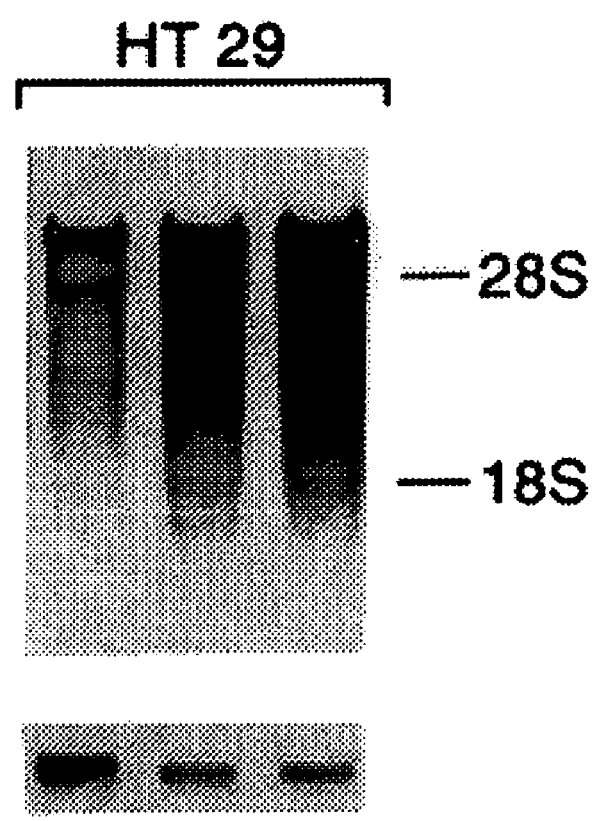

FIGS. 21A–21B shows Northern blots indicating the relationship between MCP7 mRNA levels and the state of cell confluence in SK-BR-3 cells (left panel) and HT-29 cells (right panel) in culture. Poly(A)+ RNA (4 μg per lane) was prepared from cells obtained at different levels of confluence (lanes 1 and 4: 40%; lanes 2 and 5: 70%, lane 3 and 6: 100%) and was probed with a $^{32}$P-labeled DNA probe corresponding to the extracellular domain of MCP7 (upper blots) and with a fragment coding for GAPDH (lower blots).

FIG. 22A. Expression of the R-PTPκ protein in transfected S2 cells. Detergent lysates were prepared from transfected cells, resolved by SDS-PAGE, and immunoblotted with an antiserum directed against the extracellular domain of the R-PTPκ protein (Y.-P. Jiang et al. Mol. Cell. Biol. 13, 2942 (1993)). Lanes: 1, R-PTPκ anti-sense transfected cells, not heat-shocked; 2, anti-sense transfected after heat-shock; 3, sense transfected cells, not heat-shocked; 4, sense-transfected cells after heat-shock; 5, lysate from COS cells transiently transfected with an R-PTPκ expression vector (Y.-P. Jiang et al. Mol. Cell. Biol. 13, 2942 (1993)). Molecular weight standards are indicated in kilodaltons.

The entire RPTPκ cDNA was introduced in both orientations as a HpaI/EcoRV fragment into the HpaI site of a derivative of the pCasper expression vector containing the hsp70 promoter, and the resulting construct co-transfected with the pPC4 plasmid (conferring α-amanitin resistance) into S2 cells using calcium phosphate precipitation. Pools of stably transfected cells were selected in the presence of 5 μg/ml α-amanitin for three weeks. Transfected cells were heat-shocked at 37° C. for 30 minutes and allowed to recover for 2 hours. Adherent cells were collected, and washed twice in BSS (Kramer, H. et al., 1991, Nature 352:207; Snow, P. et al., 1989, Cell 59:313).

Figure 22B:
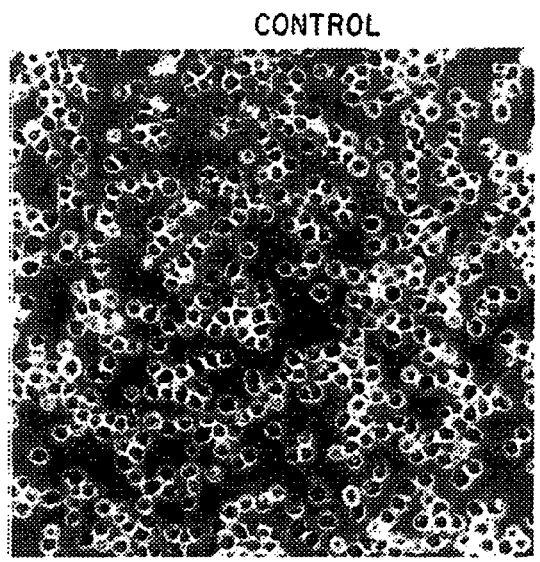

FIG. 22B. Photographs of transfected cell populations after heat-shock induction and aggregation for 2 hours. Left panel, control (anti-sense transfected) cells; right panel, cells transfected with an expression vector carrying the R-PTPκ cDNA in the sense orientation; insert: higher magnification of a typical aggregate.

Figure 22C:
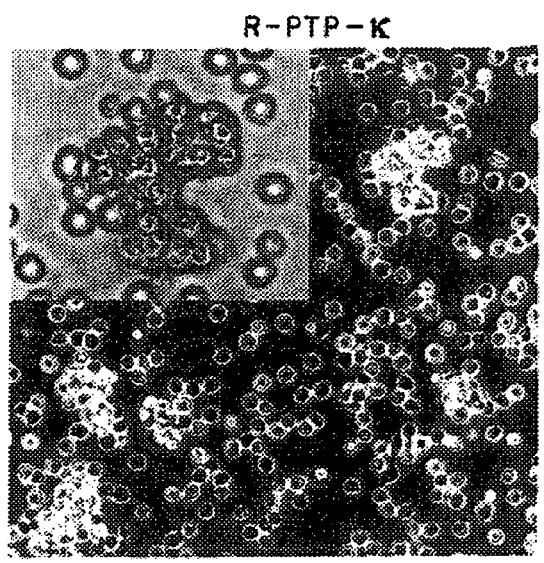

FIG. 22C. Time-course and quantitation of aggregation by Coulter-counting of above-threshold particles. Open squares: anti-sense vector transfected cells, uninduced; full squares, idem, induced; open circles, cells transfected with an expression vector containing the R-PTPκ cDNA in the sense orientation, uninduced; full circles, sense, induced. Standard errors are indicated by error bars.

Adherent, transfected cells were collected, washed twice with BSS, resuspended in BSS at a concentration of $4 \times 10^6$ cells/ml, and incubated in Coulter-Counter vials on a rotary shaker for 2 hours at 100 rpm at room temperature. For each time-point, 1 ml was counted using the Coulter-counter with the following settings: 1/amplification=4; threshold=10; 1/aperture current=32.

Figure 22D:
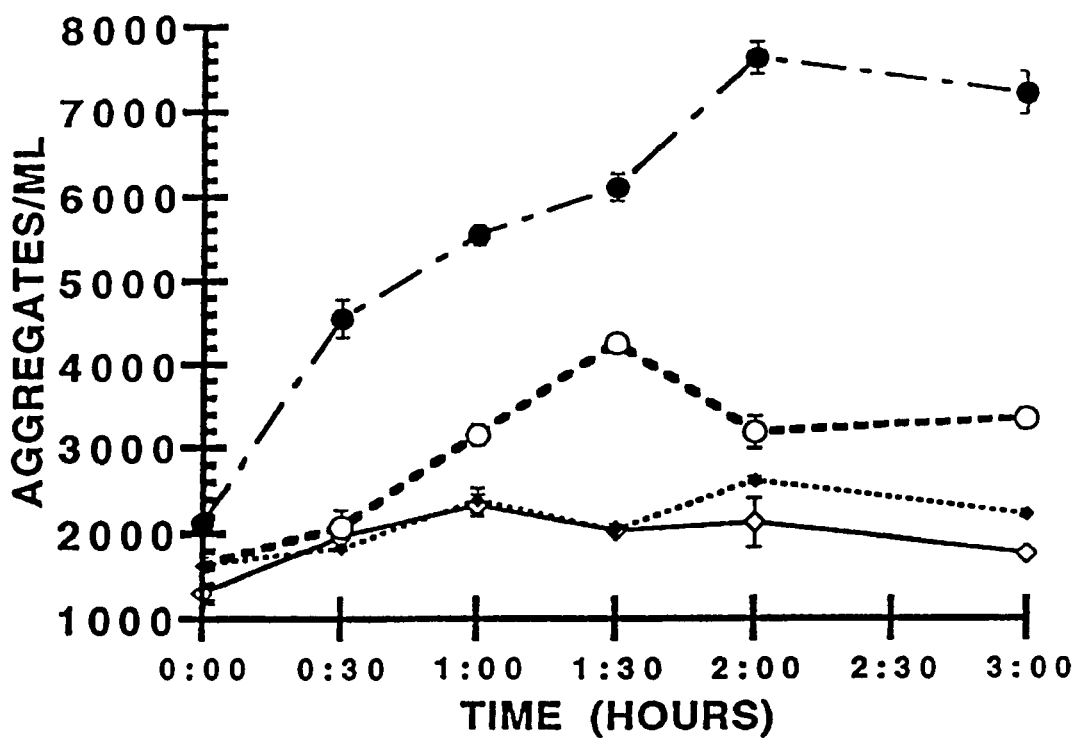

FIG. 22D. Effect of deletion of the intracellular domain of the R-PTPκ protein, and mutation of the furin cleavage site. Parental S2 cells were transiently transfected with expression vectors encoding an R-PTPκ cDNA in which the furin cleavage site had been mutated (CM) (Y.-P. Jiang et al. Mol. Cell. Biol. 13, 2942 (1993)), a cDNA encoding a catalytically inactive deletion mutant of R-PTPκ lacking most of the intracellular (PTPase) domain (Δ-PTP), or a wt R-PTPκ cDNA (wt). For the deletion mutant, a cDNA encoding a truncated, catalytically inactive form (Δκ) of RPTPκ was constructed by restriction digestion with BspEI and Klenow fill-in of the wild type cDNA. This leads to the introduction of a stop codon after amino acid residue 1083, and the generation of a protein lacking the cysteine residues essential for catalysis in the two intracellular catalytic homology domains of RPTPκ. Cells were heat-induced 72 hours after transfection, subjected to aggregating conditions for 2 hours, and above-threshold aggregates counted with a Coulter-counter. Error bars indicate standard errors. Transfected, but non heat-shock induced cells behaved as untransfected parental cells. The apparent differences in aggregation intensity between the different forms of R-PTPκ may reflect protein expression levels. The numbers provided by Coulter-counter counting actually provide an underestimation of the amount of aggregation as determined by visual inspection and counting of aggregates, since only large particles above a certain threshold size are scored by the Coulter-Counter.

Figure 22E:
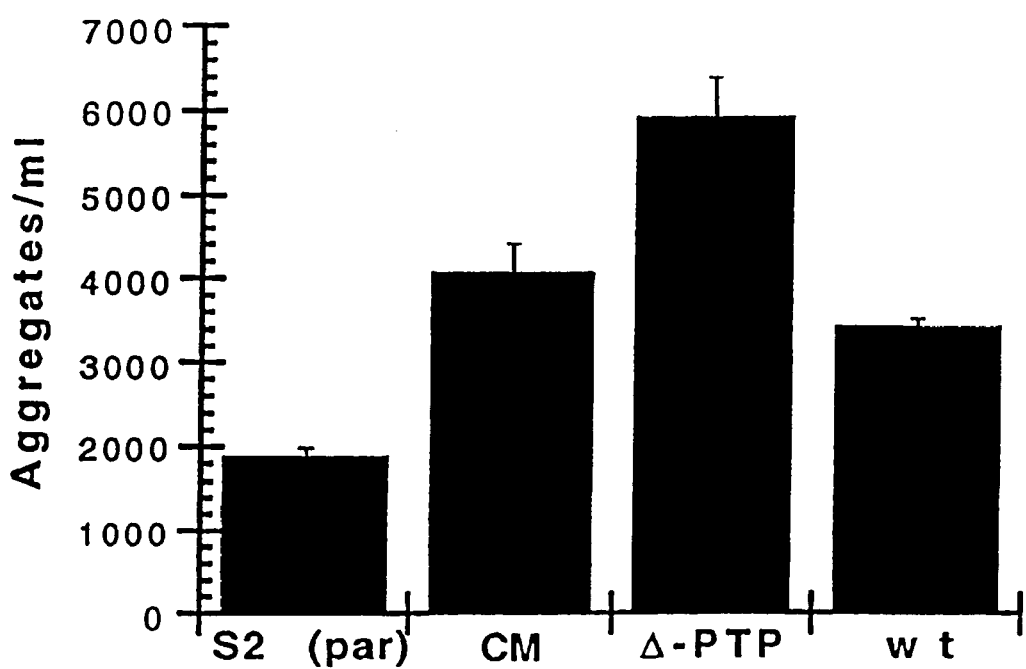

FIG. 22E. Effect of a mutation of the furin cleavage site on the aggregation capabilities of cells containing expression vectors encoding an R-PTPκ cDNA. The aggregates formed by parental S2 strains were compared with the aggregates of an S2 strain transfected with expression vectors encoding an R-PTPκ cDNA in which the furin cleavage site had been mutated (CM) (Y.-P. Jiang et al. Mol. Cell. Biol. 13, 2942 (1993)), the aggregates of cells transfected with a cDNA encoding a catalytically inactive deletion mutant of R-PTPκ lacking most of the intracellular (PTPase) domain (Δ-PTP), and the aggregates of cells transfected with a wt R-PTPκ cDNA (wt). The differences in aggregation intensity between the different forms of R-PTPκ may reflect protein expression levels. Mutation of the furin cleavage site left the vector adhesion behavior intact, suggesting that cleavage of the R-PTPκ proprotein is not required for induction of cellular aggregation. (Y.-P. Jiang et al. Mol. Cell. Biol. 13, 2942 (1993)). These numbers were provided by a Coulter-counter counting method, which counts the aggregates observed in a visual inspection. This method underestimates the aggregation levels because it only scores aggregates above a certain size threshold.

Figures 23A, 23B, 23C:
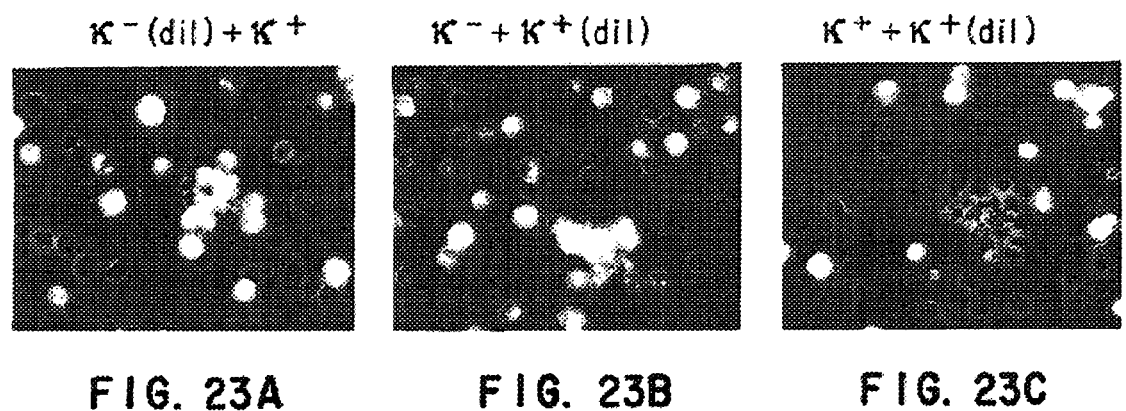
Figure 24A:
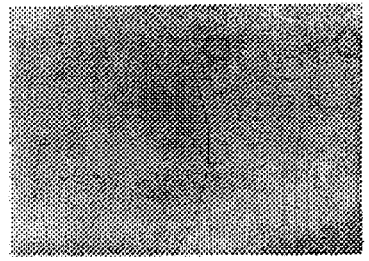
Figure 24B:
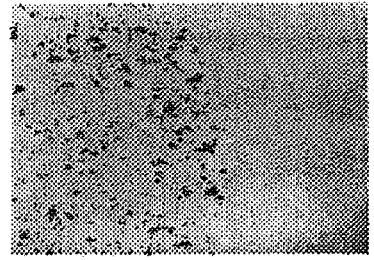
Figure 24C:
Figure 24D:
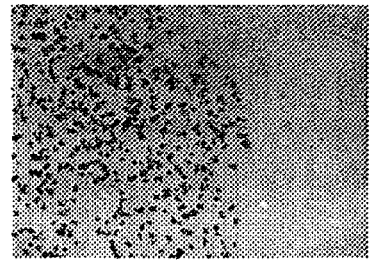

FIGS. 23A–23C. Aggregates consist solely of cells expressing the R-PTPκ protein. Two different cell populations, one of which had been labeled with the fluorescent dye diI (J. Schiessinger et al. Science 195, 307, (1977)), were allowed to co-aggregate and the resulting aggregates inspected by visible and fluorescence microscopy. diI-fluorescence is white in the photographs.

FIG. 23A: a pool of R-PTPκ expressing cells was allowed to aggregate in the presence of an equal number of diI-stained R-PTPκ-negative cells.

FIG. 23B: R-PTPκ expressing cells were stained with diI and allowed to aggregate in the presence of unstained RPTPκ-negative cells.

FIG. 23C: mixture of stained and unstained R-PTPκ-positive cells. In each case, ten aggregates were randomly localized under visible light only. Subsequent inspection under U.V. light consistently showed the staining pattern exemplified in the photographs. diI dye (Molecular Probes, Inc.) was added to the growth medium at a concentration of 3.2 μM during heat shock, and washed away prior to recovery and assay. $2 \times 10^6$ cells of each population were mixed and allowed to co-aggregate in a total volume of 1 ml.

FIGS. 24A–24D. Adhesion of R-PTPκ transfected cells to a surface coated with recombinant purified R-PTPκ extracellular domain protein. R-PTPκ-negative, 1, or positive, 2, S2 cells, or R-PTPκ-negative, 3, and positive, 4, L6 cells were incubated with a surface partially coated with the K2AP protein (circle), and the adherent cells fixed and stained. Amino acids 1–639 of the RPTPκ proprotein were fused in-frame with human placental alkaline phosphatase in the vector pBacblue III (Invitrogen) by a series of appropriate cloning steps. Recombinant virus was generated and used to infect High-Five cells for production of the K2AP fusion protein using standard procedures. A secreted alkaline phosphatase (AP) control protein was generated in L6 myoblast cells by stable transfection with a modified version of the AP-TAG vector encoding a fusion protein of AP with a signal peptide. Both proteins were affinity purified by elution from an anti-alkaline phosphatase monoclonal antibody (Medix Biotech) column using 100 mM diethanolamine pH 11.5, or 50% ethylene glycol, dialyzed against PBS, and stored at 4° C. The K2AP and AP proteins were approximately 90% and 50% pure, resp. as determined by silver staining. To generate a mammalian cell line expressing the RPTPκ protein, an MJ 30-based RPTPκ expression vector was co-transfected with psVneo into L6 cells, and individual clones surviving G418 selection screened for expression using immunoblotting. This procedure did not detect endogenous RPTPκ protein in the parental L6 cells.

The expressed protein underwent appropriate furin cleavage as described (Jiang, Y.-P. et al., 1993, *Mol. Cell. Biol.* 13:2942).

For adhesion assays, 4 µl aliquots of protein samples (20 g/ml) were spotted on 35 mm bacteriological Petri dishes and incubated at room temperature for 30 minutes. The solutions were removed by aspiration, and the surface of the entire plate blocked with 1% heat-inactivated BSA for 60–90 minutes. The plates were incubated with a suspension of S2 cells ($4 \times 10^6$/ml) in BSS with shaking (50 rpm) for one hour at room temperature, or with L6 cells in S-MEM ($2 \times 10^6$/ml) without shaking, at 37° C., washed three times with PBS, fixed and stained.

5. DETAILED DESCRIPTION OF THE INVENTION

Through the use of recombinant DNA methods, the present inventors have identified novel mammalian receptor-type (transmembrane) protein tyrosine phosphatases (PTPase; EC 3.1.3.48). In view of its receptor-like structure, and the likelihood that it is part of a family, the inventors have termed this protein, RPTPκ (receptor protein tyrosine phosphatase-κ). The family is designated herein as the "RPTPs." Human RPTPκ has 1444 amino acids (SEQ. ID NO:2).

Human RPTPκ (also designated MCP7) has an extracellular domain composed of one "MAM" domain, which is a sequence motif spanning about 170 amino acid residues, which was recently established by comparison of several functionally diverse receptors (including RPTPµ and the A5 protein) and is thought to play a role in cell adhesion (Beckmann & Bork, 1993, TIBS 18:40–41). The extracellular domain further includes one Ig-like, and four FN-type III-like segments. It therefore shares structural features with some cell adhesion molecules, permitting the classification of RPTPκ into the type II PTPase class.

The cDNA cloning of human RPTPκ and the complete DNA and amino acid sequences of human RPTPκ and its murine homologue are described herein. Northern analysis has been used to identify the natural expression of the protein in various cells and tissues. A partial cDNA clone of the catalytic domain of RPTPκ/HPTPκ has been previously described (commonly assigned U.S. patent application Ser. No. 07/654,188, from which the present application claims priority; Kaplan et al., *Proc. Natl. Acad. Sci.* 87:7000–7004 (1990); Krueger et al., *EMBO J.* 9:3241–3252 (1990)).

RPTPκ has been shown to be expressed in anatomically distinct regions of rat brain and its expression has been found to be developmentally regulated.

Remarkably, in addition to being composed of intracellular domains having enzymatic activity, the receptor family to which RPTPs belong includes transmembrane proteins having and N-terminal extracellular domains, analogous to the tyrosine kinase enzyme family (Tonks, N. K. et al. (1988) *Biochemistry* 27:8695–8701; Charbonneau, H. et al. (1988) *Proc. Natl. Acad. Sci. USA* 85:7182–7186; Streuli, M. et al. (1988) *J. Exp. Med.* 168:1523–2530; Streuli, M. et al. (1989) *Proc. Natl. Acad. Sci. USA* 86:8698–8702). The present inventors have therefore concluded that ligands in the extracellular environment can control the activity of this membrane-associated subclass of PTPases.

Further, results presented in the current invention demonstrate that Type II RPTPs undergo homophilic binding, i.e., Type II RPTP receptor molecules have the ability to bind to each other. Homophilic binding, as defined here, may include intercellular binding and/or binding of at least two Type II RPTP receptor proteins present on the surface of the same cell. In addition, homophilic binding may include not only binding of identical Type II RPTP molecules to each other, for example binding of at least two RPTPκ molecules to each other, but may also include the binding of any two Type II RPTP molecules to each other, such as, for example, the binding of RPTPκ to another Type II RPTP molecule. As demonstrated in the Working Example presented in Section 15, below, RPTPκ undergoes intercellular homophilic binding to other RPTPκ molecules. This result represents the first example of such a homophilic binding mechanism observed within the RPTP family of molecules, and provides a link between cell-cell contact and cellular signaling events involving tyrosine phosphorylation.

RPTPκ is useful in methods for screening drugs and other agents which are capable of activating or inhibiting the PTPase enzymatic activity, and thereby affecting major pathways of cellular metabolism. By attaching an intact RPTPκ, or the ligand-binding portion thereof, to a solid phase matrix, an affinity probe is created which can be used to screen biological products or chemical agents for their capacity to interact with the receptor on the basis of their binding activity. Bound material can then be eluted from the affinity probe in purified form.

RPTPκ is also useful in methods for screening drugs and other agents which are capable in inhibiting Type II RPTP homophilic binding, and thus affecting major processes involving, but not limited to, cell-cell and/or cell-ECK (extracellular matrix) interactions. By attaching an intact Type II RPTP such as RPTPκ, or an extracellular domain thereof, to a solid matrix, drugs or other agents may be screened for their ability to bind the RPTP. Those agents which bind the RPTP with specificity may be eluted off the solid phase matrix in purified form and further tested for their ability to inhibit RPTP homophilic binding. Note that it is intended to be within the scope of this invention that the inhibition of RPTP homophilic binding described herein refers to not only the binding of at least two identical Type II RPTP molecules, such as at least two RPTPκ molecules to each other, but also to binding of any Type II RPTP class of molecules to each other, such as, for example, the binding of RPTPκ to another Type II RPTP molecule. Potential agents which may inhibit such Type II RPTP binding may include, but are not limited to, soluble portions of Type II RPTP extracellular domains, antibodies directed against Type II RPTP extracellular domain epitopes, or small synthetic molecules. RPTP extracellular domains may include all or any inhibitory portion of the MAM, Ig, and/or fibronectin Type III (FN-III) domains, as well as peptides which include the HAV, and/or the RXR/LR consensus sequences, as described below. Any of the inhibitory compounds which inhibit homophilic RPTP binding may but are not required to modulate the phosphatase activity of the RPTP molecules whose binding capability is affected.

Further, the ability of a compound to inhibit Type II RPTPκ homophilic binding may be tested in a variety of ways. RPTPκ will be used as an example, but it should be kept clear that such techniques may be used for any Type II RPTP molecule. RPTPκ, or an extracellular domain thereof, may first be immobilized by attachment to a solid matrix, using techniques well known to those of ordinary skill in the art. Such a solid matrix may include but is not limited to a petri dish, microtiter well, or a glass, plastic or agarose bead. Second, RPTPκ, either in a purified protein form or, alternatively, present in a cell membrane preparation or present on the surface of an intact cell, may be incubated in the presence of the solid matrix together with a compound of interest. The ability of the compound to inhibit RPTRκ homophilic binding to the solid matrix may then be assayed by determining if RPTPκ molecules bind the immobilized molecules. Such a determination may be accomplished using a variety of techniques well known to those of ordinary skill in the art and include, but are not limited to the labelling of the RPTPκ present in purified form, in a cell membrane preparation, or in an intact cell. Alternatively, a compound of interest may be tested by incubating RPTPκ-expressing cells in the presence of the compound of interest and subsequently assaying the ability of the cells to undergo aggregation. Aggregation assays may include, but are not limited to directly counting aggregates using the aid of a microscope, and/or determining super-threshold particles with a coulter-counter.

Methods for coupling proteins and peptides to a solid phase matrix or carrier, the solid phase matrix materials useful in these methods, and means for elution, are well known to those of skill in the art.

The RPTPκ protein, or derivatives thereof having enzymatic activity, can be used for testing agents or compounds capable of enhancing or inhibiting the phosphatase activity. The ability of a compound under test to modify phosphatase activity can be tested in an in vitro system wherein the test compound is added to purified RPTPκ protein, or an enzymatically active derivative thereof, and the effects on enzyme activity measured using standard enzymological procedures well known to those of skill in the art.

Alternatively, the action of a compound on RPTPκ enzymatic activity can be measured in a whole cell preparation using live or fixed cells, or a membrane fraction derived from live or fixed cells. This method is useful for screening compounds acting via the extracellular receptor portion of the protein, as well as compounds acting directly on the enzymatic portion of the protein. A test compound is incubated with cells, or with a membrane preparation derived therefrom, which express high amounts of RPTPκ, such as transfected COS or NIH-3T3 cells. The amount of cellular phosphotyrosine is then measured, using methods well-known in the art (Honegger, A. M. et al., Cell 51:199–209 (1987); Margolis, B. et al., Cell 57:1101–1107 (1989)). The results are compared to results obtained in the absence of the test compound, or in the absence or presence of a known activator of RPTPκ enzymatic activity. In such studies, the action of the test compound in the presence of an activator of tyrosine kinase can also be measured. A compound which stimulates RPTPκ enzymatic activity will result in a net decrease in the amount of phosphotyrosine, whereas a compound which inhibits RPTPκ enzymatic activity will result in a net increase in the amount of phosphotyrosine. Compounds which inhibit homophilic Type II RPTP binding may also modulate the enzymatic activity of the RPTP molecules they affect, either by increasing or decreasing the RPTPs' phosphatase activity.

In the case of growth factor receptors which are tyrosine kinases, such as the receptors for epidermal growth factor (EGF) and for platelet-derived growth factor (PDGF), tyrosine phosphorylation is linked to cell growth and to oncogenic transformation. Activation of a PTPase, leading to dephosphorylation, would serve as a counterregulatory mechanism to prevent or inhibit growth, and might serve as an endogenous regulatory mechanism against cancer. Thus, mutation or dysregulation of this receptor/enzyme system may promote susceptibility to cancer.

Inhibitory compounds which are found that are capable of inhibiting Type II RPTP homophilic binding may be used to modulate a variety of cellular processes including, but not limited to those involving cell-cell and/or cell-ECM interactions. Such processes include, but are not limited to normal cellular functions such as differentiation and cell cycle control; normal cellular behaviors including, but not limited to motility, contact inhibition, cell adhesion, and signal transduction; and abnormal or potentially deleterious processes such as cellular transformation to a cancerous state.

Inhibitory compounds which inhibit Type II RPTP homophilic binding may be used to modulate such processes in mammals by administration of an effective concentration of the inhibitory compound to a mammal, using techniques well known to those of ordinary skill in the art. Inhibitory compounds may include, but are not limited to, compounds comprising soluble RPTP Type II extracellular domains, for example, soluble RPTPκ extracellular domains.

Depending on the conditions being treated, agents may be formulated and administered systemically or locally. Techniques for formulation and administration may be found in "Remington's Pharmaceutical Sciences," Mack Publishing Co., Easton, Pa., latest edition. Suitable routes may include oral, rectal, transmucosal, or intestinal administration; parenteral delivery, including intramuscular, subcutaneous, intramedullary injections, as well as intrathecal, direct intraventicular, intravenous, intraperitoneal, intranasal, or intraocular injections, just to name a few. For injection, the agents of the invention may be formulated in aqueous solutions, preferably in physiologically compatible buffers such as Hank's solution, Ringer's solution, or physiological saline bffer. For such transmucosal administration, penetrants appropriate to the barrier to be permeated are used in the formulation. Such penetrants are generally known in the art.

The insulin receptor is also a tyrosine kinase, and phosphorylation of tyrosine in cells bearing insulin receptors would be associated with normal physiological function. In contrast to the case of cell growth and cancer, activation of an RPTP would counteract insulin effects. Subnormal RPTP levels or enzymatic activity would act to remove a normal counterregulatory mechanisms. Perhaps more important, though, over-activity, or inappropriate activation, of an RPTP, such as RPTPκ, would be expected to partially or totally inhibit the action of insulin on cells, leading to diabetes (of an insulin-resistant variety). Thus, susceptibility to diabetes may be associated with RPTPκ dysregulation.

Therefore, the methods of the present invention for identifying normal or mutant genes encoding RPTPκ, or for measuring the amount or activity of RPTPκ associated with a cell or tissue, can serve as methods for identifying susceptibility to cancer, diabetes, or other diseases associated with alterations in cellular phosphotyrosine metabolism.

The present invention provides methods for evaluating the presence of, and the level of, normal or mutant RPTPκ in a cell or in a subject. Absence, or more typically, low expression of the RPTPκ, or presence of a mutant RPTPκ, in an individual may serve as an important predictor of susceptibility to oncogenic transformation and the development of cancer. Alternatively, over-expression of RPTPκ, possibly due to a mutant receptor/enzyme system insensitive to negative regulation, or due to overabundance of a stimulatory ligand in the body, may serve as an important predictor of susceptibility to diabetes.

An oligonucleotide probe corresponding to a DNA sequences encoding a part of RPTPκ (see below) is used to test cells from a subject for the presence of DNA or RNA sequences encoding the RPTPκ A preferred probe would be one directed to the nucleic acid sequence encoding at least 4 amino acid residues, and preferably at least 5 amino acid residues, of the RPTPκ. Qualitative or quantitative assays can be performed using such probes. For example, Northern analysis (see Section 7, below) is used to measure expression of an RPTPκ mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Sambrook et al., *MOLECULAR CLONING: A LABORATORY MANUAL*, Second Edition, Cold Spring Harbor Press, Cold Spring Harbor, N.Y. (1989), which references are herein incorporated by reference).

An in vitro enzymatic method which is capable of increasing the concentration of such desired nucleic acid molecules is called the "polymerase chain reaction or "PCR" (Mullis, K. et al., *Cold Spring Harbor Symp. Quant. Biol.* 51:263–273 (1986); Erlich, H. et al., EP 50424, EP 84796, EP 258017, EP 237362; Mullis, K., EP 201184; Mullis, K. et al., U.S. Pat. No. 4,683,202; Erlich, H., U.S. Pat. No. 4,582,788; and Saiki, R. et al., U.S. Pat. No. 4,683,194).

The PCR provides a method for selectively increasing the concentration of a particular nucleic acid sequence even when that sequence has not been previously purified and is present only in a single copy in a particular sample. The method can be used to amplify either single- or double-stranded DNA. The method uses two oligonucleotide probes to serve as primers for the template-dependent, polymerase mediated replication of a desired nucleic acid molecule.

The precise nature of the two oligonucleotide probes of the PCR method is critical to the success of the method. Polymerase dependent amplification of a nucleic acid molecule proceeds by the addition of a 5' nucleotide triphosphate to the 3' hydroxyl end of a nucleic acid molecule. Thus, the action of a polymerase extends the 3' end of a nucleic acid molecule. These inherent properties are exploited in the selection of the oligonucleotide probes of the PCR. The oligonucleotide sequences of the probes are selected such that they contain sequences identical to, or complementary to, sequences which flank the particular nucleic acid sequence whose amplification is desired. More specifically, the oligonucleotide sequence of the "first" probe is selected such that it is capable of hybridizing to an oligonucleotide sequence located 3' to the desired sequence, whereas the oligonucleotide sequence of the "second" probe is selected such that it contains an oligonucleotide sequence identical to one present 5' to the desired region. Both probes possess 3' hydroxy groups, and therefore can serve as primers for nucleic acid synthesis.

PCR reaction conditions are cycled between (a) those conducive to hybridization and nucleic acid polymerization, and (b) those which result in the denaturation of duplex molecules. In the first step of the reaction, the nucleic acids of the sample are transiently heated, and then cooled, in order to denature any double-stranded molecules. The "first" and "second" probes are then added to the sample at a concentration which greatly exceeds that of the desired nucleic acid molecule. Upon incubation under conditions conducive to hybridization and polymerization, the "first" probe will hybridize to the sample nucleic acid molecule at a position 3' to the sequence to be amplified. If the nucleic acid molecule of the sample was initially double-stranded, the "second" probe will hybridize to the complementary strand of the nucleic acid molecule at a position 3' to the sequence which is the complement of the sequence whose amplification is desired. Upon addition of a polymerase, the 3' ends of the "first" and (if the nucleic acid molecule was double-stranded) "second" probes will be extended. The extension of the "first" probe will result in the synthesis of an oligonucleotide having the exact sequence of the desired nucleic acid. Extension of the "second" probe will result in the synthesis of an oligonucleotide having the exact sequence of the complement of the desired nucleic acid.

The PCR reaction is capable of exponential amplification of specific nucleic acid sequences because the extension product of the "first" probe, of necessity, contains a sequence which is complementary to a sequence of the "second" probe, and thus can serve as a template for the production of an extension product of the "second" probe. Similarly, the extension product of the "second" probe, of necessity, contains a sequence which is complementary to a sequence of the "first" probe, and thus can serve as a template for the production of an extension product of the "first" probe. Thus, by permitting cycles of polymerization, and denaturation, a geometric increase in the concentration of the desired nucleic acid molecule can be achieved. For reviews of the PCR, see: Mullis, K. B., *Cold spring Harbor Symp. Quant. Biol.* 51:263–273 (1986); Saiki, R. K. et al. *BioTechnology* 3:1008–1012 (1985); Mullis, K. B. et al. *Meth. Enzymol.* 155:335–350 (1987).

In one embodiment, the present invention is directed to a naturally occurring mammalian RPTPκ. In another embodiment, the present invention is directed to a recombinant mammalian RPTPκ. The preferred mammalian RPTPκ of the present invention is of human origin. The invention provides the naturally occurring molecule substantially free of other proteins with which it is natively associated. "Substantially free of other proteins or glycoproteins" indicates that the protein has been purified away from at least 90 percent (on a weight basis), and from even at least 99 percent if desired, of other proteins and glycoproteins with which it is natively associated, and is therefore substantially free of them. That can be achieved by subjecting the cells, tissue or fluid containing the RPTPκ to standard protein purification techniques such as an immunoabsorbent column bearing an antibody specific for the protein. Other forms of affinity purification utilize solid-phase substrates which bind the RPTP's enzymatic domain, or a ligand that will bind to the receptor domain. Alternatively, the purification can be achieved by a combination of standard methods, such as ammonium sulfate precipitation, molecular sieve chromatography, and ion exchange chromatography.

It will be understood that the RPTPκ of the present invention can be biochemically purified from a variety of cell or tissue sources. For preparation of naturally occurring RPTPκ, tissues such as mammalian brain, especially of human origin, are preferred.

Alternatively, because the gene for the RPTPκ can be isolated or synthesized, the polypeptide can be synthesized substantially free of other mammalian proteins or glycoproteins in a prokaryotic organism or in a non-mammalian eukaryotic organism, if desired. As intended by the present invention, a recombinant RPTPκ molecule produced in mammalian cells, such as transfected COS, NIH-3T3, or CHO cells, for example, is a protein with the naturally occurring amino acid sequence or is a functional derivative thereof. Where a naturally occurring protein or glycoprotein is produced by recombinant means, it is provided substantially free of the other proteins and glycoproteins with which it is natively associated.

Alternatively, methods are well known for the synthesis of polypeptides of desired sequence on solid phase supports and their subsequent separation from the support.

The present invention provides any of a number of "functional derivatives" of the RPTPκ. By "functional derivative" is meant a "fragment," "variant," "analog," or "chemical derivative" of the RPTPκ, which terms are defined below. A functional derivative retains at least a portion of the function of the RPTPκ, such as (a) binding to a specific antibody, (b) phosphatase enzymatic activity, or (c) binding of the extracellular "receptor" domain to a ligand, which permits its utility in accordance with the present invention.

A "fragment" of the RPTPκ refers to any subset of the molecule, that is, a shorter peptide.

A "variant" of the RPTPκ refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication EP 75444).

At the genetic level, these variants ordinarily are prepared by site-directed mutagenesis (as exemplified by Adelman et al., *DNA* 2:183 (1983)) of nucleotides in the DNA encoding the protein or peptide molecule, thereby producing DNA encoding the variant, and thereafter expressing the DNA in recombinant cell culture. The variants typically exhibit the same qualitative biological activity as the nonvariant protein or peptide.

An "analog" of the RPTPκ refers to a non-natural molecule substantially similar to either the entire molecule or a fragment thereof.

A "chemical derivative" of the RPTPκ contains additional chemical moieties not normally a part of the peptide. Covalent modifications of the RPTPκ protein or of a peptide derived therefrom, are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate, pH 5.5–7.0, because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine ε-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues may be deamidated to the corresponding glutamyl and aspartyl residues, under mildly acidic conditions. Either form of these residues falls within the scope of this invention.

Derivatization with bifunctional agents is useful for cross-linking the protein or peptide to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidyl-propionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the X-amino groups of lysine, arginine, and histidine side chains (T. E. Creighton, *PROTEINS: STRUCTURE AND MOLECULE PROPERTIES*, W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in REM-INGTON'S PHARMACEUTICAL SCIENCES, 16th ed., Mack Publishing Co., Easton, Pa. (1980).

This invention is also directed to an antibody specific for an epitope of RPTPκ, preferably, of human RPTPκ, and the use of such an antibody to detect the presence of, or measure the quantity or concentration of, the RPTPκ in a cell, a cell or tissue extract, or a biological fluid.

The term "antibody" is meant to include polyclonal antibodies, monoclonal antibodies (mAbs), chimeric antibodies, and anti-idiotypic (anti-Id) antibodies.

Polyclonal antibodies are heterogeneous populations of antibody molecules derived from the sera of animals immunized with an antigen, preferably the RPTPκ protein or glycoprotein, a peptide derived therefrom or an epitope thereof.

Monoclonal antibodies are a substantially homogeneous population of antibodies to specific antigens. MAbs may be obtained by methods known to those skilled in the art. See, for example Kohler and Milstein, Nature 256:495–497 (1975) and U.S. Pat. No. 4,376,110. Such antibodies may be of any immunoglobulin class including IgG, IgM, IgE, IgA, and any subclass thereof. The hybridoma producing the mAbs of this invention may be cultivated in vitro or in vivo. Production of high titers of mAbs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules different portions of which are derived from different animal species, such as those having variable region derived from a murine mAb and a human immunoglobulin constant region. Chimeric antibodies and methods for their production are well-known in the art (Cabilly et al, Proc. Natl. Acad. Sci. USA 81:3273–3277 (1984); Morrison et al., Proc. Natl. Acad. Sci. USA 81:6851 6855 (1984); Boulianne et al., Nature 312: 643–646 (1984); Neuberger et al., Nature 314:268–270 (1985); Taniguchi et al., European Patent Publication EP171496 (Feb. 19, 1985); Morrison et al., European Patent Publication EP 173494 (Mar. 5, 1986); Neuberger et al., PCT Publication WO 86/01533 (Mar. 13, 1986); Kudo et al., European Patent Publication EP 184187 (Jun. 11, 1986); Sahagan et al., J. Immunol. 137:1066–1074 (1986); Robinson et al., International Patent Publication #PCT/US86/02269 (May 7, 1987); Liu et al., Proc. Natl. Acad. Sci. USA 84:3439–3443 (1987); Sun et al., Proc. Natl. Acad. Sci. USA 84:214–218 (1987); Better et al., Science 240:1041–1043 (1988)). These references are hereby incorporated by reference.

An anti-idiotypic (anti-Id) antibody is an antibody which recognizes unique determinants generally associated with the antigen-binding site of an antibody. An anti-Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other hybrid clones expressing antibodies of identical specificity.

Accordingly, mAbs generated against RPTPκ may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an RPTPκ epitope. The anti-Id mAbs thus have their own idiotypic epitopes, or "idiotopes" structurally similar to the epitope being evaluated, such as an epitope of RPTPκ.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., J. Nucl. Med. 24:316–325 (1983)).

It will be appreciated that Fab and F(ab')$_2$ and other fragments of the antibodies useful in the present invention may be used for the detection and quantitation of RPTPκ according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that anti-body. Epitopes or "antigenic determinants" usually consist of chemically active surface groupings of molecules such as amino acids or sugar side chains and have specific three dimensional structural characteristics as well as specific charge characteristics. An "antigen" is a molecule or a portion of a molecule capable of being bound by an antibody which is additionally capable of inducing an animal to produce antibody capable of binding to an epitope of that antigen. An antigen may have one, or more than one epitope.

An antibody is said to be specific for an antigen because it reacts in a highly selective manner, with that antigen and not with the multitude of other antigens which are structurally distinct.

The antibodies or antibody fragments of the present invention may be used to quantitatively or qualitatively detect the presence of cells which express the RPTPκ protein. This can be accomplished by immunofluorescence techniques employing a fluorescently labeled antibody (see below) coupled with light microscopic, flow cytometric, or fluorimetric detection. For such methods, the antibody is preferably specific for an extracellular epitope of RPTPκ.

The antibodies (or fragments thereof) useful in the present invention may be employed histologically, as in immunofluorescence or immunoelectron microscopy, for in situ detection of RPTPκ. In situ detection may be accomplished by removing a histological specimen from a subject, and providing a labeled antibody or antibody fragment of the present invention to such a specimen, preferably by applying or overlaying the antibody over the specimen. Through the use of such a procedure, it is possible to determine not only the presence of RPTPκ but also its distribution in the examined tissue. Using the present invention, those of ordinary skill will readily perceive that any of a wide variety of histological methods (such as staining procedures) can be modified in order to achieve such in situ detection. Such assays for RPTPκ typically comprise incubating a biological sample, such as a biological fluid, a tissue extract, freshly harvested cells, or cells which have been incubated in tissue culture, in the presence of a detectably labeled antibody specific for RPTPκ, and detecting the antibody by any of a number of techniques well-known in the art.

The biological sample may be incubated with a solid phase support or carrier such as nitrocellulose, or other solid support which is capable of immobilizing cells, cell particles or soluble proteins. The support may then be washed with suitable buffers followed by treatment with the detectably labeled RPTPκ-specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports or carriers include glass, polystyrene, polypropylene, polyethylene, dextran, nylon, amylases, natural and modified celluloses, polyacrylamides, and magnetite. The preferred carrier is totally insoluble in the solution in which the assay of the present invention takes place; partially soluble carriers well-known in the art may also be used. The support material may have virtually any possible structural configuration so long as the support-coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-RPTPκ antibody may be determined according to well-known methods. Those skilled in the art will be able to determine operative and optimal assay conditions for each determination by employing routine experimentation.

One of the ways in which the RPTPκ-specific anti-body can be detectably labeled is by linking the antibody, or a second antibody which binds to the anti-RPTPκ antibody, to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect RPTPκ through the use of a radioimmunoassay (RIA) (see, for example, Work, T. S. et al., *LABORATORY TECHNIQUES AND BIOCHEMISTRY IN MOLECULAR BIOLOGY*, North Holland Publishing Company, New York, 1978, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing a labeled second antibody (which functions as a "reporter molecule"). After a second incubation period to permit the labeled antibody to complex with the antigen bound to the solid support through the unlabeled antibody, the solid support is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to a fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The presence of normally functioning RPTPκ in a subject can also be tested using direct enzymatic assays, for the tyrosine phosphatase activity. Such biochemical measurements can be performed in vitro, using purified enzymes, allowing precise measurements of enzyme activity, or with membrane preparations, or whole cells, where the net phosphotyrosine level is determined.

In additional embodiments of the present invention, a nucleic acid molecule, prefereably DNA, comprising a sequence encoding an RPTPκ protein and methods for expressing the DNA molecule are provided one of ordinary skill in the art will know how to identify and clone additional RPTP molecules, of human or other mammalian species, which have sequence homology to the RPTPκ molecules described herein, using the genetic sequences and oligonucleotides of the present invention without undue experimentation. Furthermore, manipulation of the genetic constructs of the present invention allow the grafting of a particular ligand-binding receptor domain onto the transmembrane and catalytic portions of the RPTPκ resulting in chimeric molecules. Non-limiting examples of such chimeric molecules include RPTPκ wherein the receptor portion is an epidermal growth factor receptor, a fibroblast growth factor receptor, and the like. Genetically engineered chimeric receptors are known in the art (see, for example, Riedel, H. et al., *Nature* 324:628–670 (1986)).

Genetic constructs encoding RPTPκ, functional derivative thereof, and chimeric molecules such as those described above, can be used in gene therapy. An abnormal or dysfunctional RPTPκ, which results in disease, may be replaced by infusion or implantation of cells of the desired lineage (such as hemopoietic cells, neurons, etc.) transfected with DNA encoding normal RPTPκ. Alternatively, or additionally, cells carrying a chimeric RPTPκ having a receptor portion which binds a ligand of choice (e.g., EGF) can be used for such gene therapy.

The recombinant DNA molecules of the present invention can be produced through any of a variety of means, such as, for example, DNA or RNA synthesis, or more preferably, by application of recombinant DNA techniques. Techniques for synthesizing such molecules are disclosed by, for example, Wu, R., et al. (*Prog. Nucl. Acid. Res. Molec. Biol.* 21:101–141 (1978)), and procedures for constructing recombinant molecules can be found in Sambrook et al. (supra).

Oligonucleotides representing a portion of an RPTPκ are useful for screening for the presence of genes encoding such proteins and for the cloning of an RPTPκ gene. Techniques for synthesizing such oligonucleotides are disclosed by, for example, Wu, R., et al., supra.

Protein molecules are fragmented as with cyanogen bromide, or with proteases such as papain, chymotrypsin, trypsin, etc. (Oike, Y., et al., *J. Biol. Chem.* 257:9751–9758 (1982); Liu, C., et al., *Int. J. Pept. Protein Res.* 21:209–215 (1983)). Because the genetic code is degenerate, more than one codon may be used to encode a particular amino acid (Watson, J. D., In: *MOLECULAR BIOLOGY OF THE GENE*, 4th Ed., Benjamin/Cummings Publishing Co., Inc., Menlo Park, Calif. (1987)). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Mol. Biol.* 183:1–12 (1985). Using such "codon usage rules", a single oligonucleotide, or a set of oligonucleotides, that contains a theoretical "most probable" nucleotide sequence capable of encoding RPTPκ is identified.

Although occasionally an amino acid sequence may be encoded by only a single oligonucleotide, frequently the amino acid sequence may be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes RPTPκ.

The oligonucleotide, or set of oligonucleotides, containing the theoretical "most probable" sequence capable of encoding the RPTPκ fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the RPTPκ gene (Sambrook et al., supra).

A suitable oligonucleotide, or set of oligonucleotides, capable of encoding a fragment of the RPTPκ gene (or complementary to such an oligonucleotide) is identified as above and synthesized, using procedures well known in the art (Belagaje, R., et al., *J. Biol. Chem.* 254:5765–5780 (1979); Maniatis, T., et al., In: *MOLECULAR MECHANISMS IN THE CONTROL OF GENE EXPRESSION*, Nierlich, D. P., et al., Eds., Acad. Press, NY (1976); Wu, R., et al., *Prog. Nucl. Acid Res. Molec. Biol.* 21:101–141 (1978); Khorana, R. G., *Science* 203:614–625 (1979)). DNA synthesis may be achieved using an automated synthesizers. The oligonucleotide probe or set is hybridized by means well known in the art, against a DNA or, more preferably, a cDNA preparation derived from cells which are capable of expressing the RPTPκ gene. Techniques of nucleic acid hybridization are disclosed by Sambrook et al. (supra), and by Haymes, B. D., et al. (In: *NUCLEIC ACID HYBRIDIZATION, A PRACTICAL APPROACH*, IRL Press, Washington, D.C. (1985)), which references are herein incorporated by reference. Techniques such as, or similar to, those described above have successfully enabled the cloning of genes for human aldehyde dehydrogenases (Hsu, L. C. et al., *Proc. Natl. Acad. Sci. USA* 82:3771–3775 (1985)), fibronectin (Suzuki, S., et al., *EMBO J.* 4:2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221

(1983)) and human term placental alkaline phosphatase complementary DNA (Kam, W., et al., *Proc. Natl. Acad. Sci. USA* 82:(715–8719 (1985)).

In a alternative way of cloning the RPTPκ gene, a library of expression vectors is prepared by cloning DNA or, more preferably, cDNA (from a cell capable of expressing RPTPκ) into an expression vector. The library is then screened for members capable of expressing a protein which binds to an anti-RPTPκ antibody, and which has a nucleotide sequence that is capable of encoding a polypeptide that has the same amino acid sequence as all or part of RPTPκ. In this embodiment, DNA, or more preferably cDNA, is extracted and purified from a cell which is capable of expressing RPTPκ protein. The purified cDNA is fragmented (by shearing, endonuclease digestion, etc.) to produce a pool of DNA or cDNA fragments. DNA or cDNA fragments from this pool are then cloned into an expression vector in order to produce a genomic or cDNA library of expression vectors whose members each contain a unique cloned DNA or cDNA fragment.

An "expression vector" is a vector which (due to the presence of appropriate transcriptional and/or translational control sequences) is capable of expressing a DNA molecule which has been cloned into the vector and of thereby producing a peptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. If a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing RPTPκ in order to produce a prokaryotic genomic expression vector library. Procedures for preparing cDNA and for producing a genomic library are disclosed by Sambrook et al. (supra).

A DNA sequence encoding RPTPκ of the present invention, or encoding functional derivatives thereof, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al., supra, and are well known in the art.

A nucleic acid molecule, such as DNA, is "capable of expressing" a polypeptide if it contains nucleotide sequences which contain transcriptional and translational regulatory information and such sequences are "operably linked" to a polypeptide coding sequence. An operable linkage is a linkage in which the regulatory DNA sequences and the coding sequence are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the coding sequence may be obtained by the above-described methods. This region may be retained for its transcriptional termination regulatory sequences, such as termination and polyadenylation. Thus, by retaining the 3'-region naturally contiguous to the DNA coding sequence, the transcriptional termination signals may be provided. Where the transcriptional termination signals are not satisfactorily functional in the host cell used to express the protein, then a 3' region functional in that host cell may be substituted.

Two DNA sequences (such as a promoter region sequence and a RPTPκ coding sequence) are said to be operably linked if the nature of the linkage between the two DNA sequences does not (1) result in the introduction of a frame-shift mutation, (2) interfere with the ability of the promoter to regulate the transcription of the RPTPκ coding sequence. A promoter region is operably linked to a DNA coding sequence if the promoter is capable of effecting transcription of the coding sequence. Thus, to express the protein, transcriptional and translational signals recognized by an appropriate host are necessary. In order to be "operably linked" it is not necessary that two sequences be immediately adjacent to one another.

A promoter is a double-stranded DNA (or RNA) molecule which is capable of binding to RNA polymerase and promoting the transcription of an "operably linked" nucleic acid coding sequence. As used herein, a "promoter sequence" is the sequence of the promoter which is found on that strand of the DNA (or RNA) which is transcribed by the RNA polymerase. A "promoter sequence complement" has a sequence which is the complement of the "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to transcribe from only one strand of a duplex DNA template. Strand selection is determined by the orientation of the promoter sequence, and determines the direction of transcription since RNA is only polymerized enzymatically by the addition of a nucleotide 5' phosphate to a 3' hydroxyl terminus.

The promoter sequences of the present invention may be either prokaryotic, eukaryotic or viral. Suitable promoters are repressible, or, more preferably, constitutive. Examples of suitable prokaryotic promoters include promoters capable of recognizing the T4 (Malik, S. et al., *J. Biol. Chem.* 263:1174–1181 (1984); Rosenberg, A. H. et al., *Gene* 59:191–200 (1987); Shinedling, S. et al., *J. Molec. Biol.* 195:471–480 (1987); Hu, M. et al., *Gene* 42:21–30 (1986)), T3, Sp6, and T7 (Chamberlin, M. et al., *Nature* 228:227–231 (1970); Bailey, J. N. et al., *Proc. Natl. Acad. Sci. USA* 80:2814–2818 (1983); Davanloo, P. et al., *Proc. Natl. Acad. Sci. USA* 81:2035–2039 (1984)) polymerases; the $P_R$ and $P_L$ promoters of bacteriophage λ (*THE BACTERIOPHAGE LAMBDA*, Hershey, A. D., Ed., Cold Spring Harbor Press, Cold Spring Harbor, N.Y. (1973); Lambda II, Hendrix, R. W., Ed., Cold Spring Harbor Press, Cold Spring Harbor, N.Y. (1980)); the trp, recA, heat shock, and lacZ promoters of *E. coli*; the α-amylase (Ulmanen, I., et al., *J. Bacteriol.* 162:176–182 (1985)) and the σ-28-specific promoters of *B. subtilis* (Gilman, M. Z., et al., *Gene* 32:11–20 (1984)); the promoters of the bacteriophages of *Bacillus* (Gryczan, T. J., In: *THE MOLECULAR BIOLOGY OF THE BACILLI*, Academic Press, Inc., NY (1982)); *Streptomyces promoters* (Ward, J. M., et al., *Mol. Gen. Genet.* 203:468–478 (1986)); the int promoter of bacteriophage λ; the bla promoter of the β-lactamase gene of pBR322, and the CAT promoter of the chloramphenicol acetyl transferase gene of pPR325, etc. Prokaryotic promoters are reviewed by Glick, B. R., *J. Ind. Microbiol.* 1:277–282 (1987)); Cenatiempo, Y. (*Biochimie* 68:505–516 (1986)); Watson, J. D. et al. (supra); and Gottesman, S. *Ann. Rev. Genet.* 18:415–442 (1984)).

Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* 290:304–310 (1981)); and the yeast gal4 gene promoter (Johnston, S. A., et al., *Proc. Natl. Acad. Sci. USA* 79:6971–6975 (1982); Silver, P. A., et al., *Proc. Natl. Acad. Sci. USA* 81:5951–5955 (1984)). All of the above listed references are incorporated by reference herein.

Strong promoters are preferred. Examples of such preferred promoters are those which recognize the T3, SP6 and T7 polymerases, the PL promoter of bacteriophage λ, the recA promoter and the promoter of the mouse metallothionein I gene. A most preferred promoter for eukaryotic expression of RPTPκ is an SV40 promoter such as that driving transcription in the pLSV vector (Livneh, E., et al., (1986) *J. Biol. Chem.* 261:12490–12497). The sequences of such polymerase recognition sites are disclosed by Watson, J. D. et al. (supra).

Having now generally described the invention, the same will be more readily understood through reference to the following example which is provided by way of illustration, and is not intended to be limiting of the present invention, unless specified.

6. EXAMPLE: ISOLATION AND ANALYSIS OF MURINE RPTPκ cDNA CLONES

In an effort to identify new PTPases, a mouse brain cDNA library in λgt11 was screened under relaxed stringency conditions using as a probe an oligonucleotide corresponding to the intracellular two tandem PTPase homology domains of human CD45 (Sap et al., supra). Following initial characterization and classification of the isolated clones, several subsequent rounds of screening mouse brain libraries at high stringency yielded a set of cDNA fragments that together encompassed the entire coding sequence for RPTPκ. The relationship between the different RPTPκ cDNA clones isolated was confirmed by Northern and reverse transcriptase/PCR analyses (see Materials and Methods section and FIG. 2 for details).

6.1. Library Screening

The original RPTPκ cDNA clone was isolated by low-stringency screening of a λgt11 mouse brain cDNA library with a probe consisting of the intracellular domain of human CD45, which contains two tandem PTPase domains (see: Sap, J. et al., 1990 Proc. Natl. Acad. Sci. USA 87:6112–6116, for details). After initial characterization, one of the isolated clones (λ-50, containing a 935 nucleotide fragment with characteristic homology to members of the PTPase family), was used to rescreen the same library, yielding clones λ-602 and λ-604. Sequence analysis showed that clone λ-602 was identical to λ-604 at both extremities, but was interrupted by a sequence containing stop codons in all three reading frames. Its analysis was therefore discontinued, since it is likely to represent an incompletely spliced RNA species. By contrast, λ-604 appeared to contain one PTPase homology domain and an additional 2042 nt. of upstream coding sequence, including a likely membrane-spanning region.

In order to obtain a full length RPTPλ cDNA, the entire insert of clone 604 was used to screen another (randomly primed) mouse brain cDNA library (Clontech), leading to the isolation of two hybridizing clones, λ-35 and λ-37. Clone 35 appeared to overlap with the N-terminus of clone 604 and to encompass the translational initiation codon for the RPTPκ precursor protein (see results section). Initial sequence analysis of clone 37 however revealed no overlap with the clone 604 probe, although it contained a clear additional PTPase homology followed by a stop codon in a position characteristic for the second PTPase domain of a RPTPase. Several controls were used to show that clone 37 corresponds to the bona fide C-terminus of RPTPκ. In Northern analysis, clones 37 and 604 recognize identical mRNA species in all mouse tissues examined.

A reverse transcriptase/PCR analysis on mouse liver poly(A)+ RNA using primers corresponding to clones 604 and 37, followed by cloning and sequencing, yielded a fragment of the expected size, exactly joining both clones at the same EcoRI site where each isolated cDNA clone ended.

In retrospect, clone 37 was therefore most likely picked up in the screening with the clone 604 fragment due to the existence of an additional small cDNA fragment in the original λ-37 phage isolate that went undetected due to its small size, or by fortuitous crosshybridization between the two PTPase homologies of RPTPκ. A schematic summary of the different cDNA clones discussed is included in FIG. 2.

6.2. Nucleotide Sequence Determination cDNA fragments were isolated from phage clones, subcloned into Bluescript cloning vectors and subjected to sequence analysis by the dideoxynucleotide chain termination method (Sequenase, United States Biochemical) using synthetic oligonucleotide primers. All sequences were determined on both strands. Sequences were assembled and analyzed using the GCG 7 software package (Devereux, J. et al., 1984 *Nuc. Acids Res.* 12:387–395). The assembled RPTPκ cDNA nucleotide sequence was submitted to Genbank under accession number L10106.

6.3. Sequence Alignments

All DNA and protein data base searches were done with the Genetic Computer Group sequence analysis software package (Devereux et al., *Nucleic Acid Res.* 12:387–396 (1989)). The SwissProt and Gene Bank\European Molecular Biology Laboratory data bases were searched with FASTA and TFASTA, respectively (Pearson and Lipman, *Proc. Natl. Acad. Sci.* 85:2444–2448 (1988)). Proteins were aligned with the Genetics Computer Group programs, LINEUP, PILEUP, PRETTY and BESTFIT.

6.4. Results and Discussion 6.4.1. Isolation and Sequence Analysis of cDNA Clones Encoding Murine RPTPκ

The nucleotide sequence of murine RPTPκ (SEQ ID NO:3) is shown in FIG. 1A–1H. The complete amino acid sequence of RPTPκ. (SEQ ID NO:1) is shown in FIG. 1A–1H and in FIG. 3.

The assembled RPTPκ cDNA sequence can be divided into a 5'untranslated region of 1072 base pairs, a single open reading frame of 4374 base pairs and a 3' untranslated region of 388 base pairs. The deduced amino acid sequence of the RPTPκ precursor protein is shown in FIG. 3. The translational initiation codon is identified by a standard environment for initiation of translation (Kozak, supra) and by the existence of an upstream in-frame stop codon (position −252), and is followed by a hydrophobic region that may serve as a signal peptide. A second hydrophobic region is found between amino acid residues 753 and 774 and is followed by a series of predominantly basic residues, characteristic of a stop transfer sequence. These features delineate a putative extracellular region of 752 amino acid residues (including the signal sequence), and an intracellular portion of 683 amino acids. The latter contains the tandem repeat of two PTPase homologies typical for most RPTPases isolated so far (Fischer, E. H. et al., 1991 Science 253: 401–406).

An intriguing feature of RPTPκ is the extended distance between its trans-membrane segment and the start of the first phosphatase homology domain. This region is about 70 residues longer than in all other previously described RPTPases, with the exception of mRPTPμ (Gebbink et al., supra).

Interestingly, a variant of RPTPκ was found by the present inventors' laboratory to contain a similarly-sized insertion in the same position. It is conceivable that such an insertion generated by alterative splicing might constitute a separate functional unit in RPTPases.

The first approximately 170 amino acids of RPTPκ show similarity (26% overall identity) to a region in the *Xenopus* cell surface protein A5 with features of Ig-like domains (FIG. 5). The A5 protein (SEQ ID NO: 7) thought to function in recognition between input and target neurons in the visual system (Takagi, S. et al., 1991 Neuron 7:295–307).

This first domain is followed by one Ig-like repeat (approximately residues 210 to 270) and four putative fibronectin type III-like (FN-III) repeats (residues 296 to 681). Database searching revealed clear similarity of these FN-III domains to similar domains in the tyrosine phosphatases R-PTPμ and LAR, the *Drosophila* R-PTPases DLAR and DPTP10D, and *Drosophila* neuroglian (Bieber, A. J. et al. 1989. Cell 59:447–460; Gebbink et al., supra; Streuli, M. et al., 1988, supra; Streuli, M. et al., 1989,supra; Tian et al., supra; Yang et al., supra).

Some other features of the extracellular domain of RPTPκ are noteworthy. First, it contains the sequence HAV (amino acids 340–342; within the first FN-III repeat) implicated in cel-cell contact in members of the cadherin family (Blaschuk, O. W. et al., 1990 J. Mol. Biol. 211:679–682). Second, the extracellular domain (640–643) contains the sequence RTKR, a consensus cleavage site for the processing endoprotease furin (Hosaka, M. et al., 1991 *J. Biol. Chem.* 266:12127–12130). Other potential posttranslational modification sites include 12 potential N-linked glycosylation sites, and SG-motifs which are candidates for chondroitin sulfate attachment (residues 172, 176, 277, 333, 662) (Kjellen, L. et al. 1991 Annu. Rev. Biochem. 60:443–470).

Overall, the sequence of RPTPκ shows a high degree of sequence similarity to mRPTPμ (77% overall similarity at the amino acid level) (Gebbink et al., supra). The sequence identity between this pair of related R-PTPases is highest in the first PTPase homology domain (80% as compared to 74% identity for the second PTPase domain). This is in contrast to the situation that has been observed for the relationship between the closely related pairs of R-PTPases LAR and HPTPδ, and RPTPβ/HPTPζ and RPTPγ (Kaplan, R. et al. 1990 *Proc. Natl. Acad. Sci. USA* 87:7000–7004; Krueger, N. X. et al., 1990 EMBO J. 9:3241–3252; Streuli, M. et al., 1988, supra). The latter pairs of related R-PTPases are more related in their second PTPase homology domains. The sequence of RPTPκ is also highly similar to that of PCR fragment PTP 191–33 described by Nishi, M. et al., 1990 FEBS Lett. 271:178–180.

7. EXAMPLE: EXPRESSION AND TISSUE DISTRIBUTION OF RPTPκ

7.1. Tissue Expression and Northern Analysis

Poly(A)+RNA was isolated from adult mouse tissues by oligo(dT) selection as described previously (Vennstrom, B. et al. 1982 Cell 28:135–143). Five μg of poly(A)+ RNA per lane were fractionated on formaldehyde-containing 1% agarose gels, transferred to Nytran membranes, and probed under high stringency conditions with different regions of the RPTPκ cDNA. RNA loading and quality was controlled for by ethidium bromide staining.

7.1.1. Expression of the RPTPκ Protein

In order to assemble a full-length RPTPκ cDNA from the various isolated fragments, a convenient fragment which included the N-terminus was generated from clone 35 by a PCR reaction using the N terminal primer 5'GAGCCGCG-GCTCGAGTTAACCGCCATGGATGTGGCGGCCG3' (SEQ ID NO: 9) and the C-terminal primer 5'GCTCA-CAGCTAGTTCAGCCC3' (SEQ ID NO: 10). This manipulation also removed all of the 5' untranslated sequences, while retaining an optimized Kozak consensus sequence for translation initiation (Kozak, M. 1983 *Micro biol. Rev.* 47:1–45).

The amplified 470 nucleotide product was digested with Sac II and PpuM 1, and cloned between the Sac II and PpuM I sites of clone 604, yielding plasmid $pK_0$ (the Sac II site being in the polylinker region of the Bluescript cloning vector). The 1.1 kb Eco RI fragment from clone 37 (containing the C-terminal end of the coding sequence) was then cloned into the unique and corresponding Eco RI site of $pK_0$ in the appropriate orientation, yielding construct $pK_1$ containing the fully assembled coding sequence without the 5' untranslated sequences. The modified cDNA was then released as one fragment using Hpa I (N-terminal) and Xho I (C-terminal), and cloned between the Sma I and Sal I sites of a CMV-enhancer/promoter-driven eukaryotic expression vector.

7.1.2. Generation of Antisera Specific for Epitopes of RPTPκ

Antigenicity of peptides included in the the RPTPκ protein was predicted using the Jameson-Wolf algorithm included in the GCG 7 Peptidestructure program (Devereux, J. et al., 1984 *Nucl. Acids Res.* 12:387–395). Two peptides were synthesized. The peptides were coupled to the protein keyhole limpet hemocyanin by glutaraldehyde crosslinking and injected into rabbits at two week intervals (100 pg per injection).

The first peptide corresponded to a site near the predicted N-terminus of the RPTPκ protein (SEQ ID NO:1), specifically, residues 60–76, having the sequence SAQE-PHYLPPEMPQGST. Immunization with this peptide yielded antiserum 116.

The second peptide corresponded to a region located at the N-terminus of the first PTPase homology in the intracellular region of the RPTPκ protein (SEQ ID NO:1), specifically, residues 910 to 929 having the sequence SASWD-VAKKDQNRAK. Immunization with this peptide yielded antiserum 122) (FIG. 14).

7.1.3. Transfection, Labeling and Immunoprecipitation

Subconfluent cultures of COS or HeLa cells in 10 cm diameter dishes (as indicated) were transfected by the DEAE-dextran or calcium phosphate technique, respectively. Between 48 and 72 hours after transfection, the cells were metabolically labeled for 2 hours in methionine-free medium containing 50 µCi/ml [$^{35}$S]-methionine (ICN). In the pulse-chase analysis shown in FIG. 10, cells were labeled with 200 µCi/ml of the isotope. After labeling, cells were washed in PBS and lysed in Triton-X-100 lysis buffer (50 mM Hepes pH 7.5, 150 µM NaCl, 1.5 MM MgCl$_2$, 1 mM EGTA, 10% glycerol, 1% Triton-X-100, 200 µg/ml PMSF, 10 µg/ml Aprotinin, 10 µg/ml Leupeptin) at 4° C.

Cell lysates were incubated at 4° C. for 2 hours with Protein A-Sepharose previously preincubated with the respective anti-RPTPκ antibody. Where indicated, 20 µg of the antigenic peptide was included in the immunoprecipitation reaction as a control for specificity. Immunoprecipitates were washed with high, medium and low salt buffers (Lev, S. et al., 1991 EMBO J. 10:647–654), with the exception of the experiment depicted in FIG. 12 where washing was with HNTG-buffer (20 mM Hepes pH 7.5, 150 mM NaCl, 10% glycerol, 0.1% Triton-X-100). Immunoblotting analyses were performed using standard procedures.

7.1.4. Protein Tyrosine Phosphatase Enzymatic Assay

Phosphatase enzymatic assays were performed with RPTPκ protein immunoprecipitated with antiserum 116 (specific for the extracelular domain) from transiently transfected COS cells. The protein A-Sepharose/RPTPκ immunoprecipitated complexes were washed 4 times with HNTG, and once with M7.6 buffer (60 mM Tris, pH 7.6, 5 mM EDTA, 10 mM DTT, 50 mM NaCl, 50 µg/ml BSA).

The enzymatic assay was performed essentially as described (Streuli, M. et al., 1989 *Proc. Natl. Acad. Sci. USA* 86:8698–8702). The immune complexes were resuspended in 50 µl M17.6 buffer (containing 1 mM vanadate where indicated) to which had been added 10 µl [$^{32}$P]tyrosine phosphorylated myelin basic protein (approximately 12 µM). The [$^{32}$P]-tyrosine-phosphorylated myelin basic protein had been produced by in vitro phosphorylation using EGF-receptor immunoprecipitated from A431 cells. The reactions were incubated for 15 minutes at 37° C. with shaking, stopped with 750 µl of an acidic stop mix containing activated charcoal, and the amount of released free [$^{32}$P]-phosphate was measured.

7.1.5. Endoglycosidase F Treatment

Cultures of cells transfected with RPTPκ cDNA were lysed in 1% SDS at 100° C. for 3 minutes. The total cell lysates were sonicated 3 times at full speed, then diluted with distilled water to decrease the concentration of SDS to 0.1%. The cell lysates were incubated at 37° C. for 18 hours in the presence of 0.2 units endoglycosidase F (Boehringer-Mannheim), 0.25 M sodium acetate, pH 5.2, 20 mM EDTA, 10 mM β-mercaptoethanol and 0.6% NP-40. The total enzyme-treated lysate was directly loaded onto SDS-PAGE gels, which were run, transferred to nitrocellulose and blotted with antiserum 116 or antiserum 122 as indicated.

7.1.6. Site-directed Mutagenesis

In vitro site-directed mutagenesis was performed using a commercially available kit from Clontech, using the manufacturer's instructions. An oligonucleotide having the sequence CTACACCCACATCTAACGAACCGTGAAG-CAGGG (SEQ ID NO: 11) was used to modify the amino acid sequence RTKR (SEQ ID NO: 12) in the cleavage site to the sequence LTNR (SEQ ID NO: 13). Mutagenesis was confirmed by direct DNA sequencing.

7.1.7. In Situ Hybridization of RPTPκ cDNA to Rat Tissues

Sprague-Dawley rats were sacrificed by decapitation, and their brains were removed and sectioned into 20 µm sections in a cryostat. Sections were postfixed in 4% paraformaldehyde in 0.1 M sodium phosphate, pH 7.4, for 20 min.

A 50 base oligonucleotide complementary to residues 1493–1543 of the isolated RPTPκ cDNA sequence (SEQ ID NO:3) was used as a probe. The oligonucleotide was labeled with [(α-$^{35}$S]dATP (NEN, DuPont) using terminal deoxynucleotidyl transferase (Boehringer Mannheim) and purified using Sephadex G25 quick spin columns (Boehringer Mannheim). The specific activity of the labeled probe was from $2 \times 10^8$ to $5 \times 10^8$ cpm/µg DNA. Prehybridization and hybridization were carried out in a buffer containing 50% deionized formamide, 4×SCC, 1× Denhardt's solution, 500 µg/ml denatured salmon sperm DNA, 250 µg/ml yeast tRNA and 10% dextran sulfate.

The tissue sections were incubated in a humidified environment for 14–18 h at 42–46° C. in hybridization solution containing the labeled probe and 10 mM dithiothreitol. Specificity controls were performed on adjacent sections by adding to the labeled oligonucleotide a 100-fold excess of the unlabeled oligonucleotide. After incubation, sections were washed in 2 changes of 2×SSC at room temperature for 1 h, then in 1×SCC at 50° C. for 30 min, 0.5×SCC at 50° C. for 30 min, and in 0.5×SCC at room temperature for 10 min. Sections were dehydrated and exposed to X-Omat film for 3 weeks.

7.2. Results and Discussion

7.2.1. Expression of RPTPκ in Adult Tissues

Northern blot analysis on adult mouse tissues (FIG. 6) revealed that RPTPκ expression is broad. Two major transcripts of 5.3 and 7.0 kb were detectable at different levels in all examined tissues except in spleen and testis. Particularly high levels of the 5.3 kb transcript were seen in liver and kidney tissue. An identical pattern was detected using as a probe both an N-terminal and central part of the cDNA. Although the 5.3 kb size is similar to the 5.7 kb described for mRPTP (Gebbink et al., supra), RPTPκ appears to be much more widely expressed than mRPTPµ. Expression of the latter is virtually restricted to lung and, at lower levels, brain and heart.

7.2.2. Transient Expression and Enzymatic Activity of RPTPκ

As described above, the RPTPκ coding sequence was cloned into an expression vector under the control of the CMV enhancer and promoter after manipulation to remove the untranslated leader sequence. The construct was transiently transfected into HeLa cells which were metabolically labeled with [$^{35}$S]-methionine, lysed and subjected to a radioimmunoprecipitation assay. The antibody probe was an antiserum raised against a peptide located in the N-terminus of the protein (residues 60 to 76). This antiserum precipitated a protein of about 210 kDa from RPTPκ transfected cells, but not from mock transfected cells (transfected with an "empty" expression vector) (FIG. 7). This immunoprecipitation was blocked by inclusion of the antigenic peptide in the immunoprecipitation reaction (lanes 3 and 6), but not by inclusion of a heterologous peptide corresponding to the first catalytic homology domain of RPTPκ.

To confirm that the protein encoded by the RPTPκ cDNA had PTPase enzymatic activity, immune complexes from transfected cells were incubated in an appropriate buffer with [$^{32}$P]-tyrosine phosphorylated myelin basic protein as a substrate. As shown in FIG. 8, approximately 3-fold higher PTPase activity was detectable in immune complexes from RPTPκ transfected cells as compared to control cells. This PTPase activity could be significantly inhibited by vanadate.

7.2.3. In Situ Hybridization Analysis of RPTPκ Expression in the Developing and Adult Cenral Nervous System The level of expression of RPTPκ mRNA was generally higher in the developing than in the adult central nervous system (CNS). At embryonic day 18 (E18) and at E20, the RPTP(κ) mRNA levels were highest in the cerebral cortex and hippocampal formation, followed by the cerebellum, brain stem and spinal cord. In the rest of the embryo, the highest levels were found in the liver, kidney and intestine (left panel, FIG. 13A). At postnatal day 6 (P6) and P8, expression was maximal in the cortex, olfactory bulb and hippocampal formation, especially in the dentate gyrus and CA3. In the cerebellum, the expression was highest in the granular cell layer, which in this stage of development still occupies the outermost cell layer of the cerebellum (right panel, FIG. 13B).

In the adult rat, expression was lower, but was clearly visible in the olfactory bulb and throughout the cortex, including the pyriform and cingulate cortex. Expression of the RPTPκ mRNA was also observed in the hippocampal formation. Interestingly, expression in the cerebellum was barely detectable in the adult. This was in marked contrast with the distinct patten and high level of expression observed at P6 and P8, a period of active cerebellar development.

The in situ hybridization studies confirmed the expression of the RPTPκ in several organs. In addition, they demonstrated that, in the CNS, RPTPκ is expressed in specific areas in a developmentally regulated manner. The levels of RPTPκ expression are higher in the actively developing areas, but expression persists in the adult, mainly in certain areas of the cortex and in the hippocampal formation. These findings are consistent with the idea that CNS RPTPases are actively involved in development and plasticity. Studies on the expression of RPTPs in *Drosophila* have led to similar suggestions (Tian et al., supra; Yang et al., supra).

8. EXAMPLE: CHROMOSOMAL LOCALIZATION OF THE MURINE RPTPκ GENE

The method was essentially as described previously (Sap, J. et al., 1990 *Proc. Natl. Acad. Sci. USA* 87:6112–6116; Silver, J., 1985 *J. Hered.* 76:436–440; Taylor, B., 1978, In: H. C. Morse, III (ed.), *ORIGINS OF INBRED MICE*, Academic Press, New York, pp. 423–438; Taylor, B. A., 1989 In: M. F. Lyon et al., eds, *GENETIC VARIANTS AND STRAINS OF THE LABORATORY MOUSE*. Oxford University Press, New York, pp. 773–796). Southern blotting analysis of Taq I-digested mouse genomic DNA with the 604 RPTPκ probe revealed an array of 12 fragments that appeared invariant between the inbred strains surveyed, as well as a smaller set of variable bands that were used to define two allelic forms of the gene:

(1) a was defined by the presence of 1.9, 3.5 and 3.8 kb fragments and was present in inbred mouse strains AKR/J, C3H/HeJ, DBA/J, SM/J; and (2) b was defined by the presence of a 4.1 kb fragment and was present in inbred mouse strains C57BL/6J, 020/A, C57L/J, SWR/J, SJL/J, BALB/cJ, STS/A, NZB/BlNJ).

Analysis of the inheritance pattern of this variant among recombinant inbred strains of mice (Table I), and comparison of strain distribution patterns thus obtained with those generated previously for other genetic markers, revealed close linkage between RPTPκ and two markers of proximal chromosome 10: D1OMit3 (2 discordancies among 22 strains typed, indicating a distance of 2.6 cM between the loci (0.3 cM to 13.0 cM defined 95% confidence limits); and Ly-41 (O discordancies among 30 strains typed, indicating a distance between the loci of <3.5 cM at 95% confidence). The gene symbol Ptpk is proposed by the inventors, consistent with the symbol Ptpa previously assigned to RPTPα (Sap et al., supra).

This region of mouse chromosome 10 contains multiple genes with human homologues mapping to chromosome 6q. Based on synteny, this would predict a localization of the human RPTPκ homologue to 6q, in contrast to 18pter-q11 for human RPTPμ (Gebbink et al., supra).

TABLE I

DNA FRAGMENT LENGTH VARIANT ASSOCIATED WITH THE MOUSE RPTPκ GENE.

A. Alleles and strain distribution patterns

| Allele | (Size kb)) | Strains |
|---|---|---|
| a | 1.9 + 3.5 + 3.8 | AKR/J, C3H/HeJ, DBA/2J, SM/J AKXL-5, 6, 7, 8, 17, 21, 25, 28, 29, 37, 38 BXD-1, 2, 5, 14, 15, 18, 21, 23, 25, 28, 32 BXH-2, 4, 7, 8, 12, 14, 19 NXSM-D, L, W, X OXA-4, 5, 7, 8, 13 |
| b | 4.1 | C57BL/6J, 020/A, C57L/J, SWR/J, SJL/J, BALB/CJ, STS/A, NZB/BlNJ AKXL-9, 12, 13, 14, 16, 19, 24 BXD-6, 8, 9, 11, 12, 13, 16, 19, 20, 22, 24, 27, 29, 30, 31 BXH-3, 6, 9, 10, 11 NXSM-C, E, F, I, N, P, Q, T1, T2, U, Z OXA-1, 2, 3, 6, 9, 10, 11, 12, 14 |

B. Linkage of ptpk to other markers typed in Recombinant Inbred strains

| Marker | Chr | R/N | Odds | Distance (cM) |
|---|---|---|---|---|
| D1OMit3 | 10 | 2/22 | 0.00941 | 2.6 (0.3–13.0) |
| Ly-41 | 10 | 0/30 | <0.00001 | 0.0 (<3.5) |

A) 10 μg quantities of liver or spleen genomic DNA were digested with Taq1 enzyme and analyzed by Southern blotting with the 604 RPTPκ probe as described previously to define two alleles of the ptpk gene and to follow their inheritance in panels of recombinant inbred (RI) strains of mice.
B) The resulting strain distributions were compared with those previously determined for other loci in these panels of mice. Two matches were found that were unlikely to be due to chance at a 5% confidence level. For each of these, the number of non-matching RI strains found (R) is shown as a fraction of the total number of RI strains typed (N) for the two markers, together with the odds of observing that number of non-matches or a smaller one by chance (Blank, R.D. et al., 1988 Genetics 120:1073–1083), the estimated distance between the marker and ptpk, and the 95% confidence limits for that estimate (Silver, supra; Taylor, 1978, supra).

9. EXAMPLE: POSTTRANSLATIONAL PROTEOLYTIC PROCESSING OF RPTPκ

During experiments designed to achieve stable expression of RPTPκ in 3T3 cells, the present inventors observed the generation of a product of an unexpected, smaller size as well as the generation of aberrantly-sized products upon transient transfection of COS cells.

The present inventors noted the presence of a proteolytic cleavage signal in the extracellular domain of RPTPκ, (RTKR, residues 640 to 643 of SEQ ID NO: 1), in the fourth FN-III repeat; FIG. 3) and wished to examine its significance in light of these observations. Thus, additional experiments were performed in COS cells transfected by the DEAE-dextran technique.

In order to detect cleavage products which may have accumulated, total cell lysates were directly loaded onto SDS-PAGE gels, run in electrophoresis, transferred to nitrocellulose, and immunoblotted with the two different anti-RPTPκ peptide antisera (described above) specific for either the N-terminus or for an epitope near the first PTPase homology domain in the intracellular portion.

In lysates from transfected cells, but not from mock transfected cells, both antisera recognized the same 210 kDa protein described above. The antiserum specific for the N terminus also recognized a smaller 110 kDa protein. The antiserum specific for the cytoplasmic region recognized a smaller 100 kDa protein (FIG. 9).

The three polypeptides (210, 110 and 100 kDa) were further characterized by subjecting the total cell lysates to endoglycosidase F digestion before SDS-PAGE and immunoblotting. Such a treatment would be expected mainly to affect the mobility of a protein containing the glycosylated extracellular domain. Following endoglycosidase F treatment, the mobility of the 210 kDa and 110 kDa proteins was significantly reduced, to 160 kDa and 89 kDa respectively. In contrast, the mobility of the 100 kDa band detected with antiserum 122 specific for an epitope in the intracellular domain) was only slightly affected, suggesting that the 100 kDa peptide includes a minor glycosylation component (FIG. 9).

The above results, as well as pulse-chase analysis shown in FIG. 10, are consistent with the cleavage of a 210 kDa RPTPκ precursor protein into an N-terminal 110 kDa product encompassing most of the extracellular domain, and a 100 kDa moiety containing the intracellular portion and about 100 residues of extracellular sequence (FIG. 14). A consensus site for cleavage by furin, a processing endopeptidase (Hosaka et al., supra), is indeed located 113 amino acids upstream of the start of the transmembrane segment (RTKR, residues 640–643 of SEQ ID NO: 1), which would leave one potential N-glycosylation site in the C-terminal cleavage product.

In order to confirm directly that proteolytic cleavage occurred at the RTKR (SEQ ID NO: 12) (furin-recognized) site, site-directed mutagenesis was used to mutate this site to LTNR (SEQ ID NO: 13), and the effects of this mutation on the processing of the RPTPκ precursor were examined. As shown in FIG. 12, the mutant cDNA gave rise to only a 210 kDa product. These results provide evidence that the RTKR (SEQ ID NO: 12) region is the likely proteolytic cleavage signal and site for processing, of the RPTPκ proprotein.

The inventors next tested whether the cleavage products were associated. This was accomplished by performing an immunoprecipitation with antiserum 116, specific for the extracellular 110 kDa product, on lysates of cells transfected with the wild type (wt) RPTPκ cDNA. Immunoblotting of this precipitate with antiserum 122, specific for an intracellular RPTPκ epitope, detected the presence of the 100 kDa C-terminal cleavage product in the precipitate (FIG. 12). This observation strongly suggested that at least a portion of the two RPTPκ cleavage products remained associated after cleavage, and that the 100 and 110 kDa species may be considered as subunits of a single complex (FIG. 14). Experiments with a secreted form of the extracellular domain of RPTPκ suggested that this association was not mediated by a disulfide linkage, since no association could be detected using SDS-PAGE under nonreducing conditions.

A similar posttranslational processing event has been described for the RPTPase LAR and for the Ng-CAM protein (Burgoon, M. et al. 1992. J. Cell Biol. 112:1017–1029; Streuli, M. et al., 1992 EMBO J. 11:897–907; Yu, Q. et al., 1992 Oncogene 7:1051–1057). In addition, a potential cleavage site exists in the corresponding position in mRPTPμ (Gebbink et al., supra). It is therefore likely that proteolytic processing of RPTPs may be a more general phenomenon.

Such cleavage, as described above, may allow controlled shedding of the N-terminal 110 kDa subunit, and thus render the membrane-bound 100 kDa form of RPTPκ insensitive to modulation by binding of proteins in the cellular environment. Alternatively, shedding might release a soluble species which retains binding activity to the putative RPTPκ ligands. Interestingly, secreted soluble forms of extracellular domains have been described for tyrosine kinase receptors such as the FGF-receptor (Johnson, D. E. et al., *Molec. Cell. Biol.* 11:4627–4634 (1991)). However these secreted forms were generated by an alternative splicing mechanism.

10. EXAMPLE: ISOLATION AND ANALYSIS OF HUMAN RPTPκ (MCP7) cDNA CLONES

10.1. PCR and cDNA Cloning Methods

Poly(A)+ RNA was isolated from SK-BR-3 cells (ATCC HTB30) and cDNA synthesized using avian myeloblastosis virus (AMV) reverse transcriptase as described (Sambrook, J. et al., *MOLECULAR CLONING: A LABORATORY MANUAL*, 2nd Edition, Cold Spring Harbor Press, Cold Spring Harbor, N.Y. (1989)). Polymerase chain reaction using a pool of degenerated oligonucleotides based on two highly conserved regions of the PTPase domain (Vogel, W. et al., *Science* 259:1611–1614 (1993) was performed under standard conditions, and PCR products were subcloned in Bluescript KS+ vector (Stratagene). Sequence analysis was done by the dideoxynucleotide chain termination method (Sanger et al., 1977) using Sequenase (United States Biochemical). a lambda ZAP 11 LIBRARY (Stratagene) from SK-BR-3 poly(A)+ RNA was screened with a PCR fragment probe under high stringency conditions (Ullrich, A. et al., 1985, Nature 313:756–711).

10.2. Results

The complexity of PTPases expressed in the human breast cancer cell line SK-BR-3 was examined by performing a PCR analysis. The primers were degenerate sequences corresponding to conserved sequences within the PTP catalytic domains shared by all identified PTPases (Vogel, W. et al. 1993, Science 259:1611–1614). Sequence analysis of the cloned PCR products revealed the presence of several known PTPases, including PTP1B, LAR, TC-PTP, PTPδ, PTPε, PTPγ, and PTPH1, as well as some novel members of the PTPase family.

One of the novel sequences, designated MCP7 ("mammary carcinoma-derived PTPase, clone 7"), was highly represented (18%) in the 121 clones examined. The 2066 bp MCP7 PCR fragment was used to screen a λ ZAP II SK-BR-3 cDNA library at high stringency. Eleven overlapping clones spanning an overall region of approximately 6.1 kb were analyzed, revealing an open reading frame encoding 1444 amino acids, followed by a 3' untranslated region of 1.8 kb.

The nucleotide sequence of human RPTPκ (SEQ ID NO:4) is shown in FIGS. 75A–E. The deduced amino acid sequence of MCP7 (SEQ ID NO:2) is also shown in FIGS. 15A–E and displays the structural organization of a type II transmembrane PTPase (Fischer et al., 1991, Charbonneau, H. et al., Annu. Rev. Cell Biol. 8:463–493 (1992). The N-terminal hydrophobic stretch of 20–26 amino acids is typical of signal peptides (von Heijne, G., J. Mol. Biol. 184:99–105 (1985). A second region consisting of hydrophobic residues is found between positions 755 and 774 and is predicted to be a single .alpha. helical transmembrane domain. It is followed by a short region of mainly basic residues characteristic of a transfer stop sequence (Wickner, W. T. et al., Science 230:400–406 (1985)). The amino-terminal portion of the putative extracellular domain contains a sequence motif, a so called MAM domain, spanning a region of about 170 residues. The MAM structural motif was recently established by comparison of several functionally diverse receptors (including RPTP.mu. and the A5 protein) and is thought to play a role in cell adhesion (Beckmann et al., supra). This motif is followed by one possible Ig-like domain (residues 207–277). The remaining extracellular portion contains conserved sequence motifs, indicating that it is composed of four FN-III related domains corresponding to the FN-III-like domains of LAR, PTPβ and RPTPμ. The extracellular domain contains 12 potential N-glycosylation sites, indicating that MCP7 is highly glycosylated. Interestingly, MCP7 contains the motif RXR/LR (residues 640–643) within the fourth FN-III domain. This motif has been described as the cleavage site for the subtilisin-like endoprotease, furin (Barr, P. J., Cell 66:1–3 (1991); Hosaka et al., supra).

The cytoplasmic part of MCP7 is composed of two PTPase domains containing the conserved amino acid sequences typical of all known PTPases (Saito, H. et al., Cell Growth Diff. 2:59–65 (1991)). A particularly intriguing feature is the region linking the transmenibrane domain to the amino-terminal PTPase domain, which is nearly twice as large as that of most other receptor-like PTPases. A similar extended distance is shared only by the homologous PTPase, hRPTPμ (FIG. 16, 16A–B lower line). The overall homology between MCP7 and hRPTP.mu. is 77%, to which the N-terminal and C-terminal PTPase domains contribute 91% and 86%, respectively (FIG. 16A–B).

10.3. Discussion

The extracellular domain of MCP7 is composed of one MAM domain, which is a sequence motif spanning about 170 residues, which was recently established by comparison of several functionally diverse receptors (including RPTPμ and the A5 protein) and is thought to play a role in cell adhesion (Beckmann & Bork, 1993, TIBS 18:40). The extracellular domain of MCP7 further includes one Ig-like, and four FN-type III-like segments. It therefore shares structural features with some cell adhesion molecules, permitting the classification of MCP7 into the type II PTPase class.

MCP7 is highly homologous to mRPTPμ which has a more restricted expression pattern in lung, brain and heart (Gebbink et al., supra). MCP7 is expressed as a molecule consisting of two noncovalently linked subunits, a structural feature already shown for LAR. A similar processing motif was also determined within the extracellular domain of mRPTPμ (RTKR, SEQ ID NO: 12), which suggest that this structural organization is typical for the family of type II phosphatases. Proteolytic cleavage also occurs in the extracellular domain of the cell adhesion molecule Ng-CAM in a region containing the dibasic processing motif (Burgoon, M. P. et al., J. Cell. Biol. 112:1017–1029 (1991)). The functional significance of this structure is not yet clear. For LAR, a shedding of the extracellular E-subunit was observed in a density-dependent manner (Streuli et al., supra). It is likely that this shedding is due to a conformational change in the extracellular domain caused by homophilic or hydrophilic interactions between the molecules on the surface of neighboring cells that weakens the interaction between the noncovalently linked subunits. The effect of this shedding on the activity of the PTPase domains within the cells is not yet clear, but a modification of the activity of the phosphatase or a change in the sensitivity to modifying processes is probable.

11. EXAMPLE: TISSUE DISTRIBUTION OF HUMAN RPTPκ

11.1. RNA Extraction and Northern Blot Analysis

Total RNA was isolated by the guanidinium isothiocyanate method (Chirgwin et al., 1979, Biochemistry 18:5294–5299) from human tissue and cultured cells grown to confluency. Poly(A)+RNA was prepared on an oligo(dT) column (Aviv & Leder, 1972, Proc. Natl. Acad. Sci. USA 69:1408–1412). 4 μg of poly(A)+ RNA was fractionated on a 1.2% formaldehyde-agarose gel and subsequently transferred to nitrocellulose filters (Schleicher & Schuell). Hybridization was performed in 50% formamide, 5×SSC, 50M $NaH_2PO_4$, pH 6.8, 0.5% SDS, 0.1 mg/ml sonicated salmon sperm DNA, and 5× Denhardt solution at 42° C. overnight with $1-3\times10^6$ cpm/ml of $^{32}P$-labeled random-primed DNA (United States Biochemical). Filters were washed with 2×SSC, 0.1% SDS, and 0.2×SSC, 0.1% SDS at 45° C., and exposed 5 days using an intensifying screen at −80° C.

11.2. Results

Northern blot analysis revealed a broad tissue distribution of MCP7 (FIG. 17). The 6.7 kb transcript was found at elevated levels in lung and colon-tissue, and, to a lesser extent, in liver, pancreas, stomach, kidney, and placenta. No transcript was detected in spleen tissue.

The expression pattern of MCP7 in different mammary carcinoma-derived cell lines is shown in FIG. 18. Although MCP7 expression was observed in all of the cell lines tested, the quantity of transcripts differed significantly. A second transcript with a size of 4.9 kb was also detected in all cell lines displaying a strong signal. Moreover, MDA-MB-435 cells contained a specific 1.4 kb mRNA that hybridized with the MCP7 probe. It is interesting to note that the intensity of the Northern hybridization signals shown in FIG. 18 correlate with the abnormal over expression of EGF-R and HER2/neu RTKs. Expression of MCP7 was also detected in human melanoma cell lines and some colon-carcinoma derived cell lines.

12. EXAMPLE: TRANSIENT EXPRESSION OF HUMAN RPTPκ

12.1. Methods

MCP7 cDNA was cloned into a cytomegalovirus early promoter-based expression plasmid (pCMV). The RTK expression plasmids used were described previously (Vogel, W. et al., 1993 Science 259:1611–1614). At 30 hours prior transfection, $3\times10^5$ cells of human embryonic kidney fibroblast cell line 293 (ATCC CRL 1573), grown in Dulbecco's modified Eagle's medium (DMEM) which included 4500 mg/l glucose, 9% fetal calf serum, and 2 mM glutamine, were seeded into a well of a six-well dish.

Transfections with CsCl-purified plasmid DNA were then carried out using the calcium phosphate coprecipitation technique according to the protocol of Chen and Okayama (Chen, C. and Okayawa, H., 1987, Mol. Cell. Biol. 7:2745–2752) with a total amount of 4 µg, which included only 0.2 µg expression plasmid and complemented with empty vector DNA (Gorman, C. M. et al., 1989, Virology 171:377–385; Lammers, R. et al., 1990, J. Biol. Chem. 265:16886–16890). At 16 hours after transfection, cells were washed once and starved with medium containing 0.5% fetal calf serum.

For metabolic labeling, MEM containing Earle's salt, but lacking L-methionine, was used instead of DMEM. [$^{35}$S] methionine at 40 µCi/ml (1,000 Ci/mmol) was added.

Cells were stimulated with an appropriate ligand for 10 min. Epidermal growth factor (EGF) at 100 ng/ml was used to stimulate cells transfected with EGF-R, HER1/2, EK-R or EP-R. Insulin at 1 µg/ml was used to stimulate cells transfected with IR. SCF at 100 ng/ml was used to stimulate cells transfected with p145$^{c\text{-}kit}$. After stimulation, cells were lysed in 200 µl lysis buffer (50 mM HEPES, pH7.5; 150 mM NaCl, 1.5 mM MgCl$_2$, 1 mM EGTA, 10% glycerol, 1% Triton X-100, 2 mM phenylmethylsulfonylfluoride, 10 µg/ml aprotinin, 1 mM Na-orthovanadate). The lysates were precleared by centrifugation at 125,000×g for 10 min at 4° C., and ⅒ of the volume of the supernatant was mixed with SDS sample buffer.

Proteins were separated by SDS-PAGE and transferred to nitrocellulose membranes. For detection of phosphotyrosine and protein antigens on immunoblots, the ECL system (Amersham) in conjunction with horseradish peroxidase-conjugated goat anti-mouse or goat anti-rabbit antibody (Biorad) was used. In order to reprobe with other antibodies, blots were incubated for 1 hour in 67 mM Tris-HCl (pH 6.8), 2% SDS, and 0.1% β-mercaptoethanol at 50° C.

For immunoprecipitation, radiolabelled cells were incubated with antiserum at 4° C. for 2 hours, washed three times with PBS (15 mM NaCl, 3 mM Kcl, 80 mM Na$_2$HPO$_4$.H$_2$O, 1.5 mM KH$_2$PO$_4$, pH 7.4) to remove unbound antibodies, lysed, and precleared by centrifugation. Protein A-sepharose (Pharmacia) in a volume of 20 µl has added and incubated for two hours on a rotating wheel at 4° C. Precipitates were washed four times with HNTG-buffer (20 mM HEPES, ph. 7.5, 150 mM Na Cl, 0.1% Triton X-100, 10% glycerin), SDS-sample buffer added, and SDS-PAGE was performed. X-ray film was then exposed to the dried gel two days.

The polyclonal antiserum, Ab 116, specific for the extracellular domain of murine RPTPκ, was raised against a peptide sequence (residues 60–76) within the extracellular domain of the mouse homolog of MCP7, and which was perfectly conserved in the human sequence as described supra, in Section 10. The monoclonal antibody specific for phosphotyrosine, 5E.2, was described previously (Fendly, B. M. et al., 1990, Canc. Res. 50:1550–1558).

12.2. Results

Forty eight hours after transfection of MCP7 cDNA, using a cytomegalovirus promoter-based expression vector, into 293 embryonic kidney cells, radiolabelled cells were incubated with Ab 116. Cells were washed, lysed, and the antibody-bound material was immunoprecipitated.

MCP7 expression was found on the cell surface only, and appeared as a band having an apparent molecular weight of 185 kDa. The larger size than the calculated molecular weight of 163 kDa was probably due to extensive glycosylation of the extracellular domain.

Two additional bands of 97 kDa and 116 kDa were immunoprecipitated (FIG. 19, 19A, lane 1); these bands were not detectable in cells transfected with a control vector. Such lower molecular weight products were thought to be cleavage products since the extracellular domain contains a common cleavage motif (RXR/LR; residues 640–643, FIG. 15A–151E). For processing by the endoprotease furin. These products are similar to the cleavage products described above for murine RPTPκ. Furthermore, similar processing of the extracellular domain of LAR has been described (Streuli et al., supra).

The 116 kDa fragment, the a subunit, represents most of the extracellular domain and is highly glycosylated, as indicated by the broadness of the band upon polyacrylamide gel electrophoresis analysis and its apparent molecular weight, which exceeded the calculated value, based on the sequence between residing 20 and 639, by 47 kD. The 97 kDa fragment, the β subunit, corresponds to an intracellular and transmembrane domain and also includes a short extracellular segment which is thought to interact with the a subunit. The relatively minor discrepancy between the observed 97 kDa molecular weight size and the calculated 91.4 kDa molecular weight of the β subunit can be explained by the presence of only one potential N-glycosylation site.

The α and β subunit are believed to form a stable complex, such that immunoprecipitation by an antibody specific for the extracellular domain would detect both subunits. To confirm that the 116 kDa band corresponded to the o subunit cleavage product and not merely to a non-specifically cross-reacting species, lysates from MCP7 cDNA-transfected 293 cells were subjected to Western blots using antiserum 116 specific for an N-terminal epitope. With this approach, a band of about 116 kDa as well as an unprocessed precursor were found (FIG. 19B, right panel, lane 1), neither of which were detected in 293 cells at comparable levels transfected with a control vector (FIG. 19B, right panel, lane 2).

13. EXAMPLE: EXAMINATION OF PTPase ENZYMATIC ACTIVITY OF HUMAN RPTPκ

To prove that the RPTPκ designated MCP7 is indeed a PTPase enzyme, the above transient expression system in 293 cells was used.

Coexpression of MCP7 with a panel of different RTKs representing different structural subclasses allowed the examination of more physiological substrates for the PTPase as dephosphorylation targets than those commonly used.

To ensure that the protein localized mainly in the membrane and to avoid an overload of the cell transport system, these transfection experiments were performed with only small amounts of plasmid compared to the original protocols (Gorman, C. M. et al., Virology 171:377–385 (1989); Lammers, R. et al., J. Biol. Chem. 265:16886–16890 (1990)). The receptors tested were mainly chimeric receptors, the respective kinase function of which was under the control of an EGF-R extracellular domain (Lee, J. et al., EMBO J. 8:167–173 (1989); Herbst, R. et al., J. Biol. Chem. 266: 19908–19916 (1991); Seedorf, K. et al., J. Biol. Chem. 266:12424–12431 (1991)). Human 293 fibroblasts were transfected with equal amounts of expression plasmids encoding for an RTK and either MCP7 or a control vector. After stimulation with the appropriate ligand for the RTK, cells were lysed, equal aliquots were resolved by SDS PAGE, and the phosphotyrosine level of the receptors was examined by immunoblotting with the anti-phosphotyrosine antibody 5E2 (Fendly, G. M. et al., Canc. Res. 50:1550–1558 (1990)).

Co-expression of I-R, EGF-R, EP-R, EK-R, and SCF-R/c-kit with MCP7 resulted in a marked decrease in the ligand-induced receptor phosphotyrosine content when compared with control transfections in which MCP7 expression plasmid had been omitted (FIG. 20, 20A, lanes 1 and 9; 20B, lanes 1, 5, and 9). In contrast, HER1–2 appeared to be a poor substrate of MCP7, since only weak reduction of the ligand-induced phosphorylation state of this chimera was observed (FIG. 20A, lane 5). Interestingly, the intracellularly localized, incompletely processed precursor forms of I-R, EGF-R and EP-R (FIG. 20A, lanes 2, 4 and 10, 12; 20B, lanes 2, 4), as well as that of HER 1–2 (FIG. 20A, lanes 6, 8), were efficiently dephosphorylated), suggesting that MCP7 was present and active in the same intracellular compartments as the co-expressed RTKs before reaching the cell surface.

To verify the above effects and to rule out differences in RTK expression levels, the above blots were re-probed with RTK-specific and RPTPκ-specific antibodies. The results indicated that expression levels of the various RTKs were equivalent.

14. EXAMPLE: CORRELATION BETWEEN HUMAN RPTPκ EXPRESSION AND CELL DENSITY

The presence of motifs in the extracellular domain of human RPTPκ that resemble motifs found in proteins involved in cell-cell and cell-extracellular matrix interactions prompted an investigation of the effect on expression level of cell density in culture.

An equal number of SK-BR-3 cells was distributed onto either one, two, or four 15-cm dishes and incubated for two days under standard growth conditions. When harvested after two days, cells seeded at the various starting densities were found to be 100%, 70%, and 40% confluent, respectively. Poly(A)+RNA was prepared and Northern blot analysis was conducted as described supra, using a probe corresponding to the extracellular domain of MCP7. The results indicated that the level of MCP7 transcripts increased with increased cell density (FIG. 21A).

To determine whether this effect was unique to SK-BR-3 cells, an identical experiment was performed using the colon carcinoma-derived cell line HT 29. Expression of MCP7 mRNA was also found to be density-dependent with these cells (FIG. 19B).

As a control, the expression of mRNA encoding the enzyme GAPDH was examined in the above cells at various densities. No density dependence of the expression of these transcripts were obvserved.

The above results support the hypothesis RPTPκ, and other RPTPs of the type II and type III families, are involved in, and modulated by, cell adhesion events (Charbonneau et al., supra). PTPases appear to be involved in events leading to growth arrest by cell-cell contact (Klarlund, supra). The presence of orthovanadate, a potent inhibitor of phosphatase activity diminishes normal contact inhibition of 3T3 cells. Furthermore, PTPase activity associated with the membrane fraction of 3T3 cells increased 8 fold when cells were grown to a higher density (Pallen, C. J. et al., *Proc. Natl. Acad. Sci. USA* 88:6996–7000 (1991)).

The combination of CAM motifs in the extracellular domain or RPTPκ and the intracellular PTPase activity indicates that RPTPκ may act as an important-mediator of events associated with arrest of cell growth. The structural features of human RPTPκ described above, the density-dependent upregulation or its expression, and its potent activity in dephosphorylating RTKs supports the emerging picture of the pivotal role of RPTPκ in growth arrest through contact inhibition, as well as a role as a tumor suppressor gene.

15. EXAMPLE: HOMOPHILIC BINDING BY A RECEPTOR TYROSINE PHOSPHATASE

The present work investigates whether, similar to "classical" members of the CAM family, RPTPases might be capable of homophilic intercellular interaction (Q. Yu, T. Lenardo, R. A. Weinberg, oncogene 7, 1051 (1992)). Reasoning that analysis of cell adhesion by the RPTPase RPTPκ would be facilitated by its ectopic expression in a cell line likely to lack conserved ligands for a mammalian RPTPase, we stably introduced an RPTPκ cDNA into *Drosophila* S2 cells. These cells have a very low capacity for spontaneous aggregation or adhesion, making them an ideal and established system for such studies (H. Kramer, R. L. Cagan, S. L. Zipursky, Nature 352, 207). Cells transfected with a vector containing the RPTPκ cDNA in the sense orientation with respect to the heat-shock protein 70 (hsp 70) promoter of the vector, and induced by brief heat treatment expressed a protein of 210 kD detectable by immunoblotting with anti-RPTPκ antiserum (FIG. 22A). This protein corresponds to the unprocessed form of RPTPκ seen in mammalian cells (Y.-P. Jiang et al. Mol. Cell. Biol. 13, 2942 (1993)). In addition, after longer expression periods, a protein species of 110 kD also appeared, suggesting that the RPTPκ protein may at least, in part, partly be processed in the *Drosophila* cell line in a manner similar to the way in which it is processed in mammalian cells, i.e., through proteolytic cleavage by a furin type endoprotease (FIG. 22A) (Y.-P. Jiang et al. Mol. Cell. Biol. 13, 2942 (1993)). A *Drosophila* furin homolog has recently been described (A. J. M. Roebroek et al., EMBO J. 12, 1853 (1993)).

In order to study whether RPTPκ expression may mediate cell-cell aggregation, cells stably transfected with the RPTPκ CDNA in either the sense orientation (sense cDNA) or the antisense orientation (antisense CDNA) were tested in an aggregation assay. uninduced and heat shock-induced cells were resuspended, subjected to rotary shaking to ensure mixing and to avoid adhesion to the vessel, and were then assayed for aggregate formation. The formation of a large number of aggregates consisting of more than 10 and up to approximately 100 cells was observed in heat-shocked sense cDNA-expressing cells only, whereas control cells (i.e., antisense cDNA transfected cells or non-heat shocked cells) remained essentially single cell suspensions (FIG. 22B–22C). Two methods of quantitation, counting of aggregates under the microscope, and determination of superthreshold particles with a Coulter-counter (FIG. 22C–22D) confirmed this conclusion. The fact that aggregation was incomplete, with a large proportion of RPTPκ transfected cells remaining as single cells throughout the assay period, is most likely due to the fact that the transfected cell population consisted of an uncloned pool of cells presumably differing in their levels of RPTPκ expression. Notably, the conditions of the assay (i.e., medium, timescale, and speed of shaking) are similar to those used to demonstrate the adhesive properties of a number of well established adhesion molecules (H. Kramer, R. L. Cagan, S. L. Zipursky, Nature 352, 207 (1991); P. M. Snow, A. J. Bieber, C. Goodman, Cell 59, 313 (1989)). Therefore, in view of the difficulty of measuring binding affinities of many cell adhesion molecules which rely on cooperativity, it is likely that the strength of cell-cell-interaction conferred by expression of RPTPκ is comparable to that of established, "classical", cell adhesion molecules.

The above experiments were performed with a full-length RPTPκ cDNA, leaving unclear whether the phosphatase activity of the intracellular domain is required to confer adhesive properties. In several instances, an intact intracellular domain of cell adhesion molecules has in fact been shown to be required for certain aspects of cell-cell interaction (A. Nafaguchi and M. Takeichi, EMBO J. 7, 3679 (1988); S. H. Jaffe et al., Proc. Natl. Acad. Sci. USA 87, 3589 (1990), R. O. Hynes, Cell 69,111(1992)). To test this issue, a cDNA encoding a mutant protein lacking most of the intracellular, catalytic, domain of RPTPκ was constructed. FIG. 22E shows that such a truncation did not negatively interfere with cell aggregation as measured in this type of assay. The role of the furin cleavage site in the extracellular domain of RPTPκ was also tested. Mutation of this site also left the adhesive behavior intact, suggesting that cleavage of the RPTPκ proprotein (Y.-P. Jiang et al. Mol. Cell. Biol. 13, 2942 (1993)) is not required for induction of cell aggregation.

Cell adhesion molecules have been described which either do (e.g. cadherin family members and integrins), or do not (e.g. N-CAM, Ng-CAM) require the presence of $Ca^{++}$ (G. M. Edelman, Immun. Rev. 100, 11(1987); A. F. Williams and A. N. Barclay, Annu. Rev. Immunol. 6, 381 (1988); M. Grumet, Curr. Opin. Neurobiol. 1, 370 (1991), R. O. Hynes, Cell 69,111 (1992), B. Geiger and O. Ayalon, Annu. Rev. Cell Biol. 8 (1992)). The experiments presented in FIG. 22A–22E were performed in the presence of 10 mM $Ca^{++}$ in the aggregating cell suspension. Performing a similar experiment in the absence of calcium ions and in the presence of 1 mm EGTA revealed no calcium requirement for RPTPκ mediated cellular aggregation under the conditions of the assay.

The observed aggregation correlating with expression of RPTPκ could be accounted for by either a homophilic binding mechanism, in which cell-cell binding is mediated by interaction between RPTPκ proteins on different cells within aggregates, or by binding of the RPTPκ proteins to a second cell-surface ligand intrinsic to the parental transfected cells. It was possible to distinguish between these two hypotheses by marking difference populations of cells with the fluorescent lipophilic dye 1,1'-dioctadecyl-3,3,3',3'tetramethylindocarbocyanine perchlorate (diI) (J. Schlessinger et al. Science 195, 307(1977)0, and then testing them for their ability to co-aggregate. In these experiments, RPTPκ expressing and non-expressing cells were labeled with diI, mixed with unlabeled cells of either RPTPκ expressing or non-expressing types, and the presence of cells of either type in the aggregates formed was monitored by fluorescence microscopy. The results are illustrated in FIG. 23A–23C. Strikingly, mixing of unlabeled, RPTPκ positive cells with labeled, RPTPκ negative cells led to the formation of aggregates consisting exclusively of unlabeled cells. Conversely, when the RPTPκ expressing cells were labeled and allowed to aggregate with unlabeled control cells, aggregates consisted entirely of labeled, demonstrating that diI labeling does not interfere with the aggregation capacity of the transfected cells. Mixing of labeled and unlabeled cells, both expressing RPTPκ, led to the formation of mixed aggregates consisting of cells of either staining type, thus confirming that both diI stained and unstained cells have the ability to coaggregate. These results suggest that aggregation of the RPTPκ transfected cells requires the presence of the protein on all cells within the aggregate, implying a homophilic binding mechanism.

It was next determined whether the extracellular domain of RPTPκ was able to function by itself as a substrate for attachment of cells expressing the RPTPκ protein independent of other factors to assist in the adhesion process. A baculovirus expression system was used to produce a soluble recombinant protein consisting of virtually the entire extracellular domain of the RPTPκ protein, fused to placental alkaline phosphatase, which served as a tag for purification and detection (J. G. Flanahan and P. Leder, Cell 63, 185 (1990)). Fusion between the two protein moieties was designed to occur precisely before the furin proteolytic cleavage signal in the fourth fibronectin type III repeat in RPTPκ (Y.-P. Jiang et al. Mol. Cell. Biol. 13, 2942 (1993)). The purified recombinant protein (K2AP) was used to coat bacteriological Petri dishes, and monitored for its ability to allow attachment of RPTPκ-expressing S2 cells. Only induced, RPTPκ expressing cells showed adhesive behavior to the K2AP coated surface (FIG. 24A–24D; Table II below).

TABLE II

| Cell type: | S2 control un-induced | S2 control induced | S2-R-PTP-κ un-induced | S2-R-PTP-κ induced | L6 | L6R-PTP-κ |
|---|---|---|---|---|---|---|
| Protein | | | | | | |
| K2AP-a | − | − | − | +++ | + | ++ |
| K2AP-b | − | − | − | +++ | + | ++ |
| AP | − | − | − | − | − | − |
| HER | − | − | − | − | − | − |
| BSA | − | − | − | − | − | − |
| Fibronectin | +++ | +++ | +++ | +++ | + | + |
| polylysine | n.d. | n.d. | n.d. | n.d. | +++ | +++ |

Summary of adhesion data of different cell types to surfaces coated with purified K2AP protein, or other proteins (−:no cells attached; +:50–150 cells; ++150–500; +++:>500; n.d.: not determined)

K2APa: K2AP protein purified by elution from affinity column at alkaline pH.

K2APb: K2AP protein purified by elution from affinity column using 50% ethylene glycol.

AP: alkaline phosphatase control protein (J. G. Flanahan and P. Leder, Cell 63, 185 (1990)), corresponding to the tag portion of the K2AP fusion protein.

HER: Human EGF-receptor extracellular domain affinity-purified from a baculovirus expression system (I. Lax et al., J. Biol. Chem. 266, 13828 (1991)).

BSA: bovine serum albumin.

L6-R-PTPκ: a clone of L6 cells stably transfected with the R-PTPκ protein.

No attachment occurred to control coated surfaces, which included alkaline phosphatase or the recombinant extracellular domain of human EGF-receptor (I. Lax et al., J. Bid. Chem. 266, 13828 (1991)), also purified by affinity chromatography from a baculovirus expression system. Whereas the above experiments were performed in the context of insect cells, the effect of RPTPκ protein expression in mammalian cells in a similar cell-to-substrate adhesion assay was also tested. In contrast to parental Drosophila S2 cells, rat L6 myoblast cells, the mammalian cell line used as a recipient for RPTPκ overexpression, already shows a low level of spontaneous adhesion to a K2AP protein coated surface. However, stable overexpression of an RPTPκ cDNA in these cells led to a significant (2.7 fold .+−.1.0; n=3) increase in adhesive capacity to a surface coated with the recombinant soluble extracellular domain of the RPTPκ protein (FIG. 24A–24D).

15.1 Discussion

Cell-cell contact is generally considered to play a critical role in various aspects of malignancy. For example, escape from contact inhibition is a classical parameter of transformation, and, additionally, many links between cell-cell interactions and such phenomena as tumor invasion and metastasis are apparent (F. Van Roy and M. Mareel, TICB 2, 163 (1992)). The above data clearly demonstrate that an RPTPase of the LAR-like subfamily (containing a combination of Ig and fibronectin type III domains) is capable of homophilic binding between neighboring cells, leading to the identification of a function for the extracellular domains of such molecules. This makes it likely that other members of this RPTPase subfamily can behave in a similar fashion; and extends the series of links that have recently emerged between the adhesive properties of cells, and signal transduction pathways involving tyrosine phosphorylation. For instance, adherens junctions correspond to sites of increased tyrosine phosphorylation and appear to be subject to its control, and reagents directed at integrins or extracellular domains of established CAMs have been shown to elicit changes in cellular tyrosine phosphorylation (J. R. Atashi et al., Neuron 8, 831 (1992); T. Volberg et al., EMBO J. 11, 1733 (1992); R. L. Juliano and S. Haskill, J. Cell Biol. 120, 577 (1993)). In addition, reagents directed toward cell adhesion molecules are known to activate a number of second messenger signals (Schuch, U. Lohse, M. Schachner, Neuron 3, 13–20 (1989); P. Doherty, S. V. Ashton, S. E. Moore, F. Walsh, Cell 67, 21 (1991)). The above observation suggests mechanisms by which such signals might be generated. For example, direct cell-cell contact between RPTPases on adjacent cells could lead to local RPTPase oligomerization events affecting either the catalytic activity or localization of RPTPases, which in turn have been suggested to modulate the activity of src-family tyrosine kinases (H. L. Ostergaard et al., Proc. Natl. Acad. Sci. USA 86, 8959 (1989); T. Mustelin and A. Altman, Oncogene 5, 809 (1989); X. M. Zheng, Y. Wang, C. J. Pallen, Nature 359, 336 (1992)). Moreover, the similar structural and functional properties of the extracellular domains of RPTPases and CAMs prompts the speculation that RPTPases may, in addition to self-interaction, also be capable of interacting heterophilically with other molecules involved in cell adhesion, whether in cis or in trans (G. M. Edelman, Immun. Rev. 100, 11 (1987); A. F. Williams and A. N. Barclay, Annu. Rev. Immunol. 6, 381 (1988); M. Grumet, Curr. Opin. Neurobiol. 1, 370 (1991), R. O. Hynes, Cell 69,111 (1992), B. Geiger and O. Ayalon, Annu. Rev. Cell Biol. 8 (1992), M. Grumet and G. M. Edelman, J. Cell Biol. 106, 487–503 (1988); G. A. Kadmon, A. Kowitz, P. Altevogt, M. Schachner, J. Cell Biol. 110, 193 (1990); A. A. Reyes, R. Akeson, L. Brezina, G. J. Cole, Cell Reg. 1, 567 (1990); P. Sonderegger and F. G. Rathjen, J. Cell Biol. 119, 1387 (1992); M. G. Grumet, A. Flaccus, R. U. Margolis, J. Cell Biol. 120, 815 (1993)).

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An isolated antibody which specifically binds to a mammalian protein or glycoprotein comprising the amino acid sequence of SEQ ID NO: 1.

2. The antibody of claim 1, wherein the antibody is a monoclonal antibody.

3. An isolated antibody which specifically binds to a protein or glycoprotein comprising the full length amino acid sequence of SEQ ID NO: 2, wherein said antibody binds to an epitope located within the amino acid sequence of SEQ ID NO:2.

4. The antibody of claim 3, wherein the antibody is a monoclonal antibody.

5. An isolated antibody which specifically binds to a mammalian protein comprising at least one of the following domains in SEQ ID NO: 1: the signal peptide domain, the MAM domain, the Ig-like domain, one of the four FN-type III like domains, the phosphatase I domain, the phosphatase II domain, the extracellular domain, the transmembrane domain or the intracellular domain, wherein said antibody binds to an epitope located within the amino acid sequence of SEQ ID NO:1.

6. The antibody of claim 5, wherein the antibody is a monoclonal antibody.

7. An isolated antibody which specifically binds to a mammalian protein comprising at least one of the following domains in SEQ ID NO:2: the signal peptide domain, the MAM domain, the Ig-like domain, one of the four FN-type III like domains, the phosphatase I domain, the phosphatase II domain, the extracellular domain, the transmembrane domain or the intracellular domain, wherein said antibody binds to an epitope located within the amino acid sequence of SEQ ID NO:2.

8. The antibody of claim 7, wherein the antibody is a monoclonal antibody.

9. The isolated antibody of claim 5 which binds to the signal peptide domain.

10. The isolated antibody of claim 5 which binds to the MAM domain.

11. The isolated antibody of claim 5 which binds to the Ig-like domain.

12. The isolated antibody of claim 5 which binds to a FN-Type III domain.

13. The isolated antibody of claim 5 which binds to the phosphatase I domain.

14. The isolated antibody of claim 5 which binds to the phosphatase II domain.

15. The isolated antibody of claim 5 which binds to the extracellular domain.

16. The isolated antibody of claim 5 which binds to the transmembrane domain.

17. The isolated antibody of claim 5 which binds to the intracellular domain.

18. The isolated antibody of claim 7 which binds to the signal peptide domain.

19. The isolated antibody of claim 7 which binds to the MAM domain.

20. The isolated antibody of claim 7 which binds to the Ig-like domain.

21. The isolated antibody of claim 7 which binds to a FN Type-III domain.

22. The isolated antibody of claim 7 which binds to the phosphatase I domain.

23. The isolated antibody of claim 7 which binds to the phosphatase II domain.

24. The isolated antibody of claim 7 which binds to the extracellular domain.

25. The isolated antibody of claim 7 which binds to the transmembrane domain.

26. The isolated antibody of claim 7 which binds to the intracellular domain.

27. An isolated antibody which specifically binds to a polypeptide comprising amino acids 60–76 of SEQ ID NO:1.

28. An isolated antibody which specifically binds to a polypeptide amino acids 910–929 of SEQ ID NO:1.

29. An isolated antibody which specifically binds to a mammalian protein or glycoprotein comprising the amino acid sequence of SEQ ID NO:1 wherein said antibody binds to the transmembrane domain.

30. An isolated antibody which specifically binds to a mammalian protein or glycoprotein comprising the amino acid sequence of SEQ ID NO:2 wherein said antibody binds to the transmembrane domain.

31. An isolated antibody which specifically binds to an extracellular domain of a mammalian protein or glycoprotein of SEQ ID NO:1.

32. An isolated antibody which specifically binds to an extracellular domain of a mammalian protein or glycoprotein of SEQ ID NO:2.

* * * * *